(12) United States Patent
Kaleko et al.

(10) Patent No.: US 12,648,987 B2
(45) Date of Patent: **\*Jun. 9, 2026**

(54) ALKALINE PHOSPHATASE AGENTS FOR TREATMENT OF RADIATION DISORDERS

(71) Applicant: Theriva Biologics, Inc., Rockville, MD (US)

(72) Inventors: Michael Kaleko, Rockville, MD (US); Christian Furlan Freguia, Rockville, MD (US); Sheila Connelly, Rockville, MD (US)

(73) Assignee: Theriva Biologics, Inc., Rockville, MD (US)

( \* ) Notice: Subject to any disclaimer, the term of this patent is extended or adjusted under 35 U.S.C. 154(b) by 531 days.

This patent is subject to a terminal disclaimer.

(21) Appl. No.: 18/300,634

(22) Filed: Apr. 14, 2023

(65) Prior Publication Data

US 2023/0310558 A1      Oct. 5, 2023

Related U.S. Application Data

(63) Continuation of application No. 16/982,211, filed as application No. PCT/US2019/023143 on Mar. 20, 2019, now Pat. No. 11,654,184.

(60) Provisional application No. 62/714,398, filed on Aug. 3, 2018, provisional application No. 62/645,469, filed on Mar. 20, 2018.

(51) Int. Cl.
| | |
|---|---|
| *A61K 38/46* | (2006.01) |
| *A61K 9/00* | (2006.01) |
| *A61P 1/00* | (2006.01) |
| *A61P 39/00* | (2006.01) |

(52) U.S. Cl.
CPC .......... *A61K 38/465* (2013.01); *A61K 9/0053* (2013.01); *A61P 39/00* (2018.01); *C12Y 301/03001* (2013.01); *A61P 1/00* (2018.01)

(58) Field of Classification Search
CPC ..... A61K 38/465; A61K 9/0053; A61P 39/00; A61P 1/00; C12Y 301/03001
See application file for complete search history.

(56) References Cited

U.S. PATENT DOCUMENTS

| | | | |
|---|---|---|---|
| 5,773,226 | A | 6/1998 | Millan |
| 5,821,095 | A | 10/1998 | Hattori et al. |
| 5,891,699 | A | 4/1999 | Boulain et al. |
| 5,948,410 | A | 9/1999 | Van Scharrenburg et al. |
| 6,290,952 | B1 | 9/2001 | Poelstra et al. |
| 6,406,899 | B1 | 6/2002 | Hoelke et al. |
| 6,638,531 | B1 | 10/2003 | Amerongen et al. |
| 6,649,390 | B1 | 11/2003 | Sheng et al. |
| 6,686,392 | B1 | 2/2004 | Avram et al. |
| 6,756,063 | B2 | 6/2004 | Kiss |
| 6,793,928 | B1 | 9/2004 | Van Scharrenburg et al. |

| | | | |
|---|---|---|---|
| 6,884,602 | B2 | 4/2005 | Mueller et al. |
| 6,905,689 | B2 | 6/2005 | Schneidinger et al. |
| 7,011,965 | B2 | 3/2006 | Kiss |
| 7,014,852 | B2 | 3/2006 | Kiss |
| 7,048,914 | B2 | 5/2006 | Kiss |
| 7,060,677 | B1 | 6/2006 | Van Berkel et al. |
| 7,312,198 | B2 | 12/2007 | Kiss |
| 7,374,754 | B2 | 5/2008 | Kiss |
| 7,423,029 | B1 | 9/2008 | Kiss |
| 7,501,116 | B2 | 3/2009 | Kiss |
| 7,557,081 | B2 | 7/2009 | Kiss |
| 7,589,083 | B2 | 9/2009 | Kiss |
| 7,655,620 | B2 | 2/2010 | Kiss |
| 7,695,714 | B2 | 4/2010 | Kiss |
| 7,718,170 | B2 | 5/2010 | Kiss |
| 7,763,712 | B2 | 7/2010 | Crine et al. |
| 7,781,423 | B2 | 8/2010 | Kiss |
| 7,786,082 | B2 | 8/2010 | Kiss |
| 7,790,685 | B2 | 9/2010 | Kiss |
| 7,858,085 | B2 | 12/2010 | Kiss |
| 7,943,126 | B2 | 5/2011 | Tomatsu et al. |
| 7,943,606 | B2 | 5/2011 | Kiss |
| 7,960,529 | B2 | 6/2011 | Crine et al. |
| 7,964,188 | B2 | 6/2011 | Kiss |
| 8,372,638 | B2 | 2/2013 | Kiss |
| 8,460,654 | B2 | 6/2013 | Kiss |
| 8,557,545 | B2 | 10/2013 | Velders et al. |
| 8,574,863 | B2 | 11/2013 | Brands et al. |
| 8,586,032 | B2 | 11/2013 | Pickkers et al. |
| 8,603,464 | B2 | 12/2013 | Kiss |
| 8,647,854 | B2 | 2/2014 | Lee et al. |

(Continued)

FOREIGN PATENT DOCUMENTS

| | | |
|---|---|---|
| EP | 1952823 A1 | 8/2008 |
| EP | 1759001 B1 | 4/2011 |

(Continued)

OTHER PUBLICATIONS

English Language Translation of WO-2014007229-A1. Published Jan. 9, 2014. Accessed on Sep. 29, 2025. 17 pages total. (Year: 2014).*

(Continued)

*Primary Examiner* — Anand U Desai

*Assistant Examiner* — Andrew T Moehlman

(74) *Attorney, Agent, or Firm* — Morgan, Lewis & Bockius LLP

(57) ABSTRACT

The present invention relates to, inter alia, compositions and methods, including therapeutic alkaline phosphatases that find use in the treatment or prevention of the effects of radiation exposure and/or chemotherapy.

15 Claims, 13 Drawing Sheets

Specification includes a Sequence Listing.

(56) References Cited

U.S. PATENT DOCUMENTS

| | | | |
|---|---|---|---|
| 8,691,208 B2 | 4/2014 | Tomatsu et al. | |
| 8,735,087 B2 | 5/2014 | Brands et al. | |
| 8,778,674 B2 | 7/2014 | Kiss | |
| 8,784,805 B2 | 7/2014 | Brands | |
| 8,784,833 B2 | 7/2014 | Sly et al. | |
| 8,932,587 B2 | 1/2015 | Hodin et al. | |
| 9,133,446 B2 | 9/2015 | Aiba et al. | |
| 9,631,185 B2 | 4/2017 | Schyns et al. | |
| 9,926,544 B2 | 3/2018 | Raaben et al. | |
| 9,976,129 B2 | 5/2018 | Kamiya et al. | |
| 9,988,620 B2 | 6/2018 | Crine et al. | |
| 10,000,532 B2 | 6/2018 | Crine et al. | |
| 10,052,366 B2 | 8/2018 | Crine et al. | |
| 10,449,236 B2 | 10/2019 | Marozsan et al. | |
| 10,570,380 B2 | 2/2020 | Jonk et al. | |
| 10,603,361 B2 | 3/2020 | Odrljin | |
| 11,654,184 B2 * | 5/2023 | Kaleko | A61K 38/465 |
| | | | 424/94.6 |
| 2004/0091530 A1 | 5/2004 | Ende et al. | |
| 2007/0280922 A1 | 12/2007 | Kiss | |
| 2010/0158888 A1 | 6/2010 | Kiss | |
| 2010/0221234 A1 | 9/2010 | Crine et al. | |
| 2010/0297119 A1 | 11/2010 | Crine et al. | |
| 2011/0052560 A1 | 3/2011 | Brands | |
| 2011/0206654 A1 | 8/2011 | Hodin et al. | |
| 2012/0244169 A1 * | 9/2012 | Lipson | A61P 39/00 |
| | | | 530/389.2 |
| 2012/0308526 A1 | 12/2012 | Ohtake et al. | |
| 2013/0045192 A1 | 2/2013 | Movalia et al. | |
| 2013/0108635 A1 | 5/2013 | Crine et al. | |
| 2013/0280232 A1 | 10/2013 | Brands et al. | |
| 2013/0323244 A1 | 12/2013 | Crine et al. | |
| 2015/0216813 A1 | 8/2015 | Everett et al. | |
| 2017/0252327 A1 | 9/2017 | Hodin et al. | |

FOREIGN PATENT DOCUMENTS

| | | | |
|---|---|---|---|
| EP | 2158319 B1 | 7/2011 | |
| EP | 2368999 B1 | 3/2014 | |
| EP | 2662448 B1 | 12/2016 | |
| JP | 2017192381 | 10/2017 | |
| JP | 2017192381 A * | 10/2017 | |
| WO | WO 1999/026654 A1 | 6/1999 | |
| WO | WO 1999/033955 A1 | 7/1999 | |
| WO | WO 1999/037678 A2 | 7/1999 | |
| WO | WO 2000/032629 A2 | 6/2000 | |
| WO | WO 2001/034641 A2 | 5/2001 | |
| WO | WO 2001/056627 A1 | 8/2001 | |
| WO | WO 2002/060503 A1 | 8/2002 | |
| WO | WO 2004/112494 A2 | 12/2004 | |
| WO | WO 2005/055956 A2 | 6/2005 | |
| WO | WO 2005/074978 A1 | 8/2005 | |
| WO | WO 2005/103263 A1 | 11/2005 | |
| WO | WO 2007/055760 A2 | 5/2007 | |
| WO | WO 2007/081654 A1 | 7/2007 | |
| WO | WO 2008/024103 A1 | 2/2008 | |
| WO | WO 2008/094037 A1 | 8/2008 | |
| WO | WO 2008/104199 A1 | 9/2008 | |
| WO | WO 2008/104200 A1 | 9/2008 | |
| WO | WO 2008/133511 A2 | 11/2008 | |
| WO | WO 2008/138131 A1 | 11/2008 | |
| WO | WO 2009/028943 A1 | 3/2009 | |
| WO | WO 2009/106368 A1 | 9/2009 | |
| WO | WO 2010/025267 A2 | 3/2010 | |
| WO | WO 2010/151526 A1 | 12/2010 | |
| WO | WO 2011/057250 A1 | 5/2011 | |
| WO | WO 2011/134084 A1 | 11/2011 | |
| WO | WO 2012/054057 A1 | 4/2012 | |
| WO | WO 2012/169892 A2 | 12/2012 | |
| WO | WO 2012/177100 A2 | 12/2012 | |
| WO | WO 2013/058833 A1 | 4/2013 | |
| WO | WO 2013/059491 A1 | 4/2013 | |
| WO | WO-2014007229 A1 * | 1/2014 | C12Q 1/42 |
| WO | WO 2015/112015 A1 | 7/2015 | |
| WO | WO 2015/112017 A1 | 7/2015 | |
| WO | WO 2015/166045 A2 | 11/2015 | |
| WO | WO 2016/090251 A1 | 6/2016 | |
| WO | WO 2016/123342 A2 | 8/2016 | |
| WO | WO 2017/031114 A1 | 2/2017 | |
| WO | WO 2017/058822 A1 | 4/2017 | |
| WO | WO 2017/074466 A1 | 5/2017 | |
| WO | WO 2017/155569 A1 | 9/2017 | |
| WO | WO 2017/173395 A1 | 10/2017 | |
| WO | WO 2017/173413 A1 | 10/2017 | |
| WO | WO 2017/214130 A1 | 12/2017 | |
| WO | WO 2018/009555 A1 | 1/2018 | |
| WO | WO 2018/035420 A1 | 2/2018 | |
| WO | WO 2018/127363 A1 | 7/2018 | |
| WO | WO 2018/164995 A1 | 9/2018 | |
| WO | WO 2018/175413 A1 | 9/2018 | |
| WO | WO 2018/183720 A1 | 10/2018 | |
| WO | WO 2017/203426 A1 | 2/2019 | |
| WO | WO 2018/183720 A9 | 7/2019 | |
| WO | WO 2019/139891 A1 | 7/2019 | |
| WO | WO 2019/172766 A1 | 9/2019 | |
| WO | WO 2019/183208 A1 | 9/2019 | |
| WO | WO 2019/190752 A1 | 10/2019 | |
| WO | WO 2019/245938 A1 | 12/2019 | |
| WO | WO 2020/033867 A2 | 2/2020 | |

OTHER PUBLICATIONS

Hauer-Jensen, et al. "Radiation enteropathy—pathogenesis, treatment and prevention." Nature reviews Gastroenterology & hepatology 11, No. 8 (2014): 470-479. (Year: 2014).*

Rentea et al. "Radiation-induced changes in intestinal and tissue-nonspecific alkaline phosphatase: implications for recovery after radiation therapy." American journal of surgery vol. 212,4 (2016): 602-608. doi:10.1016/j.amjsurg.2016.06.005 (Year: 2016).*

English Language Translation of JP-2017192381-A. Published Oct. 26, 2017. Accessed on Sep. 29, 2025. 5 pages total. (Year: 2017).*

Hauer-Jensen et al., "Radiation enteropathy—pathogenesis, treatment and prevention," Nat. Rev. Gastroenterol. Hepatol., 2014, vol. 11, No. 8, pp. 470-479.

International Search Report and Written Opinion for Application No. PCT/US2019/023143, dated Jul. 5, 2019, 12 pages.

Garau, et al., "Radiobiology of the acute radiation syndrome", Reports of practical oncology and radiotherapy, Greatpoland cancer center/Polish society of radiation oncology, PL, vol. 16, No. 4, pp. 123-130, (2011).

Alshahrani, et al., "Stability-enhanced Hot-melt Extruded Amorphous Solid Dispersions via Combinations of Soluplus® and HPMCAS-HF," American Association of Pharmaceutical Scientists, vol. 16, No. 4, pp. 824-834, Aug. 2015.

Beumer, et al., "Calf Intestinal Alkaline Phosphatase, A Novel Therapeutic Drug for Lipopolysaccharide (LPS)-Mediated Diseases, Attenuates LPS Toxicity in Mice and Piglets," The Journal of Pharmacology and Experimental Therapeutics, vol. 307, No. 2, pp. 737-744 (Jul. 2003).

Chen, et al., "A Role for Intestinal Alkaline Phosphatase in the Maintenance of Local Gut Community," Dig Dis Sci. Apr. 2011; 56(4): 1020-1027 (doi:10.1007/s10620-010-1396-x).

Chen, et al. "Identification of specific targets for the gut mucosal defense factor intestinal alkaline phosphatase," American Journal of Physiology, Aug. 2010, Epub May 2012, vol. 299, No. 2 pp. G467-G475.

Cui, et al., "Faecal microbiota transplantation protects against radiation-induced toxicity", EMBO Molecular Medicine vol. 9 | No. 4 | 2017, 14 pages.

Curatolo, et al., "Utility of Hydroxypropylmethylcellulose Acetate Succinate (HPMCAS) for Initiation and Maintenance of Drug Supersaturation in the GI Milieu," Pharmaceutical Research, vol. 26, No. 6, pp. 1419-1431 (Jun. 2009).

Economopoulos, et al., "Prevention of antibiotic-associated metabolic syndrome in mice by intestinal alkaline phosphatase," Diabetes, Obesity and Metabolism, vol. 18, No. 5., pp. 519-527 (May 2016).

(56) References Cited

OTHER PUBLICATIONS

Estaki, et al., "Interplay between intestinal alkaline phosphatase, diet, gut microbes and immunity," World Journal of Gastroenterology, 20(42), pp. 15650-15656 (Nov. 2014).

Friesen, et al., "Hydroxypropyl Methylcellulose Acetate Succinate-Based Spray-Dried Dispersions: An Overview," Molecular Pharmaceuticals, vol. 5, No. 6, pp. 1003-1019 (Dec. 2008).

Goldberg, et al., "Intestinal alkaline phosphatase is a gut mucosal defense factor maintained by enteral nutrition," PNAS, vol. 105, No. 9, pp. 3551-3556 (Mar. 2008).

Hauer-Jensen, et al., "Radiation Enteropathy—Pathogenesis, Treatment, and Prevention", Nat Rev Gastroenterol Hepatol. Aug. 2014 ; 11(8): 470-479. doi:10.1038/nrgastro.2014.46, 27 pages.

International Search Report & Written Opinion, PCT/US2018/ 023327, May 25, 2018, 12 pages.

Kaliannan, et al., "Intestinal alkaline phosphatase prevents metabolic syndrome in mice," PNAS, vol. 110, No. 17, pp. 7003-7008 (Apr. 2013).

Lallès, "Intestinal alkaline phosphatase: novel functions and protective effects," Nutrition Reviews, vol. 72(2), pp. 82-94 (2014).

Liu, et al., "Intestinal Alkaline Phosphatase Regulates Tight Junction Protein Levels", J Am Coll Surg. Jun. 2016: 222(6): 1009-1017. doi:10.1016/j.jamcollsurg.2015.12.006.

Malo, et al., "Intestinal alkaline phosphatase preserves the normal homeostasis of gut microbiota," Gut 2010;59:1476-1484 (doi:10.1136/gut.2010.211706).

Parlato, et al., "Human ALPI deficiency causes inflammatory bowel disease and highlights a key mechanism of gut homeostasis," EMBO Molecular Medicine, e8483, pp. 1-12 (Mar. 2018).

Peters, et al., "The Potential of Alkaline Phosphatase as a Treatment for Sepsis-Associated Acute Kidney Injury," Nephron Clin Pract 2014; 127: pp. 144-148 (Sep. 2014).

Ramasamy, et al., "Intestinal Alkaline Phosphatase Has Beneficial Effects in Mouse Models of Chronic Colitis", Inflamm Bowel Dis. Feb. 2011; 17(2): 532-542. doi:10.1002/ibd.21377.

Rentea, et al., "Radiation-induced changes in intestinal and tissue-nonspecific alkaline phosphatase: implications for recovery after radiation therapy", The American Journal of Surgery (2016) 212, 602-608, 7 pages.

Rieder, et al., "Animal models of intestinal fibrosis: new tools for the understanding of pathogenesis and therapy of human disease", Am J Physiol Gastrointest Liver Physiol 303: G786-G801, 2012, 16 pages.

Shah, et al., "Improved Human Bioavailability of Vemurafenib, a Practically Insoluble Drug, Using an Amorphous Polymer-Stabilized Solid Dispersion Prepared by a Solvent-Controlled Coprecipitation Process," Journal of Pharmaceutical Sciences, vol. 102, No. 3, pp. 967-981 (Mar. 2013).

Baskar, R., et al., "Cancer and radiation therapy: current advances and future directions", Int. J. Med. Sci., vol. 9, No. 3, pp. 193-199, 2012.

* cited by examiner

Radiation-induced gut hyperpermeability

Serum FITC 4-hour after gavage

Radiation-induced gut hyperpermeability
Figure 3a                          Figure 3b
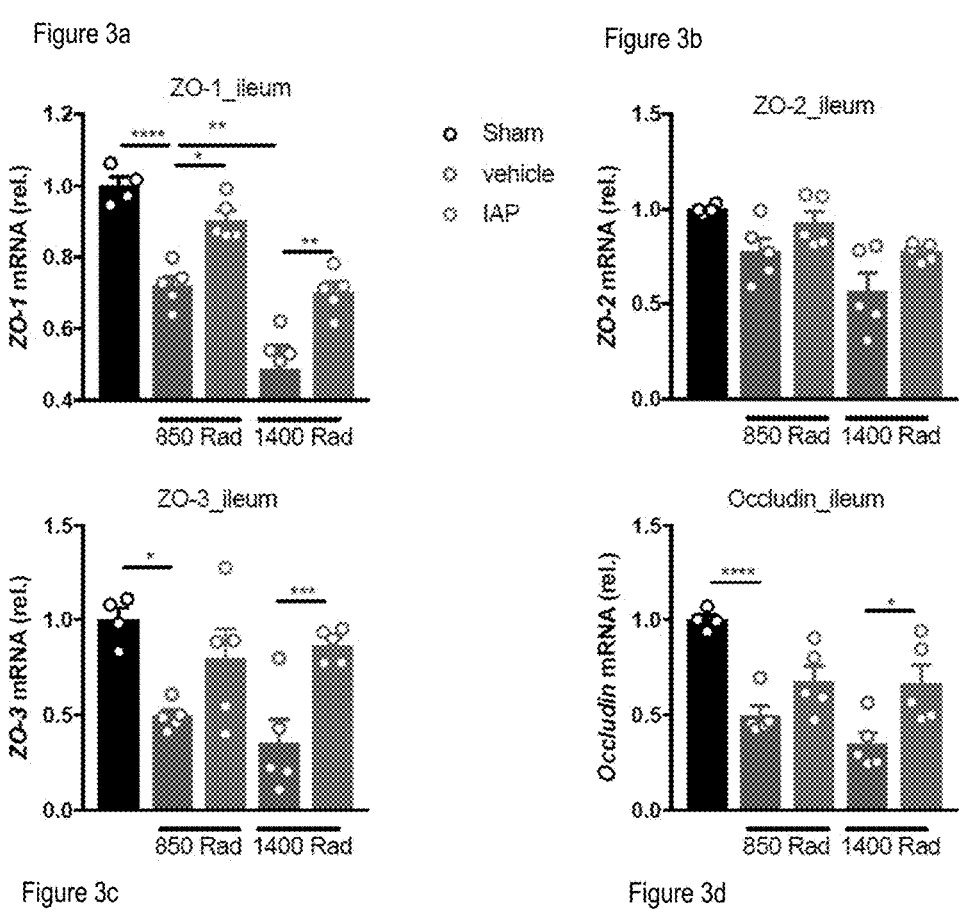
Figure 3c                          Figure 3d

Radiation-induced gut hyperpermeability (Colon)

Radiation-induced gut inflammation

IL1B_colon

TNF_colon

Radiation-induced gut inflammation Ileum

IAP expression decreases after radiation
Duodenum

Figure 8a
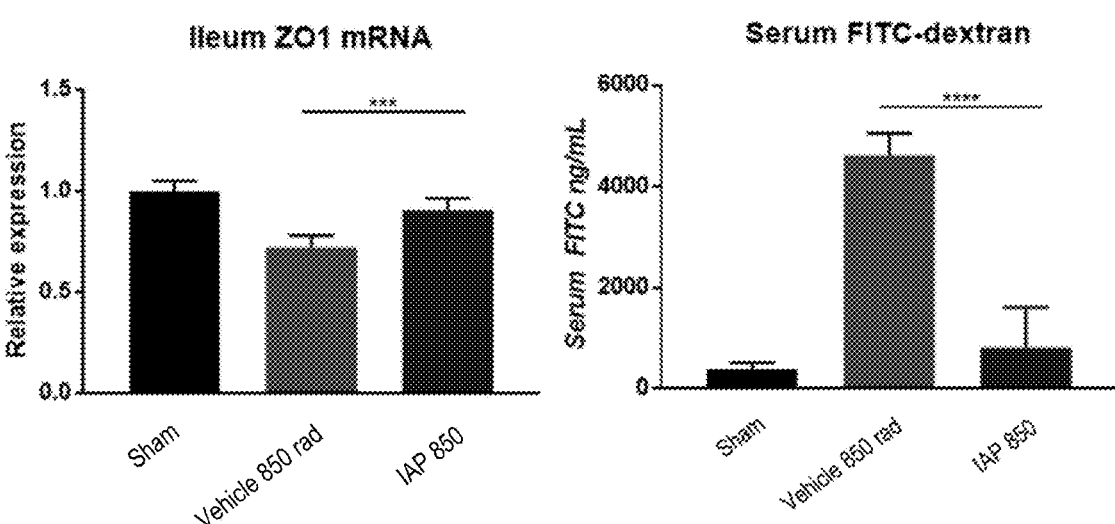
Figure 8b
Figure 8c
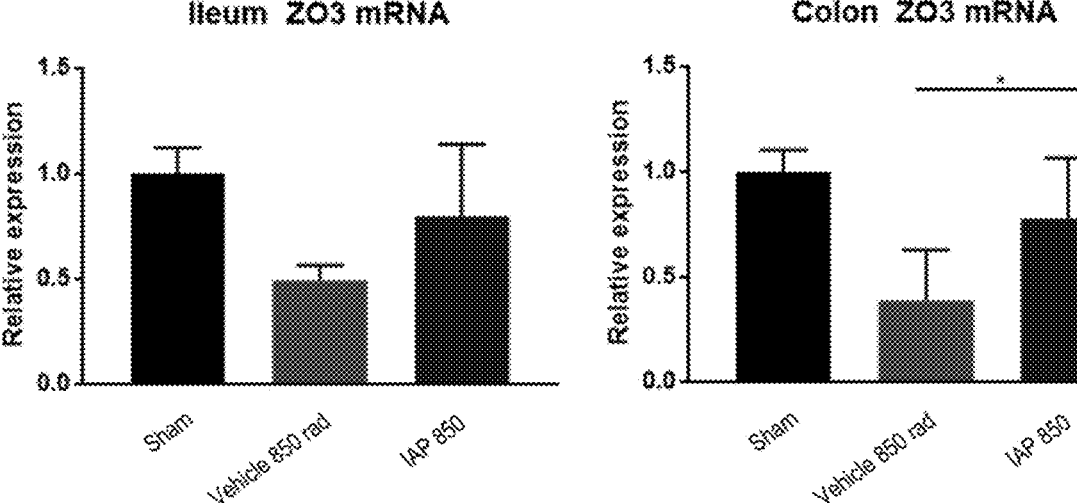
Figure 8d
Figure 8e
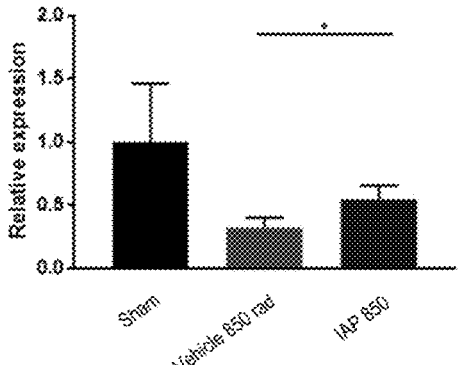

CONTROL            IRRADIATED            IRRADIATED + IAP

Figure 11a
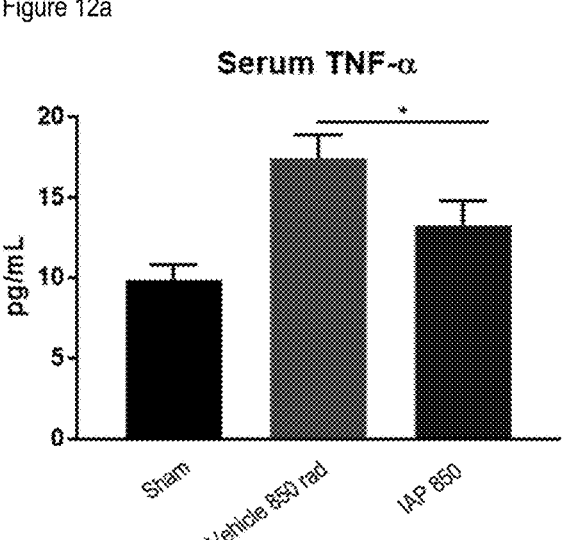
Figure 11b
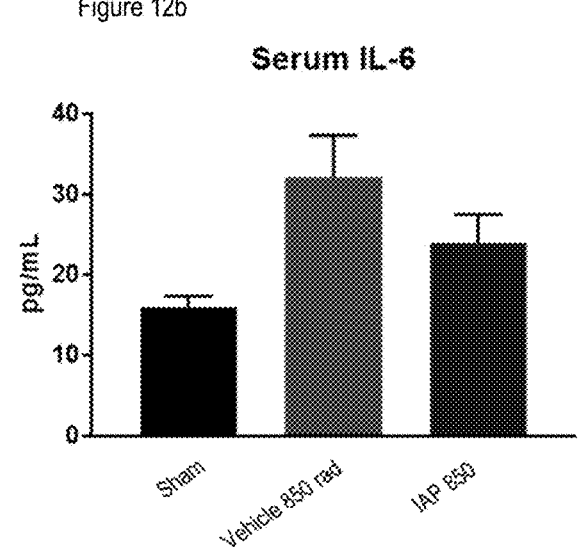
Figure 12a
Figure 12b

ALKALINE PHOSPHATASE AGENTS FOR TREATMENT OF RADIATION DISORDERS

CROSS-REFERENCE TO RELATED APPLICATIONS

This application is a continuation of U.S. patent application Ser. No. 16/982,211, filed Sep. 19, 2020 (now U.S. Pat. No. 11,654,184), which claims the benefit of U.S. Provisional Application Nos. 62/645,469, filed Mar. 20, 2018, and 62/714,398, filed Aug. 3, 2018, the entire contents of which are hereby incorporated by reference in their entirety.

TECHNICAL FIELD

The present invention relates, inter alia, to therapeutic alkaline phosphatases. The present invention further relates to compositions comprising the therapeutic alkaline phosphatases and use of the compositions in the treatment or prevention of radiation disorders.

DESCRIPTION OF THE SEQUENCE FILE SUBMITTED ELECTRONICALLY

The instant application contains a Sequence Listing which has been submitted electronically in XML file format and is hereby incorporated by reference in its entirety. Said XML file, created on Apr. 14, 2023, is named "SYN-036C1_112492-5036_Sequence_Listing.xml" and is 91,393 bytes in size.

BACKGROUND

Alkaline phosphatase ("APs," EC 3.1.3.1) is a hydrolase enzyme that can remove phosphate groups from various targets including nucleotides and proteins. Alkaline phosphatases are found in prokaryotic as well as eukaryotic organisms ranging from *E. coli* to mammals. In particular, mammalian APs have been shown to play important roles in gut homeostasis, mucosal barrier function, promotion of commensal bacteria, and defense from pathogens. Mammalian APs exert their properties by primarily targeting LPS (a TLR4 agonist), flagellin (a TLR5 agonist) and CpG DNA (a TLR9 agonist). APs also degrade intestine luminal NTPs (e.g., ATP, GTP, etc.), which promote the growth of good bacteria and reverses dysbiosis.

Radiation has been linked to dysbiosis. With an increasing risk of nuclear and radiological emergencies, there is a critical need for development of medical radiation countermeasures (MRC) which are safe, easily administered and effective in preventing and/or mitigating the potentially lethal tissue damage caused by radiation exposure, especially high-dose radiation exposure (e.g. acute radiation syndrome (ARS)). There are currently no FDA approved MRCs. Further, radiation finds use in the treatment of various diseases, such as cancers. This therapy may cause extremely deleterious side effects. Such side effects are similarly observed with certain chemotherapies. In addition, with the increasing number of cancer survivors who underwent radiation treatment, there is also a need for therapies that target radiation enteropathy that can develop after radiation treatments end. In particular, delayed (chronic) intestinal radiation toxicity manifests into some form of GI dysfunction, and symptoms might not present until after a latency period of 6 months to 3 years.

There remains a need for novel and improved AP-based therapeutic compositions for the prevention and treatment of radiation-related diseases.

SUMMARY

Accordingly, in some aspects, the present invention provides various AP constructs ("AP-based agents") and therapeutic uses thereof. In various embodiments, the AP-based agent is a mammalian or bacterial alkaline phosphatase. In some embodiments, the AP-based agent is a mammalian alkaline phosphatase. In an embodiment, the AP-based agent is an intestinal alkaline phosphatase. In some embodiments, the AP-based agent is a bacterial alkaline phosphatase. In some embodiments, the bacterial alkaline phosphatase has catalytic activity comparable to that of a mammalian phosphatase. In some embodiments, the AP-based agent is secreted from the host cell.

In some aspects, the present invention provides methods for the therapeutic use of an AP-based agent. In an embodiment, the present invention provides methods for the treatment or prevention of various radiation-related disorders. For instance, in various embodiments, the present invention provides methods for the treatment or prevention of ARS. In various embodiments, the present invention provides methods for the treatment or prevention of side effects related to radiation treatment (radiotherapy). In various embodiments, the present invention provides methods for the treatment or prevention of side effects related to chemotherapeutic treatment. An aspect of the present invention provides methods of the treatment or prevention of delayed radiation enteropathy.

Accordingly, the present invention further relates to treatment and/or prevention of chronic radiation-induced enteropathy, colitis, and/or proctitis. AP-based agents, including IAP, may be administered to patients prior to and/or at the time of exposure to radiation. In some embodiments, patients may receive administration of AP-based agents after exposure to radiation. In various embodiments, AP-based administration to patients in need thereof occurs when symptoms present (e.g., from about 3 months to about 12 months) after exposure to radiation.

BRIEF DESCRIPTION OF THE DRAWINGS

FIG. 3a-3d depicts gene expression of ZO-1 (FIG. 3a), ZO-2 (FIG. 3b), ZO-3 (FIG. 3c), and occludin (FIG. 3d) in the ileums of irradiated mice (both 850 and 1400 rads) and irradiated mice that received vehicle. In all panels, the left-most bar represents the sham data; the left bar within the 850 rad cohort represents vehicle data, while the right bar represents IAP data; and the left bar within the 1400 rad cohort represents vehicle data, while the right bar represents IAP data.

FIG. 8a-8e depicts analysis of the gut barrier of irradiated mice by measuring the flux of 4 kDa FITC-Dextran across the epithelium into the bloodstream to determine serum FITC (FIG. 8a). FIG. 8b and FIG. 8c show that IAP supplementation restored ZO1 expression to 90% of control (p<0.001) and partially restored ZO3. As shown in FIG. 8d and FIG. 8e, ZO3 and occludin expression were increased from 28% to 47% of control (P<0.05) and 39% to 78% of control (p<0.05) respectively.

FIG. 10a shows that irradiated mice had a 13-fold increase in TNF-α which was reduced 50% by IAP supplementation (p<0.001). Similarly, irradiated mice had a 6-fold increase in IL-6 levels (FIG. 10b), a 4.5-fold increase in IL-1β, and a 2.8-fold increase in IL-17 (FIG. 10c).

FIG. 11a-11b depicts inflammatory cytokine expression in the colon of irradiated mice. FIG. 11a-b shows that irradiation treatment increased TNF-α expression 15-fold (FIG. 11a) and IL-1p 8-fold (FIG. 11b), enteral IAP similarly reduced expression of these cytokines by 80% and 75%, respectively (p<0.05).

FIG. 12a-12b depicts circulating cytokine levels. Irradiated mice had significantly higher systemic levels of both TNF-α (FIG. 12a) and IL-6 (FIG. 12b) in the serum (p<0.05).

DETAILED DESCRIPTION

Figure 1:
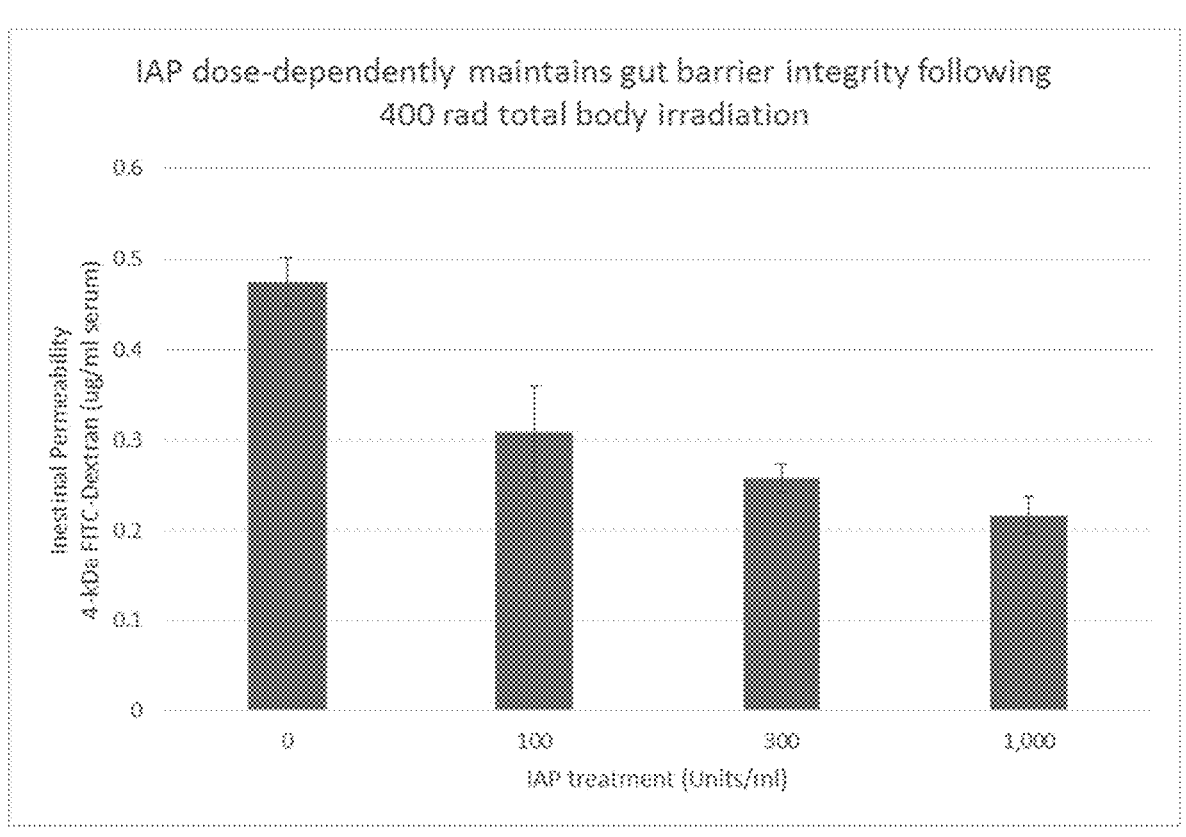
FIG. 1 depicts the results of an in vivo study using FITC-dextran as a marker to show that administration of intestinal alkaline phosphatase (IAP) significantly diminished gut leakage and intestinal epithelial permeability due to radiation exposure in a dose-dependent manner.

The present invention is based, in part, on the discovery that AP-based agents can practically be used in a number of radiation- or chemotherapeutic-related diseases or disorders. For instance, radiation exposure and/or or chemotherapeutic exposure may lead to GI tract disruption, including, without limitation, dysbiosis, leaky gut, endotoxemia, altered intestinal transit, malabsorption, and dysmotility, and the present AP-based agents, including without limitation intestinal alkaline phosphatase (IAP), optionally orally administered, may reduce or prevent such. Accordingly, the present invention relates, in various embodiments, to the treatment or prevention of the effects of radiation and/or chemotherapy with the present AP-based agents, including without limitation intestinal alkaline phosphatase (IAP), optionally orally administered.

In various embodiments, the present invention provides methods of treating or preventing radiation-induced enteropathy, colitis, and/or proctitis. Radiation-induced enteropathy is characterized by mucosal atrophy, vascular sclerosis, and progressive intestinal wall fibrosis. Symptoms of the disorder can include malabsorption of nutrients, altered intestinal transit, dysmotility, and abnormal propulsion of intestinal contents. In some embodiments, acute radiation-induced enteropathy occurs within the first month, first 2 months, or first 3 months after radiation exposure. In some embodiments, delayed radiation enteropathy symptoms are chronic and may not present until at least 3, at least 4, at least 5, at least 6, at least 7, at least 8, at least 9, at least 10, at least 11, or at least 12 months after radiation exposure. In some embodiments, delayed radiation enteropathy symptoms may not present until about 3, about 4, about 5, about 6, about 7, about 8, about 9, about 10, about 11, or about 12 months after radiation exposure. In some embodiments, delayed radiation enteropathy symptoms may not present until about 1 year, about 2 years, about 3 years, about 4 years, or about 5 years after radiation exposure.

In various embodiments, administration of the AP-based agent occurs prior to exposure to radiation, such as, for example, prior to radiotherapy as part of a cancer treatment. In certain embodiments, administration of the AP-based agent occurs at the time of radiation exposure. In various embodiments, administration of the AP-based agent occurs at the time of exposure to radiation, as well as shortly after exposure to radiation. In some embodiments, administration of the AP-based agent occurs shortly after exposure to radiation. In various embodiments, administration of the AP-based agent occurs at the time of exposure to radiation, as well as continued long term after exposure to radiation. In some embodiments, administration of the AP-based agent continues for a long term after exposure to radiation. In various embodiments, administration of the AP-based agent occurs at the onset of delayed radiation enteropathy. In some embodiments, the present invention provides for the treatment and/or administration of an AP-based agent to a subject that has been exposed to or will be exposed to radiation, where the administration of the AP-based agent occurs for at least 1 year, at least 1.5 years, at least 2 years, at least 2.5 years, at least 3 years, at least 3.5 years, 4 years, at least 4.5 years, at least 5 years, at least 5.5 years, at least 6 years, at least 6.5 years, or at least 7 years after the exposure to radiation.

In some embodiments, the present methods pertain to prevention or reduction of reduced diversity in the gut microbiome, e.g. that is a side effect or result of radiation exposure (including radiotherapy) and/or chemotherapy. In some embodiments, the present methods relate to repairing and/or repopulating the gut microbiome of a subject after radiation exposure (including radiotherapy) and/or chemotherapy.

In some embodiments the present methods result in a patient presenting a reduction in serum FITC. For example, the patient may present an at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% reduction in serum FITC. In further embodiments, the patient presents from 20%-90%, 30%-90%, 40%-90%, 50%-90%, 60%-90%, 70%-90%, or 80%-90% reduction in serum FITC. In some embodiments, the present methods result in a patient presenting a decreased degree of injury to the ileal tissue. In some embodiments, the degree of injury is based on a severity score ranging from 0 to 3. In some embodiments the present methods result in a patient presenting a reduction in the expression of inflammatory cytokines. For example, the patient may present at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% reduced expression of inflammatory cytokines. In further embodiments, the patient presents from 20%-90%, 30%-90%, 40%-90%, 50%-90%, 60%-90%, 70%-90%, or 80%-90% reduction in inflammatory cytokines. In further emboln various embodiments, the inflammatory cytokines are selected from TNF-α, IL-1β, IL-6, and IL-17. In some embodiments the present methods result in a patient presenting restored expression of endogenous IAP. For example, the patient may present at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% restored endogenous IAP expression. In further embodiments, the patient presents from 20%-90%, 30%-90%, 40%-90%, 50%-90%, 60%-90%, 70%-90%, or 80%-90% restored expression of endogenous IAP.

Alkaline Phosphatase-Based Agents and Pharmaceutical Compositions

The present invention is directed, in part, to pharmaceutical compositions, formulations, and uses of one or more alkaline phosphatase-based agents (AP-based agents). Alkaline phosphatases are dimeric metalloenzymes that catalyze the hydrolysis of phosphate esters and dephosphorylate a variety of target substrates at physiological and higher pHs. Alkaline phosphatases are found in prokaryotic as well as in eukaryotic organisms (e.g., in *E. coli* and mammals). Illustrative AP-based agents that may be utilized in the present invention include, but are not limited to, IAP (e.g., calf IAP or bovine IAP, chicken IAP, goat IAP), placental alkaline phosphatase (PLAP), placental-like alkaline phosphatase, germ cell alkaline phosphatase (GCAP), tissue non-specific alkaline phosphatase (TNAP; which is primarily found in the liver, kidney, and bone), bone alkaline phosphatase, liver alkaline phosphatase, kidney alkaline phosphatase, bacterial alkaline phosphatase, fungal alkaline phosphatase, shrimp alkaline phosphatase, modified IAP, recombinant IAP, or any polypeptide comprising alkaline phosphatase activity.

In various embodiments, the present invention contemplates the use of mammalian alkaline phosphatases including, but are not limited to, intestinal alkaline phosphatase (IAP), placental alkaline phosphatase (PLAP), germ cell alkaline phosphatase (GCAP), and the tissue non-specific alkaline phosphatase (TNAP).

In some embodiments, the AP-based agent is IAP. IAP is produced in the proximal small intestine and it bound to the enterocytes via a GPI anchor. Some IAP is released into the intestinal lumen in conjunction with vesicles shed by the cells and as soluble protein stripped from the cells via phospholipases. The enzyme then traverses the small and large intestine such that some active enzyme can be detected in the feces. In an embodiment, the IAP is human IAP (hIAP). In an embodiment, the IAP is calf IAP (cIAP), also known as bovine IAP (bIAP). There are multiple isozymes of bIAP, for example, with bIAP II and IV having higher specific activity than bIAP I. In an embodiment, the IAP is any one of the cIAP or bIAP isozymes (e.g., bIAP I, II, and IV). In an embodiment, the IAP is bIAP II. In another embodiment, the IAP is bIAP IV.

In various embodiments, the AP-based agent is hIAP or a variant thereof. In some embodiments, the AP-based agent is hIAP comprising the amino acid sequence of SEQ ID NO: 1 as depicted below.

```
HIAP -
                                               SEQ ID NO: 1
  1  mqgpwvllll  glrlqlslgv  ipaeeenpaf  wnrqaaeald  aakklqpiqk  vaknlilflg 61  dglgvptvta  trilkgqkng  klgpetplam  drfpylalsk  tynvdrqvpd  saatataylc 121  gvkanfqtig  lsaaarfnqc  nttrgnevis  vmnrakqagk  svgvvtttrv  qhaspagtya 181  htvnrnwysd  admpasarqe  gcqdiatqli  snmdidvilg  ggrkymfpmg  tpdpeypada 241  sqngirldgk  nlvqewlakh  qgawyvwnrt  elmqasldqs  vthlmglfep  gdtkyeihrd 301  ptldpslmem  teaalrllsr  nprgfylfve  ggridhghhe  gvayqaltea  vmfddaiera 361  gqltseedtl  tlvtadhshv  fsfggytlrg  ssifglapsk  aqdskaytsi  lygngpgyvf 421  nsgvrpdvne  sesgspdyqq  qaavplsset  hggedvavfa  rgpqahlvhg  vqeqsfvahv 481  mafaaclepy  tacdlappac  ttdaahpvaa  slpllagtll  llgasaap
```

Without wishing to be bound by theory, it is believed that a cysteine at the carboxy terminus of the AP-based agent (e.g., at position 500 of SEQ ID NO: 1) may interfere with protein folding. Accordingly, in some embodiments, the AP-based agent includes a mutation of the cysteine (e.g., at position 500 of SEQ ID NO: 1). In some embodiments, the cysteine is replaced with glycine.

In various embodiments, the AP-based agent is bIAP II or a variant thereof. In an embodiment, the bIAP II comprises the signal peptide and carboxy terminus of bIAP I. In an embodiment, the bIAP II comprises an aspartate and position 248 (similar to bIAP IV). In an embodiment, the bIAP II comprises the amino acid sequence of SEQ ID NO: 2:

omega +1, and omega +2 which are followed by a short stretch of hydrophilic amino acids and then a stretch of hydrophobic amino acids. Without wishing to be bound by theory, it is believed that the hydrophobicity is critical for embedding the carboxy terminus in the ER membrane. Then an enzymatic reaction replaces the carboxy terminus with the GPI anchor.

Within hPLAP, the GPI anchor is attached at an aspartate in the sequence, DAAH. Similarly hIAP, bIAP II, and bIAP IV also have this DAAH sequence conserved, potentially serving as the GPI anchor site. Mutational studies with hPLA indicate that preventing GPI anchoring results in intracellular retention. In addition, mutations around the

```
BIAP II with 248D assignment - The signal peptide and sequence past 480
are derived from bIAP I
                                              SEQ ID NO: 2
  1   mqgacvllll glhlqlslgl ipaeeenpaf wnrqaaqald vakklqpiqt aaknvilflg 61   dgmgvptvta trilkgqmng klgpetplam dqfpyvalsk tynvdrqvpd sagtataylc 121   gvkgnyrtig vsaaarynqc nttrgnevts vinrakkagk avgvvtttrv qhaspagaya 181   htvnrnwysd adlpadaqkn gcqdiaaqlv ynmdidvilg ggrmymfpeg tpdpeypdda 241   svngvrkdkq nlvqewqakh qgaqyvwnrt allqaaddss vthlmglfep admkynvqqd 301   htkdptlaem teaalqvlsr nprgfylfve ggridhghhd gkaymaltea imfdnaiaka 361   neltseldtl ilvtadhshv fsfggytlrg tsifglapgk aldsksytsi lygngpgyal 421   gggsrpdvng stseepsyrq qaavplaset hggedvavfa rgpqahlvhg vqeetfvahi 481   mafagcvepy tdcnlpapat atsipdaahl aasppplall agamllllap tly.
```

In various embodiments, the AP-based agent is bIAP IV or a variant thereof. In an embodiment, the bIAP IV comprises the amino acid sequence of SEQ ID NO: 3:

anchor site or in the hydrophobic domain either 1) prevent anchor attachment leading to intracellular retention or 2) do not block anchor attachment. Without wishing to be bound

```
BIAP IV -
                                              SEQ ID NO: 3
  1   mqwacvllll glwlqlsltf ipaeeedpaf wnrqaaqald vakklqpiqt aaknvilflg 61   dgmgyptvta trilkgqmng klgpetplam dqfpyvalsk tynydrqvpd sagtataylc 121   gvkgnyktig vsaaarynqc nttsgnevts vmnrakkagk svgyyttsrv qhaspagaya 181   htvnrnwysd adlpadaqty gcqdiatqlv nnmdidvilg ggrmymfpeg tpdpeypydv 241   nqtgyrkdkr nlvqewqakh qgaqyvwnrt ellqaandps vthlmglfep admkynvqqd 301   ptkdptleem teaalqvlsr npqgfylfve ggridhghhe gkaymaltdt vmfdnaiaka 361   neltseldtl ilatadhshv fsfggytlrg tsifglapsk asdnksytsi lygngpgyvl 421   ggglrpdynd sisedpsyrq qaavplsses hggedvavfa rgpqahlvhg vqeetfvahv 481   mafagcvepy tdcnlpapsg lsdaahlaas ppslallaga mllllapaly
```

Mammalian alkaline phosphatases are glycosylphosphatidyl-inositol (GPI) anchored proteins. They have signal peptides and are translated into the secretory pathway. Once in the endoplasmic reticulum (ER), the proteins are glycosylated and folded. There are two disulfide bonds as well as a single free cysteine that is apparently not accessible on the surface. In the late ER, the carboxy terminus is removed and the GPI anchor is appended. GPI anchoring is therefore a process that occurs at the carboxy terminus of the alkaline phosphatase. The inclusion of stop codons at the anchor site enables secretion of biologically active protein (presumably the homodimer). While there is no consensus sequence, the carboxy terminus includes three amino acids, termed omega, by theory, it is believed that the hydrophobic domain serves as a signal for GPI anchor attachment. Truncating or eliminating the hydrophobic domain leads to secretion. Finally, there is a single mutation in the hydrophobic domain that, in hPLAP, enables secretion of a protein with its hydrophobic domain intact.

In various embodiments, the AP-based agent of the invention is GPI anchored to a host cell. For example, the AP-based agent may be GPI anchored to the cell membrane of the host cell. In other embodiments, the AP-based agent of the invention is a secreted rather than an anchored protein. In some embodiments, the AP-based agent is not GPI anchored. In some embodiments, the AP-based agent may lack the GPI anchor site. In some embodiments, the AP-based agent comprises a stop codon that is inserted immediately after the GPI anchor site. In an embodiment, the AP-based agent comprises a stop codon after the aspartate in the DAAH consensus site (e.g., at amino acid 503 of hIAP and bIAP IV or amino acid 506 of bIAP II).

```
HIAP with stop codon
                                                        (SEQ ID NO: 4)
     1    mqgpwvllll  glrlqlslgv  ipaeeenpaf  wnrqaaeald  aakklqpiqk  vaknlilflg 61    dglgvptvta  trilkgqkng  klgpetplam  drfpylalsk  tynvdrqvpd  saatataylc 121    gvkanfqtig  lsaaarfnqc  nttrgnevis  vmnrakqagk  svgvvtttrv  qhaspagtya 181    htvnrnwysd  admpasarqe  gcqdiatqli  snmdidvilg  ggrkymfpmg  tpdpeypada 241    sqngirldgk  nlvqewlakh  qgawyvwnrt  elmqasldqs  vthlmglfep  gdtkyeihrd 301    ptldpslmem  teaalrllsr  nprgfylfve  ggridhghhe  gvayqaltea  vmfddaiera 361    gqltseedtl  tlvtadhshv  fsfggytlrg  ssifglapsk  aqdskaytsi  lygngpgyvf 421    nsgvrpdvne  sesgspdyqq  qaavplsset  hggedvavfa  rgpqahlvhg  vqeqsfvahv 481    mafaaclepy  tacdlappag  ttd BIAP II with stop codon
                                                        (SEQ ID NO: 5)
     1    mqgacvllll  glhlqlslgl  ipaeeenpaf  wnrqaaqald  vakklqpiqt  aaknvilflg 61    dgmgvptvta  trilkgqmng  klgpetplam  dqfpyvalsk  tynvdrqvpd  sagtataylc 121    gvkgnyrtig  vsaaarynqc  nttrgnevts  vinrakkagk  avgvvtttrv  qhaspagaya 181    htvnrnwysd  adlpadaqkn  gcqdiaaqlv  ynmdidvilg  ggrmymfpeg  tpdpeypdda 241    svngvrkdkq  nlvqewqakh  qgagyvwnrt  allqaaddss  vthlmglfep  admkynvqqd 301    htkdptlaem  teaalqvlsr  nprgfylfve  ggridhghhd  gkaymaltea  imfdnaiaka 361    neltseldtl  ilvtadhshv  fsfggytlrg  tsifglapgk  aldsksytsi  lygngpgyal 421    gggsrpdvng  stseepsyrq  qaavplaset  hggedvavfa  rgpqahlvhg  vqeetfvahi 481    mafagcvepy  tdcnlpapat  atsipd BIAP IV with stop codon
                                                        (SEQ ID NO: 6)
     1    mqwacvllll  glwlqlsltf  ipaeeedpaf  wnrqaaqald  vakklqpiqt  aaknvilflg 61    dgmgvptvta  trilkgqmng  klgpetplam  dqfpyvalsk  tynvdrqvpd  sagtataylc 121    gvkgnyktig  vsaaarynqc  nttsgnevts  vmnrakkagk  svgvvttsrv  qhaspagaya 181    htvnrnwysd  adlpadaqty  gcqdiatqlv  nnmdidvilg  ggrmymfpeg  tpdpeypydv 241    nqtgvrkdkr  nlvqewqakh  qgaqyvwnrt  ellqaandps  vthlmglfep  admkynvqqd 301    ptkdptleem  teaalqvlsr  npqgfylfve  ggridhghhe  gkaymaltdt  vmfdnaiaka 361    neltseldtl  ilatadhshv  fsfggytlrg  tsifglapsk  asdnksytsi  lygngpgyvl 421    ggglrpdvnd  sisedpsyrq  qaavplsses  hggedvavfa  rgpqahlvhg  vqeetfvahv 481    mafagcvepy  tdcnlpapsg  lsd
```

In an embodiment, the AP-based agent is bIAP IV and includes a stop codon after amino acid 508 to mimic a secreted PLAP construct as depicted below:

```
BIAP IV with stop codon after amino acid 508
                                                        (SEQ ID NO: 7)
     1    mqwacvllll  glwlqlsltf  ipaeeedpaf  wnrqaaqald  vakklqpiqt  aaknvilflg 61    dgmgvptvta  trilkgqmng  klgpetplam  dqfpyvalsk  tynvdrqvpd  sagtataylc 121    gvkgnyktig  vsaaarynqc  nttsgnevts  vmnrakkagk  svgvvttsrv  qhaspagaya 181    htvnrnwysd  adlpadaqty  gcqdiatqlv  nnmdidvilg  ggrmymfpeg  tpdpeypydv
```

-continued

```
241  nqtgvrkdkr nlvqewqakh qgagyvwnrt ellqaandps vthlmglfep admkynvqqd 301  ptkdptleem teaalqvlsr npqgfylfve ggridhghhe gkaymaltdt vmfdnaiaka 361  neltseldtl ilatadhshv fsfggytlrg tsifglapsk asdnksytsi lygngpgyvl 421  ggglrpdvnd sisedpsyrq qaavplsses hggedvavfa rgpqahlvhg vqeetfvahv 481  mafagcvepy tdcnlpapsg lsdaahla
```

In various embodiments, the AP-based agent of the invention is a fusion protein. In some embodiments, the AP-based agent comprises an alkaline phosphatase fused to a protein domain that replaces the GPI anchor sequence. In some embodiments, the alkaline phosphatase is fused to a protein domain that promotes protein folding and/or protein purification and/or protein dimerization and/or protein stability. In various embodiments, the AP-based agent fusion protein has an extended serum half-life.

In an embodiment, the alkaline phosphatase is fused to an immunoglobulin Fc domain and/or hinge region. In various embodiments, the immunoglobulin Fc domain and/or hinge region is derived from the Fc domain and/or hinge region of an antibody (e.g., of IgG, IgA, IgD, and IgE, inclusive of subclasses (e.g. IgG1, IgG2, IgG3, and IgG4, and IgA1 and IgA2)). In an embodiment, the AP-based agent of the invention comprises an alkaline phosphatase fused to the hinge region and/or Fc domain of IgG.

In various embodiments, the AP-based agent is fused to a Fc domain of IgG comprising one or more mutations. In some embodiments, the one or more mutations in the Fc domain of IgG function to increase serum half-life and longevity. In some embodiments, the Fc domain of IgG comprises one or more mutations at amino acid residues 251-256, 285-290, 308-314, 385-389 and 428-436, numbered according to the EU index as in Kabat (see Kabat et al., (1991) Sequences of Proteins of Immunological Interest, U.S. Public Health Service, National Institutes of Health, Washington, DC). In some embodiments, at least one of the amino acid substitutions is at amino acid residue 252, 254, 256, 309, 311, 433 or 434. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain of IgG comprises one or more mutations at amino acid residue 252, 254, 256, 433, 434, or 436. In an embodiment, the Fc domain of IgG includes a triple M252Y/S254T/T256E mutation or YTE mutation. In another embodiment, the Fc domain of IgG includes a triple H433K/N434F/Y436H mutation or KFH mutation. In a further embodiment, the Fc domain of IgG includes a YTE and KFH mutation in combination.

In some embodiments, the Fc domain of IgG contains one or more mutations at amino acid residues 250, 253, 307, 310, 380, 428, 433, 434, and 435. Exemplary mutations include T250Q, M428L, T307A, E380A, I253A, H310A, M428L, H433K, N434A, N434F, N434S, and H435A. In an embodiment, the Fc domain of IgG comprises a M428L/N434S mutation or LS mutation. In another embodiment, the Fc domain of IgG comprises a T250Q/M428L mutation or QL mutation. In another embodiment, the Fc domain of IgG comprises an N434A mutation. In another embodiment, the Fc domain of IgG comprises a T307A/E380A/N434A mutation or AAA mutation. In another embodiment, the Fc domain of IgG comprises an I253A/H310A/H435A mutation or IHH mutation. In another embodiment, the Fc domain of IgG comprises a H433K/N434F mutation. In another embodiment, the Fc domain of IgG region comprises a M252Y/S254T/T256E and a H433K/N434F mutation in combination.

Exemplary mutations in the Fc domain of IgG are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al. Nature (2014) 514:642-645, Grevys et al Journal of Immunology. (2015), 194(11):5497-508, and U.S. Pat. No. 7,083,784, the entire contents of which are hereby incorporated by reference.

In various embodiments, the one or more mutations in the Fc domain of IgG increases affinity for the neonatal Fc receptor (FcRn). In some embodiments, the one or more mutations in the Fc domain of IgG increases affinity for FcRn at a pH of about 6.0, about 6.1, about 6.2, about 6.3, about 6.4, or about 6.5.

In various embodiments, the alkaline phosphatase is fused to one or more of PEG, XTENylation (e.g., as rPEG), polysialic acid (POLYXEN), albumin, elastin-like protein, elastin like protein (ELP), PAS, HAP, GLK, CTP, and transferrin. In various embodiments, the alkaline phosphatase is fused to one or more of the agents described in BioDrugs (2015) 29:215-239, the entire contents of which are hereby incorporated by reference.

In an embodiment, the alkaline phosphatase is fused to a protein domain (e.g., an immunoglobulin Fc domain) via a linker to the GPI anchor site. For example, the alkaline phosphatase may be fused to a protein domain via the aspartate at the GPI anchor sequence. The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present AP-based agent. In another example, the linker may function to target the AP-based agent to a particular cell type or location.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). In an embodiment, the linker sequence is GGSGGSGGGGSGGGGS (SEQ ID NO: 41). Additional illustrative linkers include, but are not limited to, linkers having the sequence LE, GGGGS (SEQ ID NO: 42), (GGGGS), (n=2-4) (SEQ ID NO: 43-45), (Gly)$_8$(SEQ ID NO: 46), (Gly)$_6$ (SEQ ID NO: 47), (EAAAK), (n=1-3) (SEQ ID NO: 48-50), A(EAAAK),A (n=2-5) (SEQ ID NO: 51-54), AEAAAKEAAAKA (SEQ ID NO: 55), A(EAAAK)$_4$ALEA(EAAAK)$_4$A (SEQ ID NO: 56), PAPAP (SEQ ID NO: 57), KESGSVSSEQLAQFRSLD (SEQ ID NO: 58), EGKSSGSGSESKST (SEQ ID NO: 59), GSAGSAAGSGEF (SEQ ID NO: 60), and (XP), with X designating any amino acid, e.g., Ala, Lys, or Glu. In various embodiments, the linker is GGS.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites.

In some embodiments, the linker is a synthetic linker such as PEG.

Illustrative Fc fusion constructs of the invention include:

```
BIAP II with Fc Fusion - domain is underlined
                                                        (SEQ ID NO: 8)
  1    mqgacvllll glhlqlslgl ipaeeenpaf wnrqaaqald vakklqpiqt aaknvilflg 61    dgmgvptvta trilkgqmng klgpetplam dqfpyvalsk tynvdrqvpd sagtataylc 121    gvkgnyrtig vsaaarynqc nttrgnevts vinrakkagk avgvvtttrv qhaspagaya 181    htvnrnwysd adlpadaqkn gcgdiaaglv ynmdidvilg ggrmymfpeg tpdpeypdda
```

-continued

```
241    svngvrkdkq nlvqewqakh qgagyvwnrt allqaaddss vthlmglfep admkynvqqd 301    htkdptlaem teaalqvlsr nprgfylfve ggridhghhd gkaymaltea imfdnaiaka 361    neltseldtl ilvtadhshv fsfggytlrg tsifglapgk aldsksytsi lygngpgyal 421    gggsrpdvng stseepsyrq qaavplaset hggedvavfa rgpqahlvhg vqeetfvahi 481    mafagcvepy tdcnlpapat atsipdGGSGGSGGGGSGGGGSEPKSCDKTHTCPPCPAPE

LLGGPSVFLFPPKPKDTLMI SRTPEVTCVVVDVSHEDPQV KFNWYVDGVQVHNAKTKPRE

QQYNSTYRVVSVLTVLHQNW LDGKEYKCKVSNKALPAPIE KTISKAKGQPREPQVYTLPP

SREEMTKNQVSLTCLVKGFY PSDIAVEWESNGQPENNYKT TPPVLDSDGSFFLYSKLTVD

KSRWQQGNVFSCSVMHEALH NHYTQKSLSLSPGK
```

BIAP IV with Fc Fusion - domain is underlined (SEQ ID NO: 9)
```
  1    mqwacvllll glwlqlsltf ipaeeedpaf wnrqaaqald vakklqpiqt aaknvilflg 61    dgmgvptvta trilkgqmng klgpetplam dqfpyvalsk tynvdrqvpd sagtatarylc 121    gvkgnyktig vsaaaarynqc nttsgnevts vmnrakkagk svgvvttsrv qhaspagaya 181    htvnrnwysd adlpadaqty gcqdiatqlv nnmdidvilg ggrmymfpeg tpdpeypydv 241    nqtgvrkdkr nlvqewqakh qgagyvwnrt ellqaandps vthlmglfep admkynvqqd 301    ptkdptleem teaalqvlsr npqgfylfve ggridhghhe gkaymaltdt vmfdnaiaka 361    neltseldtl ilatadhshv fsfggytlrg tsifglapsk asdnksytsi lygngpgyvl 421    ggglrpdvnd sisedpsyrq qaavplsses hggedvavfa rgpqahlvhg vqeetfvahv 481    mafagcvepy tdcnlpapsg IsdGGSGGSGGGGSGGGGSEPKSCDKTHTCPPCPAPE

LLGGPSVFLFPPKPKDTLMI SRTPEVTCVVVDVSHEDPQV KFNWYVDGVQVHNAKTKPRE

QQYNSTYRVVSVLTVLHQNW LDGKEYKCKVSNKALPAPIE KTISKAKGQPREPQVYTLPP

SREEMTKNQVSLTCLVKGFY PSDIAVEWESNGQPENNYKT TPPVLDSDGSFFLYSKLTVD

KSRWQQGNVFSCSVMHEALH NHYTQKSLSLSPGK
```

HIAP with Fc Fusion - Fc domain is underlined:

SEQ ID NO: 18
```
  1    mqgpwvllll glrlqlslgv ipaeeenpaf wnrqaaeald aakklqpiqk vaknlilflg 61    dglgvptvta trilkgqkng klgpetplam drfpylalsk tynvdrqvpd saatataylc 121    gvkanfqtig lsaaaarfnqc nttrgnevis vmnrakqagk svgvvtttrv qhaspagtya 181    htvnrnwysd admpasarqe gcqdiatqli snmdidvilg ggrkymfpmg tpdpeypada 241    sqngirldgk nlvqewlakh qgawyvwnrt elmgasldqs vthlmglfep gdtkyeihrd 301    ptldpslmem teaalrllsr nprgfylfve ggridhghhe gvayqaltea vmfddaiera 361    gqltseedtl tlvtadhshv fsfggytlrg ssifglapsk aqdskaytsi lygngpgyvf 421    nsgvrpdvne sesgspdygq qaavpIsset hggedvavfa rgpqahlvhg vqeqsfvahv 481    mafaaclepy tacdlappac ttdaahpvaa slpllagtll llgasaap

GGSGGSGGGGSGGGGSEPKSCDKTHTCPPCPAPE LLGGPSVFLFPPKPKDTLMI

SRTPEVTCVVVDVSHEDPQV KFNWYVDGVQVHNAKTKPRE QQYNSTYRVVSVLTVLHQNW

LDGKEYKCKVSNKALPAPIE KTISKAKGQPREPQVYTLPP SREEMTKNQVSLTCLVKGFY

PSDIAVEWESNGQPENNYKT TPPVLDSDGSFFLYSKLTVD KSRWQQGNVFSCSVMHEALH

NHYTQKSLSLSPGK
```

In various embodiments, the linker can be substituted with any other linker disclosed herein.

A *Saccharomyces* alkaline phosphatase, Pho8, is produced as an inactive pro-enzyme. It is not GPI anchored, but is a transmembrane protein with its amino terminus extending out of a lysosome into the cytoplasm. Within the lysosome, an enzyme, PEP4, cleaves the carboxy terminus to activate the enzyme. Without wishing to be bound by theory, it is believed that mammalian alkaline phosphatases may also be generated as inactive pro-enzymes. This is because alkaline phosphatases can dephosphorylate ATP, so that activity in the ER could drain the ER of its major energy source. Without wishing to be bound by theory, it is believed that the inhibitory function is located to the carboxy terminus that would be relieved upon GPI anchor addition. Alternatively, other activities such as folding or metal (Zn or Mg) inclusion could control activity.

In various embodiments, the AP-based agent of the invention is a pro-enzyme. In an embodiment, the activity of the proenzyme is suppressed by a carboxy terminus. In an embodiment, protease removal of the carboxy terminus point mutation such as a substitution of leucine with e.g., arginine is generated in the hydrophobic carboxy terminus (e.g. allpllagtl is changed to e.g., allplragtl) to result in secretion of the enzyme without removal of the carboxy terminus.

In an embodiment, the AP-based agent is altered to include a specific enzyme cleavage site which allows subsequent removal of the carboxy terminus. In an embodiment, the AP-based agent includes a protease cleavage site. Illustrative protease cleavage sites include, but are not limited to, cleavage sites recognized by furin, Rhinovirus 16 3C protease, factor Xa protease, trpysin, chymotrypsin, elastase, pepsin, papain subtilisin, thermolysin, V-8 protease, submaxillaris protease, clostripain, thrombin, collagenase, and any other endoproteases. In an alternative embodiment, the AP-based agent includes a cleavage site recognized by a digestive enzyme present in the GI tract. In such embodiments, the AP-based agent may be administered as a pro-drug that is subsequently activated in the GI tract.

In an illustrative embodiment, the proenzyme is a proenzyme of bIAP IV having the following sequences:

```
BIAP IV with the hPLAP Carboxy Terminus and Mutation for Unprocessed
Secretion and RV3C Cleavage (at . . . LEVLFQGP . . . ):
                                                      SEQ ID NO: 10
     1    mqwacvllll glwlqlsltf ipaeeedpaf wnrqaaqald vakklqpiqt aaknvilflg 61    dgmgvptvta trilkgqmng klgpetplam dqfpyvalsk tynvdrqvpd sagtataylc 121    gvkgnyktig vsaaarynqc nttsgnevts vmnrakkagk svgvvttsrv qhaspagaya 181    htvnrnwysd adlpadaqty gcqdiatqlv nnmdidvilg ggrmymfpeg tpdpeypydv 241    nqtgvrkdkr nlvqewqakh qgagyvwnrt ellqaandps vthlmglfep admkynvqqd 301    ptkdptleem teaalqvlsr npqgfylfve ggridhghhe gkaymaltdt vmfdnaiaka 361    neltseldtl ilatadhshv fsfggytlrg tsifglapsk asdnksytsi lygngpgyvl 421    ggglrpdvnd sisedpsyrq qaavplsses hggedvavfa rgpqahlvhg vqeetfvahv 481    mafagcvepy tdcnlevlfq gpappagttd aahpgrsvvp allplragtl llletatap
```

```
BIAP IV with hPLAP Carboxy Terminus and Mutation for Unprocessed
Secretion and FXa Cleavage (at . . . IEGR . . . ):
                                                      SEQ ID NO: 11
     1    mwwacvllll glwlqlsltf ipaeeedpaf wnrqaaqald vakklqpiqt aaknvilflg 61    dgmgvptvta trilkgqmng klgpetplam dqfpyvalsk tynvdrqvpd sagtataylc 121    gvkgnyktig vsaaarynqc nttsgnevts vmnrakkagk svgvvttsrv qhaspagaya 181    htvnrnwysd adlpadaqty gcqdiatqlv nnmdidvilg ggrmymfpeg tpdpeypydv 241    nqtgvrkdkr nlvqewqakh qgagyvwnrt ellqaandps vthlmglfep admkynvqqd 301    ptkdptleem teaalqvlsr npqgfylfve ggridhghhe gkaymaltdt vmfdnaiaka 361    neltseldtl ilatadhshv fsfggytlrg tsifglapsk asdnksytsi lygngpgyvl 421    ggglrpdvnd sisedpsyrq qaavplsses hggedvavfa rgpqahlvhg vqeetfvahv 481    mafagcvepy tdcnlappag ttdaahpieg rsvvpallpl ragtllllet atap
``` reactivates the enzymatic activity of the alkaline phosphatase. In an embodiment, the pro-enzyme is more efficiently secreted than the enzyme without the carboxy terminus.

In some embodiments, for generation of the pro-enzyme, the native carboxy terminus of the alkaline phosphatase is replaced with the analogous sequence from hPLAP. In some embodiments, a mutation is made in the hydrophobic carboxy tail to promote protein secretion without cleavage of the carboxy terminus. In an illustrative embodiment, a single In various embodiments, the AP-based agent of the invention is efficiently expressed and secreted from a host cell. In an embodiment, the AP-based agent of the invention is efficiently transcribed in the host cell. In another embodiment, the AP-based agent exhibits enhanced RNA stability and/or transport in the host cell. In another embodiment, the AP-based agent is efficiently translated in the host cell. In a further embodiment, the AP-based agent is efficiently folded and/or transits efficiently through the ER, pre-golgi, and golgi. In another embodiment, the AP-based agent exhibits enhanced protein stability.

In various embodiments, the AP-based agent of the invention is GPI anchored to the cell membrane of a host cell. In other embodiments, the AP-based agent is secreted from the host cell. In such embodiments, the AP-based agent may include a protease cleavage site just upstream from the GPI anchor site. Illustrative protease cleavage sites are described previously. In an embodiment, the protease cleavage site is a furin cleavage site. In another embodiment, the AP-based agent may include a cleavage site recognized by a digestive enzyme in the GI tract just upstream from the GPI anchor site. In these embodiments, the AP-based agent is anchored in the ER and released in the late golgi and secreted.

In various embodiments, the AP-based agents are efficiently expressed in a host cell. In an embodiment, the Kozak sequence of the DNA construct encoding the AP-based agent is optimized. The Kozak sequence is the nucleotide sequence flanking the ATG start codon that instructs the ribosome to start translation. There is flexibility in the design of a Kozak sequence, but one canonical sequence is GCCGCCACCATGG. The purine in the −3 position and the G in the +4 position are the most important bases for translation initiation. For hIAP, bIAP II, and bIAP IV, the second amino acid, that is, the one after the initiator methionine, is glutamine. Codons for glutamine all have a C in the first position. Thus, their Kozak sequences all have an ATGC sequence. Accordingly, in various embodiments, the ATGC sequence is changed to ATGG. This can be achieved by changing the second amino acid to a glycine, alanine, valine, aspartate, or glutamic acid, all of whose codons have a G in the first position. These amino acids may be compatible with signal peptide function. In alternative embodiments, the entire signal peptide is substituted for peptide having a canonical Kozak sequence and is derived from a highly expressed protein such as an immunoglobulin.

In various embodiments, the signal peptide of the AP-based agent may be deleted and/or substituted. For example, the signal peptide may be deleted, mutated, and/or substituted (e.g., with another signal peptide) to ensure protein expression.

In some embodiments, The DNA construct encoding the AP-based agent of the invention comprises untranslated DNA sequences. Such sequences include an intron, which may be heterologous to the IAP protein or native to the IAP protein including the native first and/or second intron and/or a native 3' UTR. Without wishing to be bound by theory, it is believed that include of these sequences enhance protein expression by stabilizing the mRNA. Accordingly, in various embodiments, the DNA construct encoding the AP-based agent of the invention comprises the 5'UTR and/or the 3'UTR.

Provided below are illustrative IAP DNA sequences with a first intron and a 3'UTR:

```
hIAP with native first intron (shown as bolded and underlined) -
                                                    SEQ ID NO: 12
ATGCAGGGGCCCTGGGTGCTGCTGCTGCTGGGCCTGAGGCTACAGCTCTCCCTGGGCGTCA

TCCCAGGTAATGAGGCTCCCCAAGCTGTTCCACACACAGGGCACCCCCTCAGCCAGGCTGA

CCTGATCTCTACTCTCCCCCTGGCCAGCTGAGGAGGAGAACCCGGCCTTCTGGAACCGCCA

GGCAGCTGAGGCCCTGGATGCTGCCAAGAAGCTGCAGCCCATCCAGAAGGTCGCCAAGAAC

CTCATCCTCTTCCTGGGCGATGGGTTGGGGGTGCCCACGGTGACAGCCACCAGGATCCTAAA

GGGGCAGAAGAATGGCAAACTGGGGCCTGAGACGCCCCTGGCCATGGACCGCTTCCCATAC

CTGGCTCTGTCCAAGACATACAATGTGGACAGACAGGTGCCAGACAGCGCAGCCACAGCCAC

GGCCTACCTGTGCGGGGTCAAGGCCAACTTCCAGACCATCGGCTTGAGTGCAGCCGCCCGC

TTTAACCAGTGCAACACGACACGCGGCAATGAGGTCATCTCCGTGATGAACCGGGCCAAGCA

AGCAGGAAAGTCAGTAGGAGTGGTGACCACCACACGGGTGCAGCACGCCTCGCCAGCCGGC

ACCTACGCACACACAGTGAACCGCAACTGGTACTCAGATGCTGACATGCCTGCCTCAGCCCG

CCAGGAGGGGTGCCAGGACATCGCCACTCAGCTCATCTCCAACATGGACATTGACGTGATCC

TTGGCGGAGGCCGCAAGTACATGTTTCCCATGGGGACCCCAGACCCTGAGTACCCAGCTGAT

GCCAGCCAGAATGGAATCAGGCTGGACGGGAAGAACCTGGTGCAGGAATGGCTGGCAAAGC

ACCAGGGTGCCTGGTATGTGTGGAACCGCACTGAGCTCATGCAGGCGTCCCTGGACCAGTCT

GTGACCCATCTCATGGGCCTCTTTGAGCCCGGAGACACGAAATATGAGATCCACCGAGACCC

CACACTGGACCCCTCCCTGATGGAGATGACAGAGGCTGCCCTGCGCCTGCTGAGCAGGAAC

CCCCGCGGCTTCTACCTCTTTGTGGAGGGCGGCCGCATCGACCATGGTCATCATGAGGGTGT

GGCTTACCAGGCACTCACTGAGGCGGTCATGTTCGACGACGCCATTGAGAGGGCGGGCCAG

CTCACCAGCGAGGAGGACACGCTGACCCTCGTCACCGCTGACCACTCCCATGTCTTCTCCTT

TGGTGGCTACACCTTGCGAGGGAGCTCCATCTTCGGGTTGGCCCCCAGCAAGGCTCAGGAC

AGCAAAGCCTACACGTCCATCCTGTACGGCAATGGCCCGGGCTACGTGTTCAACTCAGGCGT
```

-continued

GCGACCAGACGTGAATGAGAGCGAGAGCGGGAGCCCCGATTACCAGCAGCAGGCGGCGGT

GCCCCTGTCGTCCGAGACCCACGGAGGCGAAGACGTGGCGGTGTTTGCGCGCGGCCCGCA

GGCGCACCTGGTGCATGGTGTGCAGGAGCAGAGCTTCGTAGCGCATGTCATGGCCTTCGCT

GCCTGTCTGGAGCCCTACACGGCCTGCGACCTGGCGCCTCCCGCCTGCACCACCGACGCCG

CGCACCCAGTTGCCGCGTCGCTGCCACTGCTGGCCGGGACCCTGCTGCTGCTGGGGGCGTC

CGCTGCTCCCTGA hIAP with native 3' UTR (shown as bolded and underlined) -
                                                              SEQ ID NO: 13
ATGCAGGGGCCCTGGGTGCTGCTGCTGCTGGGCCTGAGGCTACAGCTCTCCCTGGGCGTCA

TCCCAGCTGAGGAGGAGAACCCGGCCTTCTGGAACCGCCAGGCAGCTGAGGCCCTGGATGC

TGCCAAGAAGCTGCAGCCCATCCAGAAGGTCGCCAAGAACCTCATCCTCTTCCTGGGCGATG

GGTTGGGGGTGCCCACGGTGACAGCCACCAGGATCCTAAAGGGGCAGAAGAATGGCAAACT

GGGGCCTGAGACGCCCCTGGCCATGGACCGCTTCCCATACCTGGCTCTGTCCAAGACATACA

ATGTGGACAGACAGGTGCCAGACAGCGCAGCCACAGCCACGGCCTACCTGTGCGGGGTCAA

GGCCAACTTCCAGACCATCGGCTTGAGTGCAGCCGCCCGCTTTAACCAGTGCAACACGACAC

GCGGCAATGAGGTCATCTCCGTGATGAACCGGGCCAAGCAAGCAGGAAAGTCAGTAGGAGT

GGTGACCACCACACGGGTGCAGCACGCCTCGCCAGCCGGCACCTACGCACACACAGTGAAC

CGCAACTGGTACTCAGATGCTGACATGCCTGCCTCAGCCCGCCAGGAGGGGTGCCAGGACA

TCGCCACTCAGCTCATCTCCAACATGGACATTGACGTGATCCTTGGCGGAGGCCGCAAGTAC

ATGTTTCCCATGGGGACCCCAGACCCTGAGTACCCAGCTGATGCCAGCCAGAATGGAATCAG

GCTGGACGGGAAGAACCTGGTGCAGGAATGGCTGGCAAAGCACCAGGGTGCCTGGTATGTG

TGGAACCGCACTGAGCTCATGCAGGCGTCCCTGGACCAGTCTGTGACCCATCTCATGGGCCT

CTTTGAGCCCGGAGACACGAAATATGAGATCCACCGAGACCCCACACTGGACCCCTCCCTGA

TGGAGATGACAGAGGCTGCCCTGCGCCTGCTGAGCAGGAACCCCCGCGGCTTCTACCTCTTT

GTGGAGGGCGGCCGCATCGACCATGGTCATCATGAGGGTGTGGCTTACCAGGCACTCACTG

AGGCGGTCATGTTCGACGACGCCATTGAGAGGGCGGGCCAGCTCACCAGCGAGGAGGACAC

GCTGACCCTCGTCACCGCTGACCACTCCCATGTCTTCTCCTTTGGTGGCTACACCTTGCGAG

GGAGCTCCATCTTCGGGTTGGCCCCCAGCAAGGCTCAGGACAGCAAAGCCTACACGTCCATC

CTGTACGGCAATGGCCCGGGCTACGTGTTCAACTCAGGCGTGCGACCAGACGTGAATGAGA

GCGAGAGCGGGAGCCCCGATTACCAGCAGCAGGCGGCGGTGCCCCTGTCGTCCGAGACCC

ACGGAGGCGAAGACGTGGCGGTGTTTGCGCGCGGCCCGCAGGCGCACCTGGTGCATGGTG

TGCAGGAGCAGAGCTTCGTAGCGCATGTCATGGCCTTCGCTGCCTGTCTGGAGCCCTACACG

GCCTGCGACCTGGCGCCTCCCGCCTGCACCACCGACGCCGCGCACCCAGTTGCCGCGTCGC

TGCCACTGCTGGCCGGGACCCTGCTGCTGCTGGGGGCGTCCGCTGCTCCCTGA<u>TTTACTAA</u>

<u>AACCTTGAAATAAAATTGTAAAACATCAGTTTGAAGGCCTGACTCTCAGGGTAGTTCTTTTTT</u>

<u>AATTCTGGGTTTT</u> bIAP IV with the first intron from bIAP I (shown as bolded and underlined) -
                                                                     SEQ ID NO: 14
ATGCAGTGGGCCTGTGTGCTGCTGCTGCTGGGCCTGTGGCTACAGCTCTCCCTCACCTTCAT CCCAG<u>GTAATCAGGCGGCTCCCAGCAGCCCCTACTCACAGGGGCGGCTCTAGGCTGACCT</u>

<u>GACCAACACTCTCCCCTTGGGCAG</u>CTGAGGAGGAAGACCCCGCCTTCTGGAACCGCCAGGC

AGCCCAGGCCCTTGATGTAGCCAAGAAGTTGCAGCCGATCCAGACAGCTGCCAAGAATGTCA

-continued

TCCTCTTCTTGGGGGATGGGATGGGGGTGCCTACGGTGACAGCCACTCGGATCCTAAAGGG

GCAGATGAATGGTAAGCTGGGACCTGAGACACCCCTGGCCATGGACCAGTTCCCATACGTGG

CTCTGTCCAAGACATACAACGTGGACAGACAGGTGCCAGACAGCGCAGGCACTGCCACTGCC

TACCTGTGTGGGGTCAAGGGCAACTACAAAACCATTGGTGTAAGTGCAGCCGCCCGCTACAA

CCAGTGCAACACAACAAGTGGCAATGAGGTCACGTCTGTGATGAACCGGGCCAAGAAAGCAG

GAAAGTCAGTGGGAGTGGTGACCACCTCCAGGGTGCAGCATGCCTCCCCAGCCGGTGCTTAT

GCACACACGGTGAACCGAAACTGGTACTCAGATGCCGACCTGCCTGCCGATGCACAGACGTA

TGGCTGCCAGGACATCGCCACACAACTGGTCAACAACATGGATATTGACGTGATCCTGGGTG

GAGGCCGAATGTACATGTTTCCTGAGGGGACCCCGGATCCTGAATACCCATACGATGTCAAT

CAGACTGGAGTCCGGAAGGACAAGCGGAATCTGGTGCAGGAGTGGCAGGCCAAGCACCAGG

GAGCCCAGTATGTGTGGAACCGCACGGAGCTCCTTCAGGCAGCCAATGACCCCAGTGTAACA

CACCTCATGGGCCTCTTTGAGCCGGCAGACATGAAGTATAATGTTCAGCAAGACCCCACCAA

GGACCCGACCCTGGAGGAGATGACGGAGGCGGCCCTGCAAGTGCTGAGCAGGAACCCCCA

GGGCTTCTACCTCTTCGTGGAGGGAGGCCGCATTGACCACGGTCACCATGAAGGCAAAGCTT

ATATGGCACTGACTGATACAGTCATGTTTGACAATGCCATCGCCAAGGCTAACGAGCTCACTA

GCGAACTGGACACGCTGATCCTTGCCACTGCAGACCACTCCCATGTCTTCTCTTTTGGTGGCT

ACACACTGCGTGGGACCTCCATTTTCGGTCTGGCCCCCAGCAAGGCCTCAGACAACAAGTCC

TACACCTCCATCCTCTATGGCAATGGCCCTGGCTACGTGCTTGGTGGGGGCTTAAGGCCCGA

TGTTAATGACAGCATAAGCGAGGACCCCTCGTACCGGCAGCAGGCGGCCGTGCCCCTGTCTA

GTGAGTCCCACGGGGGCGAGGACGTGGCGGTGTTCGCGCGAGGCCCGCAGGCGCACCTGG

TGCACGGCGTGCAGGAGGAGACCTTCGTGGCGCACGTCATGGCCTTTGCGGGCTGCGTGGA

GCCCTACACCGACTGCAATCTGCCGGCCCCCTCTGGCCTCTCCGACGCCGCGCACCTGGCG

GCCAGCCCGCCTTCGCTGGCGCTGCTGGCCGGGGCGATGCTGCTGCTGCTGGCGCCTGCCT

TGTACTGA bIAP IV with the 3' UTR from bIAP I (shown as bolded and underlined) -
SEQ ID NO: 15

ATGCAGTGGGCCTGTGTGCTGCTGCTGCTGGGCCTGTGGCTACAGCTCTCCCTCACCTTCAT

CCCAGCTGAGGAGGAAGACCCCGCCTTCTGGAACCGCCAGGCAGCCCAGGCCCTTGATGTA

GCCAAGAAGTTGCAGCCGATCCAGACAGCTGCCAAGAATGTCATCCTCTTCTTGGGGGATGG

GATGGGGGTGCCTACGGTGACAGCCACTCGGATCCTAAAGGGGCAGATGAATGGTAAGCTG

GGACCTGAGACACCCCTGGCCATGGACCAGTTCCCATACGTGGCTCTGTCCAAGACATACAA

CGTGGACAGACAGGTGCCAGACAGCGCAGGCACTGCCACTGCCTACCTGTGTGGGGTCAAG

GGCAACTACAAAACCATTGGTGTAAGTGCAGCCGCCCGCTACAACCAGTGCAACACAACAAG

TGGCAATGAGGTCACGTCTGTGATGAACCGGGCCAAGAAAGCAGGAAAGTCAGTGGGAGTG

GTGACCACCTCCAGGGTGCAGCATGCCTCCCCAGCCGGTGCTTATGCACACACGGTGAACC

GAAACTGGTACTCAGATGCCGACCTGCCTGCCGATGCACAGACGTATGGCTGCCAGGACATC

GCCACACAACTGGTCAACAACATGGATATTGACGTGATCCTGGGTGGAGGCCGAATGTACAT

GTTTCCTGAGGGGACCCCGGATCCTGAATACCCATACGATGTCAATCAGACTGGAGTCCGGA

AGGACAAGCGGAATCTGGTGCAGGAGTGGCAGGCCAAGCACCAGGGAGCCCAGTATGTGTG

GAACCGCACGGAGCTCCTTCAGGCAGCCAATGACCCCAGTGTAACACACCTCATGGGCCTCT

TTGAGCCGGCAGACATGAAGTATAATGTTCAGCAAGACCCCACCAAGGACCCGACCCTGGAG

GAGATGACGGAGGCGGCCCTGCAAGTGCTGAGCAGGAACCCCCAGGGCTTCTACCTCTTCG

-continued

TGGAGGGAGGCCGCATTGACCACGGTCACCATGAAGGCAAAGCTTATATGGCACTGACTGAT

ACAGTCATGTTTGACAATGCCATCGCCAAGGCTAACGAGCTCACTAGCGAACTGGACACGCT

GATCCTTGCCACTGCAGACCACTCCCATGTCTTCTCTTTTGGTGGCTACACACTGCGTGGGAC

CTCCATTTTCGGTCTGGCCCCCAGCAAGGCCTCAGACAACAAGTCCTACACCTCCATCCTCTA

TGGCAATGGCCCTGGCTACGTGCTTGGTGGGGGCTTAAGGCCCGATGTTAATGACAGCATAA

GCGAGGACCCCTCGTACCGGCAGCAGGCGGCCGTGCCCCTGTCTAGTGAGTCCCACGGGG

GCGAGGACGTGGCGGTGTTCGCGCGAGGCCCGCAGGCGCACCTGGTGCACGGCGTGCAGG

AGGAGACCTTCGTGGCGCACGTCATGGCCTTTGCGGGCTGCGTGGAGCCCTACACCGACTG

CAATCTGCCGGCCCCCTCTGGCCTCTCCGACGCCGCGCACCTGGCGGCCAGCCCGCCTTCG

CTGGCGCTGCTGGCCGGGGCGATGCTGCTGCTGCTGGCGCCTGCCTTGTACTGAGGGGACC

CGGGGGTGGGGACACAGGCCCCGCCCTCCCTGGGAGGCAGGAAGCAGCTCTCAAATAAAC

TGTTCTAAGTATGATACAGGAGTGATACATGTGTGAAGAGAAGCCCTTAGGTGGGGGCACA

GAGTGTCTGGGTGAGGGGGGTCAGGGTCACATCAGGAGGTTAGGGAGGGGTTGATGAAGG

GCTGACGTTGAGCAAAGACCAAAGGCAACTCAGAAGGACAGTGGTGCAGGACTGGGTGTG

GTCAGCAGGGGACTGGTTGGGGGATCC

In various embodiments, the present invention contemplates the use of bacterial alkaline phosphatases. In some embodiments, the AP-based agent of the invention is derived from *Bacillus subtilis*. *Bacillus subtilis* is a Gram-positive bacterium found in soil and the gastrointestinal tract of humans. *Bacillus subtilis* secretes high levels of proteins into the environment and in the human GI tract that are properly folded. Without wishing to be bound by theory, it is believed that *Bacillus subtilis* secreted proteins in the GI tract may be resistant to degradation by common gastrointestinal proteases. *Bacillus subtilis* expresses at high levels an alkaline phosphatase multigene family. Among those isozymes, alkaline phosphatase IV is responsible for the majority of total alkaline phosphatase expression and activity in *B. subtilis*. In some embodiments, the AP-based agent of the invention is derived from *Bacillus licheniformis*. In some embodiments, the AP-based agent of the invention is derived from *Escherichia coli*.

Accordingly, in an illustrative embodiment, the AP-based agent of the invention is derived from alkaline phosphatase IV of *Bacillus subtilis*. In an embodiment, the bacterial alkaline phosphatase may have the following nucleotide and amino acid sequences:

*Bacillus subtilis* JH642 alkaline phosphatase IV,
mature protein nucleotide sequence -
SEQ ID NO: 16
AAAAAACAAGACAAAGCTGAGATCAGAAATGTCATTGTGATGATAGGCGA

CGGCATGGGGACGCCTTACATAAGAGCCTACCGTTCCATGAAAAATAACG

GTGACACACCGAATAACCCGAAGTTAACAGAATTTGACCGGAACCTGACA

GGCATGATGATGACGCATCCGGATGACCCTGACTATAATATTACAGATTC

AGCAGCAGCCGGAACAGCATTAGCGACAGGCGTTAAGACATATAACAATG

CAATTGGCGTCGATAAAAACGGAAAAAAAGTGAAATCTGTACTTGAAGAG

GCCAAACAGCAAGGCAAGTCAACAGGGCTTGTCGCCACGTCTGAAATTAA

CCACGCCACTCCAGCCGCATATGGCGCCCACAATGAATCACGGAAAAACA

-continued

TGGACCAAATCGCCAACAGCTATATGGATGACAAGATAAAAGGCAAACAT

AAAATAGACGTGCTGCTCGGCGGCGGAAAATCTTATTTTAACCGCAAGAA

CAGAAACTTGACAAAGGAATTCAAACAAGCCGGCTACAGCTATGTGACAA

CTAAACAAGCATTGAAAAAAAATAAAGATCAGCAGGTGCTCGGGCTTTTC

GCAGATGGAGGGCTTGCTAAAGCGCTCGACCGTGACAGTAAAACACCGTC

TCTCAAAGACATGACGGTTTCAGCAATTGATCGCCTGAACCAAAATAAAA

AAGGATTTTTCTTGATGGTCGAAGGGAGCCAGATTGACTGGGCGGCCCAT

GACAATGATACAGTAGGAGCCATGAGCGAGGTTAAAGATTTTGAACAGGC

CTATAAAGCCGCGATTGAATTTGCGAAAAAAGACAAACATACACTTGTGA

TTGCAACTGCTGACCATACAACCGGCGGCTTTACCATTGGCGCAAACGGG

GAAAAGAATTGGCACGCAGAACCGATTCTCTCCGCTAAGAAAACACCTGA

ATTCATGGCCAAAAAAATCAGTGAAGGCAAGCCGGTTAAAGATGTGCTCG

CCCGCTATGCCAATCTGAAAGTCACATCTGAAGAAATCAAAAGCGTTGAA

GCAGCTGCACAGGCTGACAAAAGCAAAGGGGCCTCCAAAGCCATCATCAA

GATTTTTAATACCCGCTCCAACAGCGGATGGACGAGTACCGATCATACCG

GCGAAGAAGTACCGGTATACGCGTACGGCCCCGGAAAAGAAAAATTCCGC

GGATTGATTAACAATACGGACCAGGCAAACATCATATTTAAGATTTTAAA

AACTGGAAAA

*Bacillus subtilis* JH642 alkaline phosphatase IV,
mature protein amino acid sequence -
SEQ ID NO: 17
KKQDKAEIRNVIVMIGDGMGTPYIRAYRSMKNNGDTPNNPKLTEFDRNLT

GMMMTHPDDPDYNITDSAAAGTALATGVKTYNNAIGVDKNGKKVKSVLEE

AKQQGKSTGLVATSEINHATPAAYGAHNESRKNMDQIANSYMDDKIKGKH

KIDVLLGGGKSYFNRKNRNLTKEFKQAGYSYVTTKQALKKNKDQQVLGLF

-continued

```
ADGGLAKALDRDSKTPSLKDMTVSAIDRLNQNKKGFFLMVEGSQIDWAAH

DNDTVGAMSEVKDFEQAYKAAIEFAKKDKHTLVIATADHTTGGFTIGANG

EKNWHAEPILSAKKTPEFMAKKISEGKPVKDVLARYANLKVTSEEIKSVE

AAAQADKSKGASKAIIKIFNTRSNSGWTSTDHTGEEVPVYAYGPGKEKFR

GLINNTDQANIIFKILKTGK
```

In some embodiments, the AP-based agent includes bacterial alkaline phosphatases that has one or more mutations that alter catalytic activity. In some embodiments, the bacterial alkaline phosphatases include one or more mutations such that their catalytic activity is similar or higher than mammalian alkaline phosphatases. In some embodiments, the bacterial alkaline phosphatases include one or more mutations that alter their de-phosphorylation profile. In an embodiment, the bacterial alkaline phosphatases of the invention exhibits similar de-phosphorylation profile as mammalian alkaline phosphatases. In some embodiments, the bacterial alkaline phosphatases include one or more mutations that alter their activity at higher pH. In an embodiment, the bacterial alkaline phosphatases of the invention exhibits similar activity at higher pH as mammalian alkaline phosphatases. In some embodiments, the bacterial alkaline phosphatases include one or more mutations that alter their metal requirements. In an embodiment, the bacterial alkaline phosphatases of the invention exhibits metal requirements (e.g., Mg) as mammalian alkaline phosphatases.

For example, in certain embodiments, the AP-based agent of the invention is derived from *Bacillus subtilis* JH642 alkaline phosphatase IV, and has one or more mutations at positions 101, 328, A330, and 374. For example, the AP-based agent may include one or more of the following mutations: D101A, W328H, A330N and G374C.

In various embodiments, the AP-based agent of the invention comprises a nucleotide sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In some embodiments, the AP-based agent of the invention comprises an amino sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In various embodiments, the AP-based agent of the invention may comprise an amino acid sequence having one or more amino acid mutations relative any of the protein sequences described herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, lie; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the alkaline phosphatases by reference to the genetic code, including taking into account codon degeneracy. In various embodiments, the DNA construct encoding the AP-based agent is codon optimized for protein expression in the host cell.

Mutations may be made to the AP-based agent of the invention to select for agents with desired characteristics. For examples, mutations may be made to generate AP-based agents with enhanced catalytic activity or protein stability. In various embodiments, directed evolution may be utilized to generate AP-based agents of the invention. For example, error-prone PCR and DNA shuffling may be used to identify mutations in the bacterial alkaline phosphatases that confer enhanced activity.

In various embodiments, the AP-based agent of the invention possesses desirable characteristics, including, for example, high specific activity. In various embodiments, the alkaline phosphatase of the invention possesses a specific activity of at least about 100 U/mg to about 20,000 U/mg. In various embodiments, the alkaline phosphatase of the invention possesses a specific activity of at least about 100 U/mg, about 200 U/mg, about 300 U/mg, about 400 U/mg, about 500 U/mg, about 600 U/mg, about 700 U/mg, about 800 U/mg, about 900 U/mg, about 1,000 U/mg, about 2,000

U/mg, about 3,000 U/mg, about 4,000 U/mg, about 5,000 U/mg, about 6,000 U/mg, about 7,000 U/mg, about 8,000 U/mg, about 9,000 U/mg, about 10,000 U/mg, about 11,000 U/mg, about 12,000 U/mg, about 13,000 U/mg, about 14,000 U/mg, about 15,000 U/mg, about 16,000 U/mg, about 17,000 U/mg, about 18,000 U/mg, about 19,000 U/mg, or about 20,000 U/mg.

In various embodiments, the AP-based agent of the invention is stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the alkaline phosphatase is stable in the large intestine, optionally selected from one or more of colon transversum, colon descendens, colon ascendens, colon sigmoidenum and cecum. In a specific embodiment, the alkaline phosphatase is stable in the small intestine, optionally selected from one or more of duodenum, jejunum, and ileum. In some embodiments, the alkaline phosphatase is resistant to proteases in the GI tract, including for example, the small intestine. In some embodiments, the alkaline phosphatase is substantially active at a pH of about 5.0 or above. For example, the alkaline phosphatase may be substantially active at a pH about 6.0 to about 12, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5, or about 8.0, or about 8.5, or about 9.0, or about 9.5, or about 10.0, or about 10.5, or about 11.0, or about 11.5, or about 12.0 (including, for example, via formulation, as described herein). In some embodiments, stable refers to an enzyme that has a long enough half-life and maintains sufficient activity for therapeutic effectiveness.

In various embodiments, the AP-based agent of the invention is stable in chyme.

In some embodiments, the AP-based agent described herein, include derivatives that are modified, i.e., by the covalent attachment of any type of molecule to the alkaline phosphatase such that covalent attachment does not prevent the activity of the enzyme. For example, but not by way of limitation, derivatives include alkaline phosphatases that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, formylation, metabolic synthesis of tunicamycin, etc. Additionally, the derivative can contain one or more non-classical amino acids. In various embodiments, the AP-based agent is glycosylated to ensure proper protein folding.

In still other embodiments, the AP-based agents of the invention may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The AP-based agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, a-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the alkaline phosphatases having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Further, any AP-based agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, malt, rice, flour, chalk, silica gel, sodium stearate, glycerol monostearate, talc, sodium chloride, dried skim milk, glycerol, propylene, glycol, povidone, crosspovidone, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the AP-based agent and/or pharmaceutical compositions (and/or additional therapeutic agents) can include a solubilizing agent. Also, the agents can be delivered with a suitable vehicle or delivery device. Compositions for administration can optionally include a local anesthetic such as, for example, lignocaine to lessen pain at the site of the injection. Combination therapies outlined herein can be co-delivered in a single delivery vehicle or delivery device.

Formulations

The present invention provides the described AP-based agent and/or pharmaceutical compositions (and/or additional therapeutic agents) in various formulations. Any AP-based agent and/or pharmaceutical composition (and/or additional therapeutic agents) described herein can take the form of tablets, pills, pellets, capsules, capsules containing liquids, capsules containing multiparticulates, powders, solutions, emulsion, drops, suppositories, emulsions, aerosols, sprays, suspensions, delayed-release formulations, sustained-release formulations, controlled-release formulations, or any other form suitable for use.

The formulations comprising the AP-based agent and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. For example, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting)

In one embodiment, the AP-based agent (and/or additional therapeutic agents) described herein is formulated as a composition adapted for a mode of administration described herein In various embodiments, the administration the AP-based agent and/or pharmaceutical compositions (and/or additional therapeutic agents) is any one of oral, intravenous, and parenteral. For example, routes of administration include, but are not limited to, oral, intradermal, intramuscular, intraperitoneal, intravenous, subcutaneous, intranasal, epidural, sublingual, intranasal, intracerebral, intravaginal, transdermal, rectally, by inhalation, or topically (e.g., to the ears, nose, eyes, or skin).

In one embodiment, the AP-based agent and/or pharmaceutical compositions (and/or additional therapeutic agents) described herein is formulated as a composition adapted for oral administration. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any alkaline phosphatase (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the AP-based agent and/or pharmaceutical compositions (and/or additional therapeutic agent) are formulated as solid dosage forms such as tablets, dispersible powders, granules, and capsules. In one embodiment, the AP-based agent and/or pharmaceutical compositions (and/or additional therapeutic agent) are formulated as a capsule. In another embodiment, the AP-based agent and/or pharmaceutical compositions (and/or additional therapeutic agent) are formulated as a tablet. In yet another embodiment, the AP-based agent and/or pharmaceutical compositions (and/or additional therapeutic agent) are formulated as a soft-gel capsule. In a further embodiment, the AP-based agent and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

In various embodiments, the formulations of the AP-based agents may additionally comprise a pharmaceutically acceptable carrier or excipient. As one skilled in the art will recognize, the formulations can be in any suitable form appropriate for the desired use and route of administration.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c)

humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The formulation can also include one or more application solvents. Some of the more common solvents that can be used to apply, for example, a delayed-release coating composition include isopropyl alcohol, acetone, methylene chloride and the like.

The formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition, the alkaline material may be selected from antacid materials such as aluminum hydroxides, calcium hydroxides, magnesium hydroxides and magnesium oxide.

In various embodiments, the formulation can additionally include magnesium and/or zinc. Without wishing to be bound by theory, the inclusion of magnesium and/or zinc in the formulation promotes protein folding (e.g., dimer formation) and bioactivity of the AP-based agent. In some embodiments, the formulation can include magnesium at a concentration of from about 1 µM to greater than 500 mM (e.g., from about 1 µM to more than 5 mM), inclusive of all ranges and values therebetween. In some embodiments, the formulation can include zinc at a concentration of about 1 µM to greater than 100 mM (e.g., from about 1 µM to more than 1 mM), inclusive of all ranges and values therebetween. In various embodiments, the formulation of the present invention is substantially free of metal chelators.

In various embodiments, the pH of the formulation ensures that the AP-based agent is properly folded (e.g., dimer formation) and is bioactive. In some embodiments, the formulation is maintained at a pH such that the amino acids which coordinate the binding of magnesium and/or zinc within the AP-based agent are not protonated. Protonation of such coordinating amino acids may lead to loss of metal ions and bioactivity and dimer disassociation. In various embodiments, the pH of the formulation is greater than about 6, about 6.5, about 7, about 7.5, about 8, about 8.5, about 9, about 9.5, about 10, about 10.5, about 11, about 11.5, or about 12.

Besides inert diluents, the oral compositions can also include adjuvants such as sweetening, flavoring, and perfuming agents.

In various embodiments, the AP-based agent and/or pharmaceutical compositions (and/or additional therapeutic agents) are formulated for systemic or local delivery. In an embodiment, administration is systemic. In another embodiment, it may be desirable to administer locally to the area in need of treatment.

Various methods may be used to formulate and/or deliver the agents described herein to a location of interest. For example, the alkaline phosphatase and/or pharmaceutical compositions (and/or additional therapeutic agents) described herein may be formulated for delivery to the gastrointestinal tract. The gastrointestinal tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the alkaline phosphatases and/or pharmaceutical compositions (and/or additional therapeutic agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the alkaline phosphatases and/or pharmaceutical compositions (and/or additional therapeutic agents) may be administered to a subject, by, for example, directly or indirectly contacting the mucosal tissues of the gastrointestinal tract.

In various embodiments, the administration the AP-based agent and/or pharmaceutical compositions (and/or additional therapeutic agents) is into the GI tract via, for example, oral delivery, nasogastral tube, intestinal intubation (e.g. an enteral tube or feeding tube such as, for example, a jejunal tube or gastro-jejunal tube, etc.), direct infusion (e.g., duodenal infusion), endoscopy, colonoscopy, or enema.

For example, in various embodiments, the present invention provides modified release formulations comprising at least one AP-based agent (and/or additional therapeutic agents), wherein the formulation releases a substantial amount of the AP-based agent (and/or additional therapeutic agents) into one or more regions of the GI tract. For example, the formulation may release at least about 60% of the AP-based agent after the stomach and into one or more regions of the GI tract.

In various embodiments, the modified-release formulation of the present invention releases at least 60% of the AP-based agent (or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the intestines.

In various embodiments, the modified-release formulation of the present invention releases at least 60% of the AP-based agent (or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the small intestine (e.g., one or more of duodenum, jejunum, ileum, and ileocecal junction).

In various embodiments, the modified-release formulation of the present invention releases at least 60% of the AP-based agent (or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the large intestine (e.g., one or more of cecum, ascending, transverse, descending or sigmoid portions of the colon, and rectum).

In various embodiments, the modified-release formulation does not substantially release the AP-based agent (or additional therapeutic agents) in the stomach.

In certain embodiments, the modified-release formulation releases the AP-based agent (or additional therapeutic agents) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation does not substantially release in the stomach. In these embodiments, the modified-release formulation substantially releases in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation substantially releases in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the alkaline phosphatase and/or additional agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the alkaline phosphatase and/or additional agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total alkaline phosphatase and/or additional agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the alkaline phosphatase and/or additional agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the alkaline phosphatase and/or additional agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of alkaline phosphatase and/or additional agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulation of the invention is substantially stable in chyme. For example, there is, in some embodiments, a loss of less about 50% or about 40%, or about 30%, or about 20%, or about 10% of AP-based agent activity in about 10, or 9, or 8, or 7, or 6, or 5, or 4, or 3, or 2, or 1 hour from administration.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine.

In various embodiments, the modified-release formulation of the present invention may utilize one or more modified-release coatings such as delayed-release coatings to provide for effective, delayed yet substantial delivery of the alkaline phosphatase to the GI tract together with, optionally, additional therapeutic agents.

In various embodiments, the modified-release formulation of the present invention may utilize one or more modified-release coatings such as delayed-release coatings to provide for effective, delayed yet substantial delivery of the alkaline phosphatase to the intestines together with, optionally, other additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The EUDRAGIT®-type polymers include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, Kollicoat® MAE 30 DP and Kollicoat® MAE 100 P is used. In various embodiments, the enteric agent may be a combination of the foregoing solutions or dispersions. In an embodiment, the delayed-release coating includes the enteric agent EUDRAGIT® L 30 D-55.

In certain embodiments, one or more coating system additives are used with the enteric agent. For example, one or more PlasACRYL™ additives may be used as an anti-tacking agent coating additive. Illustrative PlasACRYL™ additives include, but are not limited to PlasACRYL™ HTP20 and PlasACRYL™ T20. In an embodiment, PlasACRYL™ HTP20 is formulated with EUDRAGIT® L 30 D-55 coatings. In another embodiment, PlasACRYL™ T20 is formulated with EUDRAGIT® FS 30 D coatings.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, poly-acrylic acid esters, butadiene styrene copolymers, and the like. In one embodiment, colonic delivery is achieved by use of a slowly-eroding wax plug (e.g., various PEGS, including for example, PEG6000).

In a further embodiment, the delayed-release coating may be degraded by a microbial enzyme present in the gut flora. In one embodiment, the delayed-release coating may be degraded by a bacteria present in the small intestine. In another embodiment, the delayed-release coating may be degraded by a bacteria present in the large intestine.

In various embodiments, the modified release formulation is designed for release in the colon. Various colon-specific delivery approaches may be utilized. For example, the modified release formulation may be formulated using a colon-specific drug delivery system (CODES) as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT E), the outer coating is enteric, along with a hydroxypropyl methylcellulose barrier layer interposed in between. In another embodiment, colon delivery may be achieved by formulating the alkaline phosphatase (and/or additional therapeutic agent) with specific polymers that degrade in the colon such as, for example, pectin. The pectin may be further gelled or crosslinked with a cation such as a zinc cation. In an embodiment, the formulation is in the form of ionically crosslinked pectin beads which are further coated with a polymer (e.g., EUDRAGIT polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of the AP-based agent (and/or additional therapeutic agents), as described herein, may be evaluated using, for example, in vitro dissolution tests. For example, parallel dissolution studies in different buffers may be undertaken to characterize the behavior of the formulations at different pH levels. Alternatively, in vitro enzymatic tests may be carried out. For example, the formulations may be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations may be carried out using animal models such as dogs, guinea pigs, rats, and pigs. Further, clinical evaluation of colon specific drug delivery formulations may be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon may be monitored by colonoscopy and intubation.

In various embodiments, the present formulation provide for substantial uniform dissolution of the AP-based agent (and/or additional therapeutic agent) in the area of release in the GI tract. In an embodiment, the present formulation minimizes patchy or heterogeneous release of the AP-based agent.

In various embodiments, the present invention provides for modified-release formulations that release multiple doses of the AP-based agent, at different locations along the intestines, at different times, and/or at different pH. In an illustrative embodiment, the modified-release formulation comprises a first dose of the AP-based agent and a second dose of the AP-based agent, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the AP-based agent at different locations along the intestines, at different times, and/or at different pH. Further the dual pulse description herein applies to modified-release formulations that release the AP-based agent and an additional therapeutic agent.

In various embodiments, the invention provides a formulation comprising: a core particle having a base coat comprising one or more AP-based agents, and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more AP-based agents may further comprise one or more additional therapeutic agents. Optionally a plurality of base coats may be applied to the core particle each of which may contain an AP-based agent and/or an additional therapeutic agent. In an embodiment, the core particle includes sucrose. In an embodiment, an AP-based agent can be sprayed onto an inert core (e.g., a sucrose core) and spray-dried with an enteric layer (e.g., EUDRAGIT L30 D-55) to form pellets or beads containing AP-based agents.

Optionally, the core particle may comprise one or more AP-based agents and/or one or more additional therapeutic agents. In one embodiment, one or more doses of the AP-based agent may be encapsulated in a core particle, for example, in the form of a microsphere or a mini-sphere. For example, the AP-based agent may be combined with a polymer (e.g., latex), and then formed into a particulate, micro-encapsulated enzyme preparation, without using a sucrose core. The microspheres or mini-spheres thus formed may be optionally covered with a delayed-release coating.

A variety of approaches for generating particulates (such as microspheres, mini-spheres, aggregates, other) may be utilized for the inclusion of enzymatic proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form, for example, microspheres or mini-spheres. Alternatively, the alkaline phosphatase and stabilizing excipients (for example, trehalose, mannitol, Tween 80®, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzymatic protein, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment. In an embodiment, alkaline phosphatase may be initially solubilized as an emulsion, microemulsion, or suspension and then formulated into solid mini-spheres or microspheres. The formulation may then be coated with, for example, a delayed-release, sustained-release, or controlled-release coating to achieve delivery at a specific location such as, for example, the intestines.

In various embodiments, the formulation may comprise a plurality of modified-release particles or beads or pellets or microspheres. In an embodiment, the formulation is in the form of capsules comprising multiple beads. In another embodiment, the formulation is in the form of capsules comprising multiple pellets. In another embodiment, the formulation is in the form of capsules comprising multiple microspheres or mini-spheres.

In some embodiments, before applying the delayed-release coating to the coated core particle, the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, sodium stearyl fumarate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In various embodiments, the formulations of the present invention take the form of those as described in International Patent Application No. PCT/US15/54606, the entire contents of all of which are incorporated herein by reference.

In various embodiments, the formulations of the present invention take the form of those as described in one or more of U.S. Pat. Nos. 8,535,713 and 8,9117,77 and US Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, the formulations of the present invention take the form of those as described in International Patent Publication No. WO 2008/135090, the contents of which are hereby incorporated by reference in their entirety.

In various embodiments, the formulations of the present invention take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/0227357; 20140088202; 20130287842; 2013/0295188; 2013/0307962; and 20130184290, the contents of which are hereby incorporated by reference in their entirety.

In various embodiments, the process of formulating the AP-based agent is sufficiently gentle such that the tertiary structure of the AP-based agent (e.g., dimeric structure) is substantially intact. In various embodiments, the process of formulating the AP-based agent includes a step of refolding the AP-based agent. In such embodiments, the step of refolding the AP-based agent may include the addition of magnesium and/or cyclodextrin.

Administration and Dosages

It will be appreciated that the actual dose of the AP-based agent to be administered according to the present invention will vary according to the particular compound, the particular dosage form, and the mode of administration. Many factors that may modify the action of the AP-based agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Administration rates for a given set of conditions can be ascertained by those skilled in the art using conventional dosage administration tests.

Individual doses of the AP-based agent can be administered in unit dosage forms (e.g., tablets or capsules) containing, for example, from about 0.01 mg to about 1,000 mg, about 0.01 mg to about 900 mg, about 0.01 mg to about 800 mg, about 0.01 mg to about 700 mg, about 0.01 mg to about 600 mg, about 0.01 mg to about 500 mg, about 0.01 mg to about 400 mg, about 0.01 mg to about 300 mg, about 0.01 mg to about 200 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, or from about 0.1 mg to about 1 mg active ingredient per unit dosage for. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, or about 1,000 mg of the AP-based agent, inclusive of all values and ranges therebetween.

In one embodiment, the AP-based agent is administered at an amount of from about 0.01 mg to about 1,000 mg daily, about 0.01 mg to about 900 mg daily, about 0.01 mg to about 800 mg daily, about 0.01 mg to about 700 mg daily, about 0.01 mg to about 600 mg daily, about 0.01 mg to about 500 mg daily, about 0.01 mg to about 400 mg daily, about 0.01 mg to about 300 mg daily, about 0.01 mg to about 200 mg daily, about 0.01 mg to about 100 mg daily, an amount of from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the AP-based agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, or about 1,000 mg, inclusive of all values and ranges therebetween.

In some embodiments, a suitable dosage of the AP-based agent is in a range of about 0.01 mg/kg to about 100 mg/kg of body weight of the subject, about 0.01 mg/kg to about 90 mg/kg of body weight of the subject, about 0.01 mg/kg to about 80 mg/kg of body weight of the subject, about 0.01 mg/kg to about 70 mg/kg of body weight of the subject, about 0.01 mg/kg to about 60 mg/kg of body weight of the subject, about 0.01 mg/kg to about 50 mg/kg of body weight of the subject, about 0.01 mg/kg to about 40 mg/kg of body weight of the subject, about 0.01 mg/kg to about 30 mg/kg of body weight of the subject, about 0.01 mg/kg to about 20 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween. In other embodiments, a suitable dosage of the AP-based agent is in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the AP-based agent may be administered, for example, more than once daily (e.g., about two, about three, about four, about five, about six, about seven, about eight, about nine, or about ten times per day), about once per day, about every other day, about every third day, about once a week, about once every two weeks, about once every month, about once every two months, about once every three months, about once every six months, or about once every year.

Methods of Treatment

In some embodiments, the present invention provides for the treatment of and/or administration of an AP-based agent to a subject that has been exposed to radiation, including, but not limited to, radiotherapy. In various embodiments, administration of the AP-based agent occurs prior to exposure to radiation, such as, for example, prior to radiotherapy as part of a cancer treatment. In certain embodiments, administration of the AP-based agent occurs at the time of radiation exposure. In various embodiments, administration of the AP-based agent occurs at the time of exposure to radiation, as well as shortly after exposure to radiation. In some embodiments, administration of the AP-based agent occurs shortly after exposure to radiation. In various embodiments, administration of the AP-based agent occurs at the time of exposure to radiation, as well as continued long term after exposure to radiation. In some embodiments, administration of the AP-based agent continues for a long term after exposure to radiation. In various embodiments, administration of the AP-based agent occurs at the onset of delayed radiation enteropathy. In some embodiments, the present invention provides for the treatment and/or administration of an AP-based agent to a subject that has been exposed to or will be exposed to radiation, where the administration of the AP-based agent occurs for at least 1 year, at least 1.5 years, at least 2 years, at least 2.5 years, at least 3 years, at least 3.5 years, 4 years, at least 4.5 years, at least 5 years, at least 5.5 years, at least 6 years, at least 6.5 years, or at least 7 years after the exposure to radiation.

In various embodiments, the present invention provides for the treatment of and/or administration to a subject who suffers from radiation-related diseases or disorder, e.g. without limitation a side effect of radiotherapy or ARS.

In some embodiments, the present invention provides for the prevention of, treatment of, and/or administration to a subject who suffers from radiation enteritis. For example, the subject may be suffering from either acute or chronic radiation enteritis. Symptoms of radiation enteritis include, but are not limited to, nausea, vomiting, stomach cramping, frequent urges to use the bathroom, watery diarrhea, mucous discharge from the rectum, rectal pain, rectal bleeding, weight loss, and wave-like stomach pains.

In some embodiments, the present invention relates to a method of treating or preventing radiation-related diseases or disorders in a subject in need thereof comprising, administering to the subject an AP-based agent described herein. For example, without limitation, the AP-based agent is IAP, which may be administered orally.

In various embodiments, the present invention provides for the treatment of and/or administration to a subject who suffers from delayed radiation enteropathy and/or bowel toxicity. In some embodiments, the delayed radiation enteropathy occurs at least 3 months after the end of radiotherapy. In various embodiments, the radiotherapy is radiation therapy that treats cancer. In various embodiments, the subject is a cancer patient. In an embodiment, the radiation therapy is directed at tumors in the pelvis, abdomen, or lower torso. In some embodiments, the present treatment of the present invention does not interfere with the cancer treatment, including, but not limited to, radiation therapy.

In various embodiments, delayed radiation enteropathy is characterized by mucosal atrophy, vascular sclerosis, and progressive intestinal wall fibrosis. Symptoms of the disorder can include malabsorption of nutrients, altered intestinal transit, dysmotility, and abnormal propulsion of intestinal contents. In some embodiments, delayed radiation enteropathy symptoms are chronic and may not present until at least 3, at least 4, at least 5, at least 6, at least 7, at least 8, at least 9, at least 10, at least 11, or at least 12 months after radiation exposure. In some embodiments, delayed radiation enteropathy symptoms may not present until about 3, about 4, about 5, about 6, about 7, about 8, about 9, about 10, about 11, or about 12 months after radiation exposure.

In various embodiments, the radiation comprises ionizing radiation.

In various embodiments, the radiation comprises one or more of X-rays, gamma rays, and charged particles.

In various embodiments, the radiation exposure is at a dose of about 2 Gy, or about 2.5 Gy, or about 3 Gy, or about 3.5 Gy, or about 4 Gy, or about 4.5 Gy, or about 5 Gy, or about 10 Gy, about 20 Gy, or about 30 Gy, or about 40 Gy, or about 50 Gy, or about 60 Gy, or about 70 Gy, or about 80 Gy, or about 90 Gy, or about 100 Gy.

In various embodiments, the radiation exposure is local or whole body.

In some embodiments, the present invention relates to a method of treating or preventing radiation-related diseases or disorders in a subject in need thereof comprising, administering to the subject an AP-based agent described herein, optionally IAP, which may be administered orally where the radiation-related disease or disorder is a result of or side effect of radiotherapy.

In some embodiments, the present methods pertain to prevention or reduction of reduced diversity in the gut microbiome, e.g. that is a side effect or result of radiation exposure (including radiotherapy) and/or chemotherapy. In some embodiments, the present methods relate to repairing and/or repopulating the gut microbiome of a subject after radiation exposure (including radiotherapy) and/or chemotherapy.

In some embodiments, the radiotherapy may be part of a cancer treatment, as a primary or adjuvant therapy (e.g. with chemotherapy). In some embodiments, the radiotherapy may be used to prevent tumor recurrence after surgery and/or to remove a primary malignant tumor. In various embodiments, the subject is a cancer patient.

In some embodiments, the radiotherapy may be part of a treatment for Dupuytren's disease, Ledderhose disease, or as part of a post-surgery treatment. In various embodiments, the subject is afflicted with Dupuytren's disease, Ledderhose disease, or has recently undergone surgery.

In various embodiments, the present methods reduce or eliminate a side effect of radiotherapy, including acute side effects, long-term side effects), or cumulative side effects. In various embodiments, the present methods reduce or eliminate a local or systemic side effect of radiotherapy. In various embodiments, the side effect of radiotherapy is one or more of fatigue, nausea and vomiting, damage to the epithelial surfaces (e.g., without limitation, moist desquamation), Mouth, throat and stomach sores, Intestinal discomfort (e.g., without limitation, soreness, diarrhea, and nausea), swelling, infertility, fibrosis, epilation, dryness (e.g. without limitation, dry mouth (xerostomia) and dry eyes (xerophthalmia), and dryness of the armpit and vaginal mucosa), lymphedema, heart disease, cognitive decline, radiation enteropathy (e.g. without limitation, atrophy, fibrosis and vascular changes, which may produce malabsorption, diarrhea, steatorrhea and bleeding with bile acid diarrhea and vitamin B12 malabsorption commonly found due to ileal involvement. Pelvic radiation disease includes radiation proctitis, producing bleeding, diarrhoea and urgency, and radiation cystitis.

In various embodiments, the radiotherapy is pelvic radiotherapy. In such embodiments, the AP-based agent described herein, optionally IAP, which may be administered orally, reduces or eliminates GI-related side effects as described herein. In such embodiments, the AP-based agent described herein, optionally IAP, which may be administered orally, reduces or eliminates lower body-related side effects as described herein.

In various embodiments, the radiotherapy is pelvic radiotherapy the AP-based agent described herein, optionally IAP, which may be administered orally, reduces or eliminates one or more of radiation enteropathy, atrophy, fibrosis and vascular changes, malabsorption, diarrhea, steatorrhea, bleeding with bile acid diarrhea, malabsorption (e.g. vitamin malabsorption, e.g. vitamin B12 malabsorption). In various embodiments, the radiotherapy is pelvic radiotherapy the AP-based agent described herein, optionally IAP, which may be administered orally, reduces or eliminates radiation proctitis, producing bleeding, diarrhoea and urgency, and radiation cystitis.

In various embodiments, the radiotherapy is delivered as one or more of external-beam radiation therapy, brachytherapy, and systemic radiation therapy.

In various embodiments, the radiotherapy is an external-beam radiation therapy, selected from 3-dimensional conformal radiation therapy (3D-CRT), intensity-modulated radiation therapy (IMRT, e.g. RAPIDARC), image-guided radiation therapy (IGRT), electromagnetic-guided radiation therapy (e.g. CALYPSO) tomotherapy, stereotactic radiosurgery (SRS), stereotactic body radiation therapy (SBRT, e.g. CYBERKNIFE, GAMMAKNIFE, X-KNIFE, CLINAC), Intraoperative radiation therapy (IORT), and proton therapy.

In various embodiments, the radiotherapy is a brachytherapy, selected from interstitial brachytherapy, intracavitary brachytherapy, episcleral brachytherapy, In various embodiments, the radiotherapy is a systemic radiation therapy, selected from a radioactive iodine and a radioactive biologic. For example, the radiotherapy may be radioactive iodine ($^{131}$I), ibritumomab tiuxetan (ZEVALIN), tositumomab and iodine I 131 tositumomab (BEXXAR), samarium-153-lexidronam (QUADRAMET), and strontium-89 chloride (METASTRON).

In various embodiments, the radiotherapy comprises a dose of about 20 Gy, or about 30 Gy, or about 40 Gy, or about 50 Gy, or about 60 Gy, or about 70 Gy, or about 80 Gy, or about 90 Gy, or about 100 Gy, optionally fractionated.

In some embodiments, the present invention relates to a method of treating or preventing radiation-related diseases or disorders in a subject in need thereof comprising, administering to the subject an AP-based agent described herein, optionally IAP, which may be administered orally. where the radiation-related disease or disorder is acute radiation syndrome.

In some embodiments, ARS comprises one of more of gastrointestinal syndrome; hematopoietic syndrome; neurovascular syndrome; apoptosis-mediated tissue damage, wherein the apoptosis is optionally attributable to cellular stress; and ionizing radiation induced apoptosis tissue damage. In some embodiments, the high dose of radiation (e.g. ionizing radiation) is about 5 to about 30 Gy, or about 10 to about 25 Gy, or about 15 to about 20 Gy and, optionally, sufficient for a classification of Unit Radiation Exposure Status of RES 3. In various embodiments, the high dose of radiation is the result of a radiation disaster and/or the human patient being treated has been exposed or is at risk of being exposed to a high dose of radiation as a result of one or more of a military operation or a first responder operation in a contaminated area; a nuclear explosion; a criticality accident; a radiotherapy accident; a terrorist attack; exposure from space travel; escape of radioactive waste; exposure to open source radiation; and a nuclear reactor malfunction.

In various embodiments, the present methods and compositions provide treatment or prevention of radiation-related disorders, such as ARS. In various embodiments, the treatments described herein reduce morbidity or mortality of an exposed population of human patients and/or accelerates recovery from symptoms of ARS. ARS often presents as a sequence of phased symptoms, which may vary with individual radiation sensitivity, type of radiation, and the radiation dose absorbed. Generally, without wishing to be bound by theory, the extent of symptoms will heighten and the duration of each phase will shorten with increasing radiation dose. ARS can be divided into three phases: prodromal phase (a.k.a. N-V-D stage), latent period and manifest illness. In various embodiments, the AP-based agent, as described herein, may be administered to a human patient in any one of these three stages (i.e. the AP-based agent may be administered to a human patient in the prodromal phase, the AP-based agent may be administered to a human patient in latent period, or the AP-based agent may be administered to a human patient in manifest illness stage).

In the prodromal phase there is often a relatively rapid onset of nausea, vomiting, and malaise. Use of antiemetics, (e.g. oral prophylactic antiemetics) such as granisetron (KYTRIL), ondansetron (ZOFRAN), and 5-HT3 blockers with or without dexamethasone, may be indicated in situations where high-dose radiological exposure has occurred, is likely, or is unavoidable. Accordingly, in various embodiments, the AP-based agent may be administered to a human patient in receiving an anti-emetic agent or the AP-based agent may be administered to a human patient in combination with an anti-emetic agent. For example, the AP-based agent may also be added to the following antiemetic regimens: Ondansetron: initially 0.15 mg/kg IV; a continuous IV dose option consists of 8 mg followed by 1 mg/h for the next 24 hours. Oral dose is 8 mg every 8 hours as needed or Granisetron (oral dosage form): dose is usually 1 mg initially, and repeated 12 hours after the first dose. Alternatively, 2 mg may be taken as one dose. IV dose is based on body weight; typically 10 μg/kg (4.5 μg/lb) of body weight.

In the latent period, a human patient may be relatively symptom-free. The length of this phase varies with the dose. The latent phase is longest preceding the bone-marrow depression of the hematopoietic syndrome and may vary between about 2 and 6 weeks. The latent period is somewhat shorter prior to the gastrointestinal syndrome, lasting from a few days to a week. It is shortest of all preceding the neurovascular syndrome, lasting only a matter of hours. These times are variable and may be modified by the presence of other disease or injury. Manifest illness presents with the clinical symptoms associated with the major organ system injured (marrow, intestinal, neurovascular).

In some embodiments, the present invention relates to the mitigation of, or protection of cells from, the effects of exposure to radiation. In some embodiments, the present invention pertains to a method of mitigating and/or protecting a human patient from radiation comprising administering the AP-based agent described herein. In some embodiments, the radiation is ionizing radiation. In some embodiments, the ionizing radiation is sufficient to cause gastrointestinal syndrome or hematopoietic syndrome.

In some embodiments, the ARS comprises one of more of gastrointestinal syndrome; hematopoietic syndrome; neurovascular syndrome; apoptosis-mediated tissue damage, wherein the apoptosis is optionally attributable to cellular stress; and ionizing radiation induced apoptosis tissue damage.

Hematopoietic syndrome (a.k.a. bone marrow syndrome) is characterized by loss of hematopoietic cells and their progenitors making it impossible to regenerate blood and lymphoid system. This syndrome is often marked by a drop in the number of blood cells, i.e., aplastic anemia. This may result in infections (e.g. opportunistic infections) due to a low amount of white blood cells, bleeding due to a lack of platelets, and anemia due to few red blood cells in the circulation. These changes can be detected by blood tests after receiving a whole-body acute dose. Conventional trauma and burns resulting from a bomb blast are complicated by the poor wound healing caused by hematopoietic syndrome, increasing mortality. Death may occur as a consequence of infection (e.g. as a result of immunosuppression), hemorrhage and/or anemia. Hematopoietic syndrome usually prevails at the lower doses of radiation and leads to the more delayed death than GI syndrome.

Gastrointestinal syndrome is caused by massive cell death in the intestinal epithelium, predominantly in the small intestine, followed by disintegration of intestinal wall and death from bacteriemia and sepsis. Symptoms of this form of radiation injury include nausea, vomiting, loss of appetite, loss of absorptive capacity, hemorrhage in denuded areas, and abdominal pain. Illustrative systemic effects of gastrointestinal syndrome include malnutrition, dehydration, renal failure, anemia, sepsis, etc. Without treatment (including, for example, bone marrow transplant), death is common (e.g. via infection from intestinal bacteria). In some embodiments, the AP-based agent may be used in combination with bone marrow transplant. In some embodiments, the AP-based agent may be used in combination with one or more inhibitors of GI syndrome and/or any of the additional agents described herein.

Neurovascular syndrome presents with neurological symptoms such as dizziness, headache, or decreased level of consciousness, occurring within minutes to a few hours, and with an absence of vomiting. Additional symptoms include extreme nervousness and confusion; severe nausea, vomiting, and watery diarrhea; loss of consciousness; and burning sensations of the skin. Neurovascular syndrome is commonly fatal.

In various embodiments, methods and compositions of the present invention provide treatment and/or prevention of radiation-induced intestinal fibrosis. In some embodiments, radiation-induced intestinal fibrosis comprises one or more of bowel inflammation, bowel fibrosis, vascular sclerosis, chronic ulcers, enlargement of submucosa, enhanced fibroblast and smooth muscle cell proliferation, and excessive deposition of collagen and other extracellular matric components.

In some embodiments, the present invention provides a method for reducing the risk of death following exposure to irradiation comprising administering an effective amount of the AP-based agent. In some embodiments, the radiation is potentially lethal, and, optionally, occurs as the result of a radiation disaster. In various embodiments, the AP-based agent is administered within 24 hours following radiation exposure. In various embodiments, the AP-based agent is administered within 48 hours following radiation exposure.

In some embodiments, the AP-based agent is administered in combination with any additional agent described herein, including but not limited to a radioprotectant (e.g. an antioxidant (e.g. amifostine and vitamin E), a cytokine (e.g. a stem cell factor)), etc. Injury and death of normal cells from ionizing radiation is a combination of a direct radiation-induced damage to the exposed cells and an active genetically programmed cell reaction to radiation-induced stress resulting in a suicidal death or apoptosis. Apoptosis plays a key role in massive cell loss occurring in several radiosensitive organs (e.g., hematopoietic and immune systems, epithelium of digestive tract, etc.), the failure of which determines general radiosensitivity of the organism. In some embodiments, administration of the AP-based agent of the invention to a human patient in need thereof suppresses apoptosis in cells. In some embodiments, the AP-based agent of the invention are administered to a human patient to protect healthy cells from the damaging effects of the radiation treatment.

In various embodiments, the present invention provides a method for reducing apoptosis following exposure to irradiation. In an embodiment, the present invention provides a method for reducing apoptosis of hematopoietic cells following irradiation. In another embodiment, the present invention provides a method for reducing apoptosis of gastrointestinal cells following irradiation.

In various embodiments, administration of the AP-based agent stimulates and protects stem cells. For example, the present invention and composition may stimulate and protect hematopoietic stem cells including various hematopoietic progenitor cells. In another example, the present invention and composition may stimulate and protect gastrointestinal stem cells such as intestinal crypt stem cells. In some embodiments, the stem cells may be stimulated to proliferate and regenerate. Accordingly, the present invention provides methods of expanding the number of stem cells such as hematopoietic stem cells or gastrointestinal stem cells in a patient. In some embodiments, hematopoietic progenitor cells or gastrointestinal progenitor cells are expanded. In various embodiments, the present invention provides methods and compositions that protect the stem cells or progenitors cells from cell death (e.g., apoptosis or necrosis).

In various embodiments, methods and compositions of the present invention significantly enhances recovery of the hematopoietic and GI systems following irradiation. For example, methods and compositions of the present invention enhance bone marrow recovery following irradiation. In another example, methods and compositions of the present invention enhances regeneration of the GI crypt.

Exposure to ionizing radiation (IR) may be short- or long-term, and/or it may be experienced as a single or multiple doses and/or it may be applied to the whole body or locally. The present invention, in some embodiments, pertains to nuclear accidents or military attacks, which may involve exposure to a single high dose of whole body irradiation (sometimes followed by a long-term poisoning with radioactive isotopes), as further described herein. The same is true (with strict control of the applied dose), for example, for pretreatment of patients for bone marrow transplantation when it is necessary to prepare hematopoietic organs for donor's bone marrow by "cleaning" them from the host blood precursors. Cancer treatment may involve multiple doses of local irradiation that greatly exceeds lethal dose if it were applied as a total body irradiation (e.g. a radiotherapy accident). Poisoning or treatment with radioactive isotopes results in a long-term local exposure to radiation of targeted organs (e.g., thyroid gland in the case of inhalation of $^{125}$I). Further, there are many physical forms of ionizing radiation differing significantly in the severity of biological effects.

At the molecular and cellular level, radiation particles are able to produce breakage and cross-linking in the DNA, proteins, cell membranes and other macromolecular structures. Ionizing radiation also induces the secondary damage to the cellular components by giving rise to the free radicals and reactive oxygen species (ROS). Multiple repair systems counteract this damage, such as, several DNA repair pathways that restore the integrity and fidelity of the DNA, and antioxidant chemicals and enzymes that scavenge the free radicals and ROS and reduce the oxidized proteins and lipids. Cellular checkpoint systems detect the DNA defects and delay cell cycle progression until damage is repaired or decision to commit cell to growth arrest or programmed cell death (apoptosis) is reached Radiation can cause damage to mammalian organism ranging from mild mutagenic and carcinogenic effects of low doses to almost instant killing by high doses. Overall radiosensitivity of the organism is determined by pathological alterations developed in several sensitive tissues that include hematopoietic system, reproductive system and different epithelia with high rate of cell turnover.

Acute pathological outcome of gamma irradiation leading to death is different for different doses and may be determined by the failure of certain organs that define the threshold of organism's sensitivity to each particular dose. Thus, lethality at lower doses occurs from bone marrow aplasia, while moderate doses kill faster by inducing a gastrointestinal (GI) syndrome. Very high doses of radiation can cause almost instant death eliciting neuronal degeneration. Organisms that survive a period of acute toxicity of radiation can suffer from long-term remote consequences that include radiation-induced carcinogenesis and fibrosis developing in exposed organs (e.g., kidney, liver or lungs) in the months and years after irradiation. Cellular DNA is a major target of IR that causes a variety of types of DNA damage (genotoxic stress) by direct and indirect (e.g. free radical-based) mechanisms. All organisms maintain DNA repair system capable of effective recovery of radiation-damaged DNA; errors in DNA repair process may lead to mutations.

The AP-based agent possesses strong pro-survival activity at the cellular level and on the organism as a whole. In response to super-lethal doses of radiation, the AP-based agent may inhibit both gastrointestinal and hematopoietic syndromes, which are major causes of death from acute radiation exposure. As a result of these properties, the AP-based agent may be used to treat the effects of natural radiation events and nuclear accidents. Moreover, the AP-based agent can be used in combination with other radioprotectants, thereby, dramatically increasing the scale of protection from ionizing radiation.

The AP-based agent may be used as a radioprotective agent to extend the range of tolerable radiation doses by, for example, increasing radioresistance of human organism beyond the levels achievable by currently available measures (shielding and application of existing bioprotective agents) and drastically increase the chances of crew survival in case of nuclear accidents or large-scale solar particle events, for example.

The AP-based agent may inhibit radiation-induced programmed cell death or apoptosis in response to damage in DNA and other cellular structures. In some embodiments, the AP-based agent may not deal with damage at the cellular level and may not prevent mutations. Free radicals and reactive oxygen species (ROS) are the major cause of mutations and other intracellular damage. Antioxidants and free radical scavengers are effective at preventing damage by free radicals.

Further, in some embodiments, the present invention relates to the prevention or treatment of cutaneous radiation syndrome (CRS), i.e. skin symptoms of radiation exposure (e.g. redness (optionally associated with itching), blistering, ulceration, hair loss, damaged sebaceous and sweat glands, atrophy, fibrosis, decreased or increased skin pigmentation, ulceration or necrosis of the exposed tissue moist desquamation and collapse of the dermal vascular system after two months, resulting in the loss of the full thickness of the exposed skin.

In various embodiments, administration of the AP-based agent reduces the incidence of wounds, septic complications, and microbial infections in patients following irradiation.

In some embodiments, the present human patients experience leukopenia and/or neutropenia (e.g. absolute neutrophil count (ANC)<100 cells/μL. In some embodiments, the present methods and compositions pertain to a human patient which presents a lymphocyte count reduction of about 50% within about 24 to about 48 hours. In some embodiments, the human patient's lymphocyte count is less than about 1000 cells/μL, or about 900 cells/μL, or about 800 cells/μL, or about 700 cells/μL, or about 600 cells/μL, or about 500 cells/μL, or about 400 cells/μL, or about 300 cells/μL, or about 200 cells/μL, or about 100/cells μL (e.g. within about 24 to about 48 hours). In some embodiments, the patient's lymphocyte profile is assessed by the Andrews Lymphocyte Nomogram (see Andrews G A, Auxier J A, Lushbaugh C C. *The Importance of Dosimetry to the Medical Management of Persons Exposed to High Levels of Radiation.* In *Personal Dosimetry for Radiation Accidents. Vienna: International Atomic Energy Agency;* 1965, the contents of which are hereby incorporated by reference). In some embodiments, the present methods and compositions pertain to a human patient which presents a thrombocyte count reduction of about 50% within about 24 to about 48 hours. In some embodiments, the present human patients experience thrombocytopenia, anemia, and/or neutropenia. Thrombocytopenia is defined as a platelet count of below 50,000/μL. For example, thrombocytopenia may be characterized as grade 1 thrombocytopenia (i.e., platelet count of 75,000 to 150,000/μL), grade 2 (i.e., platelet count of 50,000 to <75,000 μL), grade 3 (platelet count of 25,000 to <50,000/μL), or grade 4 (i.e., platelet count of below 25,000/μL). Anemia may be diagnosed in men as having a hemoglobin content of less than 13 to 14 g/dL and in women as having a hemoglobin content of 12 to 13 g/dL. For example, anemia is divided into various grades based on hemoglobin levels: grade 0 (within normal limits, ≥12 g/dL); grade 1 (mild, 11.9 to 10 g/dL); grade 2 (moderate, 9.9 to 8 g/dL); grade 3 (serious/severe, 7.9 to 6.5 g/dL); and grade 4 (life-threatening, <6.5 g/dL). Neutropenia may be defined as having an absolute neutrophil count (ANC) of less than 1,500 cells/mm³. For example, neutropenia is graded as grade 1 (i.e., ANC of 1,500/mm³ or less to more than 2,000/mm³), grade 2 (ANC of 1,000/mm³ or less to more than 1,500/mm³), grade 3 (ANC of 500/mm³ or less to more than 1,000/mm³), or grade 4 (ANC of less than 500/mm³). In various embodiments, the present methods and compositions reduces the duration and severity of thrombocytopenia, anemia, and/or neutropenia in a patient following irradiation. For example, the present methods and compositions may reduce the duration and severity of Grade 4 thrombocytopenia, anemia, and/or neutropenia in a patient following irradiation.

In various embodiments, the high dose of radiation refers to a whole body dose. In various embodiments, the high dose of radiation may not be uniform. In various embodiments, the ARS is a result of a high dose of radiation. In various embodiments, the high dose of radiation is about 2 Gy, or about 2.5 Gy, or about 3 Gy, or about 3.5 Gy, or about 4 Gy, or about 4.5 Gy, or about 5 Gy, or about 10 Gy, or about 15 Gy, or about 20 Gy, or about 25 Gy, or about 30 Gy. In various embodiments, the high dose of radiation is about 5 to about 30 Gy, or about 10 to 25 Gy, or about 15 to 20 Gy. In some embodiments, the high dose of radiation is assessed by one or more of physical dosimetry and/or biological dosimetry (e.g. multiparameter dose assessments), cytogenics (e.g. chromosomal analysis for, for example, blood samples (including, by way of non-limiting example, dicentric analysis).

In various embodiments, whole-body radiation doses can be divided into sublethal (<2 Gy), potentially lethal (2-10 Gy), and supralethal (>10 Gy).

The radiation exposure status (RES) of a given unit is based on the operational exposure above normal background radiation. It is designed to be an average, based upon unit-level dosimeters. In various embodiments, the high dose of radiation is sufficient for a classification of Unit Radiation Exposure Status of RES 3.

In various embodiments, the radiation is ionizing radiation (e.g. one or more of alpha particles, beta particles, gamma rays, and neutrons) In various embodiments, when radiation interacts with atoms, energy is deposited, resulting in ionization (electron excitation). This ionization may damage certain critical molecules or structures in a cell by direct and indirect action. The radiation may directly hit a particularly sensitive atom or molecule in the cell. The damage from this is irreparable; the cell either dies or is caused to malfunction. The radiation also can damage a cell indirectly by interacting with water molecules in the body. The energy deposited in the water leads to the creation of unstable, toxic hyperoxide molecules; these then damage sensitive molecules and afflict subcellular structures.

In some embodiments, the radiation may be caused by one or more of the following radioactive materials: Americium (e.g. $^{241}$Am), Cesium (e.g. 137Cs), Cobalt (e.g. 60 Co), Uranium (e.g. depleted Uranium), Iodine (e.g. $^{131, 132, 134,}$ 135I), Phosphorus (e.g. $^{32}$P), Plutonium (e.g. $^{238, 239}$Pu), Radium (e.g. $^{226}$Ra), Strontium (e.g. $^{90}$Sr), Tritium (e.g. $^{3}$H), and Uranium (e.g. $^{235}$U, $^{238}$U, $^{239}$U).

In various embodiments, the high dose of radiation is the result of a radiation disaster. In various embodiments, the human patient is been exposed or is at risk of being exposed to a high dose of radiation, which may be a result of one or more of a military operation or a first responder operation in a contaminated area; a nuclear explosion; a criticality accident; a radiotherapy accident; a terrorist attack; exposure from space travel; escape of radioactive waste; exposure to open source radiation; and a nuclear reactor malfunction.

A method of treating or preventing a side effect of a chemotherapeutic treatment in a subject in need thereof comprising, administering to the subject an AP-based agent described herein.

In various embodiments, the present invention provides for the treatment of and/or administration to a subject who suffers from a side effect of a chemotherapeutic treatment In some embodiments, the side effect of a chemotherapeutic treatment is selected from alopecia, myelosuppression, renal toxicity, weight loss, pain, nausea, vomiting, diarrhea, constipation, anemia, malnutrition, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment.

A method of treating a cancer by improving the effectiveness of a chemotherapeutic treatment in a subject in need thereof comprising, administering to the subject an AP-based agent described herein. In various embodiments, the AP-based agent described herein acts as an adjuvant to a chemotherapeutic treatment described herein. In various embodiments, the AP-based agent described herein improves the anti-cancer effect and/or increases the therapeutic window of any of the chemotherapeutic treatments described herein. In various embodiments, administering to the subject an AP-based agent described herein does not interfere with treatment of cancer.

In some embodiments, the chemotherapeutic treatment is one or more of alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above.

In various embodiments, the cancer is selected from basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

Additional Therapeutic Agents and Combination Therapy

Administration of the present compositions and formulations comprising the AP-based agent may be combined with additional agents. Co-administration of the additional agent and the present compositions/formulations may be simultaneous or sequential. Further, the present compositions/formulations may comprise an additional agent (e.g. via co-formulation). For example, the additional agent and the AP-based agent may be combined into a single formulation. Alternatively, the additional agent and the AP-based agent may be formulated separately.

In one embodiment, the additional agent and the AP-based agent are administered to a subject simultaneously. The term "simultaneously" as used herein, means that the additional gent and the AP-based agent are administered with a time separation of no more than about 60 minutes, such as no more than about 30 minutes, no more than about 20 minutes, no more than about 10 minutes, no more than about 5 minutes, or no more than about 1 minute. Administration of the additional agent and the AP-based agent can be by simultaneous administration of a single formulation (e.g., a formulation comprising the additional agent and the alkaline phosphatase) or of separate formulations (e.g., a first formulation including the additional agent and a second formulation including the AP-based agent).

In a further embodiment, the additional agent and the AP-based agent are administered to a subject simultaneously but the release of the additional agent and the alkaline phosphatase from their respective dosage forms (or single unit dosage form if co-formulated) may occur sequentially.

Co-administration does not require the additional agent and the AP-based agent to be administered simultaneously, if the timing of their administration is such that the pharmacological activities of the additional agent and the AP-based agent overlap in time. For example, the additional agent and the AP-based agent can be administered sequentially. The term "sequentially" as used herein means that the additional agent and the AP-based agent are administered with a time separation of more than about 60 minutes. For example, the time between the sequential administration of the additional agent and the AP-based agent can be more than about 60 minutes, more than about 2 hours, more than about 5 hours, more than about 10 hours, more than about 1 day, more than about 2 days, more than about 3 days, or more than about 1 week apart. The administration times will depend on the rates of metabolism, excretion, and/or the pharmacodynamic activity of the additional agent and the AP-based agent being administered. Either the additional agent or the AP-based agent may be administered first.

Co-administration also does not require the additional agent and the AP-based agent to be administered to the subject by the same route of administration. Rather, each therapeutic agent can be administered by any appropriate route, for example, parenterally or non-parenterally.

In various embodiments, the additional agents of the present invention include one or more of blood products, colony stimulating factors, cytokines and/or growth factors, antibiotics, diluting and/or blocking agents, mobilizing or chelating agents, stem cell transplants, antioxidants or free radicals, and radioprotectants.

In some embodiments, the blood product is one or more of hematopoietic growth factors, such as filgrastim (e.g. NEUPOGEN), a granulocyte colony-stimulating factor (G-CSF), which may be optionally pegylated (e.g. NEULASTA); sargramostim (LEUKINE); and a granulocyte-macrophage colony-stimulating factor (GM-CSF) and a KSF.

In some embodiments, the additional agent is one or more cytokines and/or growth factors that may confer radioprotection by replenishing and/or protecting the radiosensitive stem cell populations. Radioprotection with minimal side effects may be achieved by the use of stem cell factor (SCF, c-kit ligand), Flt-3 ligand, and interleukin-1 fragment IL-1b-rd. Protection may be achieved through induction of proliferation of stem cells (e.g. via all mentioned cytokines), and prevention of their apoptosis (e.g. via SCF). The treatment allows accumulation of leukocytes and their precursors prior to irradiation thus enabling quicker reconstitution of the immune system after irradiation. SCF efficiently rescues lethally irradiated mice with a dose modifying factor (DMF) in range 1.3-1.35 and is also effective against gastrointestinal syndrome. Flt-3 ligand also provides strong protection in mice and rabbits.

Several factors, while not cytokines by nature, stimulate the proliferation of the immunocytes and may be used in combination with the AP-based agent at the doses and regimens described herein. For example, 5-AED (5-androstenediol) is a steroid that stimulates the expression of cytokines and increases resistance to bacterial and viral infections. Synthetic compounds, such as ammonium trichloro(dioxoethylene-O,O'-) tellurate (AS-101), may also be used to induce secretion of numerous cytokines and for combination with the AP-based agent. Growth factors and cytokines may also be used to provide protection against the gastrointestinal syndrome. Keratinocyte growth factor (KGF) promotes proliferation and differentiation in the intestinal mucosa, and increases the post-irradiation cell survival in the intestinal crypts. Hematopoietic cytokine and radioprotectant SCF may also increase intestinal stem cell survival and associated short-term organism survival.

In certain embodiments, the AP-based agent may be added to a regimen of cytokines (e.g. for FILGRASTIM (G-CSF) 2.5-5 µg/kg/d QD s.c. (100-200 µg/m²/d); for SARGRAMOSTIM (GM-CSF) 5-10 µg/kg/d QD s.c. (200-400 µg/m²/d); and/or for PEGFILGRASTIM (pegG-CSF) 6 mg once s.c.).

In some embodiments, the additional agent is an interleukin, such as IL-12 (e.g. HEMAMAX (NEUMEDICINES, INC.)).

In some embodiments, the antibiotic is one or more of an anti-bacterial (anti-gram positive and anti-gram negative agents), and/or anti-fungal, and/or anti-viral agent. By way of non-limiting example, in some embodiments, the antibiotic may be a quinolone, e.g. ciprofloxacin, levofloxacin, a third- or fourth-generation cephalosporin with pseudomonal coverage: e.g., cefepime, ceftazidime, or an aminoglycoside: e.g. gentamicin, amikacin, penicillin or amoxicillin, acyclovir, vanomycin. In various embodiments, the antibiotic targets *Pseudomonas aeruginosa.*

In some embodiments, the additional agent is a diluting and/or blocking agents. For example, stable iodide compounds may be used (e.g. liquid (ThyroShield) and the tablet (losat) KI (NUKEPILLS), Rad Block, I.A.A.A.M., No-Rad, Life Extension (LEF), KI4U, NukeProtect, ProKI)). A 130 mg dose of daily of oral potassium iodide (KI) may be used in conjunction with the AP-based agent.

In some embodiments, the additional agent is a mobilizing or chelating agent. Illustrative mobilizing agents include propylthiouracil and methimazole, with may reduce the thyroid's retention of radioactive compounds. Further the AP-based agent can be used alongside increasing oral fluids to a human patient to promote excretion. Illustrative chelating agents are water soluble and excreted in urine. Illustrative chelating agents include DTPA and EDTA. Dimercaprol forms stable chelates with mercury, lead, arsenic, gold, bismuth, chromium, and nickel and therefore may be considered for the treatment of internal contamination with the radioisotopes of these elements. Penicillamine chelates copper, iron, mercury, lead, gold, and possibly other heavy metals.

In some embodiments, the additional agent is a stem cell transplant (e.g. bone marrow transplant, PBSCT, MSCT).

In some embodiments the stem cell transplant is Remestemcel-L (Osiris) of CLT-008 (Cellerant).

In some embodiments, the additional agent is an antioxidant or free radical. Antioxidants and free radical scavengers that may be used in the practice of the invention include, but are not limited to, thiols, such as cysteine, cysteamine, glutathione and bilirubin; amifostine (WR-2721); vitamin A; vitamin C; vitamin E; and flavonoids such as Indian holy basil (*Ocimum sanctum*), orientin and vicenin.

In some embodiments, the additional agent may be a radioprotectant e.g. an antioxidant (e.g. amifostine and vitamin E, gamma tocotrienol (a vitamin-E moiety), and genistein (a soy byproduct)), a cytokine (e.g. a stem cell factor), a growth factor (e.g. keratinocyte growth factor), a steroid (e.g. 5-androstenediol), ammonium trichloro(dioxoethylene-O,O')tellurate, thyroid protecting agents (e.g. Potassium iodide (KI) or potassium iodate ($KIO_3$) (e.g. liquid (ThyroShield) and the tablet (losat) KI (NUKEPILLS), Rad Block, I.A.A.A.M., No-Rad, Life Extension (LEF), KI4U, NukeProtect, ProKI)), anti-nausea agents, anti-diarrhea agents, antiemetics ((e.g. oral prophylactic antiemetics) such as granisetron (KYTRIL), ondansetron (ZOFRAN), and 5-HT3 blockers with or without dexamethasone), analgesics, anxiolytics, sedatives, cytokine therapy, and antibiotics.

Gastric lavage and emetics, which can be used as additional agents, can be used to empty the stomach promptly and completely after the ingestion of poisonous materials. Purgatives, laxatives, and enemas, which also can be used as additional agents, can reduce the residence time of radioactive materials in the colon. Further additional agents include ion exchange resins which may limit gastrointestinal uptake of ingested or inhaled radionuclides, ferric ferrocyanide (Prussian blue) and alginates, which have been used in humans to accelerate fecal excretion of cesium-137.

In still other embodiments, the additional agent may be an agent used to treat radiation-related disorders, such as, for example, 5-AED (Humanetics), Ex-RAD (Onconova), Beclometasone Dipropionate (Soligenix), detoxified endotoxin, EA-230 (Exponential Biotherapies), ON-01210Na (Onconova), Sothrombomodulin alfa (PAION), Remestemcel-L (Osiris), BIO-100, BIO-200, BIO-300, BIO-400, BIO-500 (Humanetics), CLT-008 (Cellerant), EDL-2000 (RxBio), Homspera (ImmuneRegen), MnDTEIP (Aeolus Pharmaceuticals), RLIP-76 (Terapio), and RX-100 and RX 101 (RxBio).

Further, in some embodiments, the AP-based agent can be used in combination with shielding; reduction of radiation exposure time; and use of agents to reduce body exposure (e.g. uses of gloves, face mask, hood, protective clothing (e.g. anticontamination suits such as TYVEK ANTI-C SUITS or MOPP-4)).

EXAMPLES

Example 1. Stability of AP-Based Agent in Chyme

The stability of various AP-based agents in chyme is assessed. Chyme specimens (5 individual and 1 mixed) are first evaluated for background alkaline phosphatase activity prior to use in analysis, and chyme specimens with the lowest amount of background activity are used for the stability study. Three separate AP proteins, hiAP, biAP, and a hiAP-FC fusion are incubated at 37° C. in a HEPES buffer containing 5% clarified human chyme. Two aliquots from each sample are removed at 0, 30, 60, 120, 180, and 240 minutes of incubation. One aliquot is immediately mixed with Laemli sample buffer for SDS-PAGE analysis and the other is immediately mixed with a protease inhibitor cocktail and stored frozen for analysis of AP activity. The samples are also incubated in HEPES buffer alone and aliquots removed at 0 and 240 minutes as controls. Collected samples are subjected to SDS-PAGE and the products of incubation examined by Coomassie blue staining.

Alkaline phosphatase activity before and after incubation in chyme is examined using a commercial kit (Abcam). It is expected that all AP-based agents remain stable in chyme for the entire duration of the experiment. Additionally, there is no reduction in AP activity after chyme incubation, which confirms that the AP-based agents are not degraded in chyme under the tested conditions.

Example 2. Engineering Bacterial AP-Based Agent to Increase Catalytic Activity by Specific Amino Acids Changes There are some functional differences between the bacterial and mammalian APs. By and large, the mammalian enzymes exhibit 20-30-fold higher catalytic activity as well as a shift in the pH of activity towards higher pH. Some mammalian alkaline phosphatases also require magnesium in order to achieve maximal activity. In addition, it is not known whether bacterial AP maintains the same de-phosphorylation pattern as the mammalian APs. By nucleotide comparison with mammalian AP, the bacterial *Escherichia coli* AP has been successfully engineered to achieve activity similar to the mammalian AP. Several residues have been mutagenized and AP activity assessed. Previous work indicated that the D101S mutant in *Escherichia coli* AP, which contains an Asp/Ser replacement within the -Asp101-Ser102-Ala103-region of the active center, showed a 10-fold higher activity over the wild-type AP ((Zhang, F. Appl. Biochem. Biotechnol. 2002; 101:197-210). Double mutants such as D153H/K328H resulted in enhanced activity and properties of *E. coli* AP similar to the mammalian alkaline phosphatases, and the D153H/K328H mutant enzyme is 5.6-fold more active than the wild-type enzyme. Furthermore, the double mutant D153G/D330N is as active as the mammalian AP, with 40-to 50-fold higher activity than that of the wild-type bacterial enzyme (Le Du M-H., 2002; Murphy, J E., 1994; Muller, B H., 2001).

To engineer the BSAP IV, the BSAP IV sequence disclosed herein (e.g., SEQ ID NO: 17) is synthesized de novo with single, double, triple or quadruple mutations at positions D101A, W328H, A330N and G374C. The BSAP variants are tested in various in vitro and in vivo assays for their therapeutic potentials.

Example 3: Engineering Bacterial AP-Based Agent to Increase Catalytic Activity by Direct Evolution Error-prone PCR (Leung, D. Technique, 1989; 1:11-15) and DNA shuffling are utilized to identify mutations in the mammalian and bacterial AP gene that can confer an increased activity.

For example, for the error-prone PCR, specific primers are used to amplify regions of the BSAP IV gene. Primers are designed to amplify specific regions of the BSAP IV coding sequence that do not affect mutation already known to increase BSAP IV activity. The PCR parameters are as follow: 1 mM dCTP, 1 mM dTTP, 0.2 mM dATP, 0.2 mM dGTP, 7 mM $Mg^{2+}$, 0.05 mM $Mn^{2+}$50 ng of each primer, 1×Taq DNA polymerase buffer, 10 ng of DNA template and 2.5 units of Taq DNA polymerase in 50 ml final volume. The reaction is subjected to 25 cycles as follows: 1 minute at 94° C., 1 minute at 56° C., and 1.5 minutes at 72° C. to generate an error frequency of approximately 1 to 2 substitutions per 1000 bases. The amplified products are digested appropriate restriction endonucleases, followed by the ligation with the same digested template vector. The *E. coli* SL21 (DE3) containing sequences from the error prone PCR is then transformed with the ligation mixture to create the mutant library (Moore, J C. Nat. Biotechnol. 1996; 14:458-467).

DNA shuffling is performed as described by Stemmer (Proc. Natl. Acad. Sci. USA, 1994; 91:10747-10751) and Lorimer and Pastan (Nucleic Acids Res. 1995; 23:3067-3068) with some modifications (Xu, HF. et al 2003). A total quantity of 5 mg BSAP IV fragments is randomly fragmented using DNase I for 15 minutes. The digested DNA fragments are visualized as a small smear on a 2% low melting temperature agarose gel. The fragments in specified molecular size ranges are subjected to gel extraction and then eluted with 30 ml elution buffer (10 mM Tris, 1 mM EDTA, pH 8.0). Reassembly of the DNA fragments was conducted by PCR without primers, using the following conditions: 94° C. for 4 minute, then 40 cycles of 94° C. for 50 seconds, 56° C. for 50 seconds, 72° C. for 50 seconds+5 seconds/cycle, followed by a final extension step at 72° C. for 7 minutes. The reassembled DNA is amplified by the following procedure with two flanking primers, and the final PCR products are ligated into pET vector and then transformed into *E. coli* SL21 (DE3).

The screening of mutant libraries is carried out by assessing activity of cell-free medium. The members of the mutant libraries are allowed to grow for 16-18 hours on LB plates with ampicillin and indicator substrate 5-bromo-4-chloro-3-indolyl phosphate, which can be de-phosphorylated by AP resulted in blue colonies. Each active (i.e. blue) colony is then picked and suspended in a unique well of a 96-well plate containing 200 ml of media. The cells are then treated for growth conditions and activity assay. Clones with improved activity are then sequenced.

Example 4:/In Vivo Disease Models to Assess Efficacy of AP-Based Agent in a Pelvic Radiation Model An in vivo model is utilized to verify the therapeutic potential of AP-based agents for a pelvic radiation model.

Bovine IAP manufactured by Synthetic Biologics (SYN BIAPII) is administered in the drinking water of mice from the day of radiation (day 0).

Daily body weight is assessed. Survival assessment is undertaken at 20 days (for 12 mice).

Plasma, ileum and jejunum are collected at day 4 for a group of 4 mice for future analysis (in case the study worked).

One or more of the following cohorts may be studied ("TBI" is Total Body Irradiation):

| Group | # Animals | TBI (Day 0) | Treatment | Dosing Route/Frequency | Study Termination | Terminal Collections |
|---|---|---|---|---|---|---|
| 1 | 10 | — | — | — | n = 4: Day 4 | Plasma, |
| 2 | 16 | ~LD10/20 | Vehicle | Drinking Water | n = 12: Day 20 | Ileum, |
| 3 | 16 | 10.5 Gy | SYN BIAPII | and | | Jejunum |
| 4 | 16 | ~LD30/20 | Vehicle | PO (BID) | | |
| 5 | 16 | 11.5 Gy | SYN BIAPII | Days 0-20 | | |
| 6 | 16 | ~LD70/20 | Vehicle | | | |
| 7 | 16 | 12.5 Gy | SYN BIAPII | | | |

The cells are then treated for growth conditions and activity assay. Clones with improved activity are then sequenced.

Example 5: IAP Effectively Maintained Gut Barrier Integrity Following 400 Rad Total Body Irradiation In order to assess the effect of IAP on maintaining gut barrier integrity after irradiation, C57B16 mice (n=4/group) received a whole body radiation of 400 rads on day 1 of the study. Intestinal alkaline phosphatase (IAP, SYN BIAPII) at doses of 100 U/ml, 300 U/ml, or 1,000 U/ml were administered from study day −4 via the drinking water. As a control, a cohort of mice received vehicle in their drinking water. Mice were monitored daily for body weight, stool consistency, food and water intake, and mortality. On study day 4, test article administration was discontinued and mice were sacrificed. The table below provides an overview of the study setup.

| Mice (n) | Rad. dose | Treatment | Doses | Termination endpoints day 4 |
|---|---|---|---|---|
| 12 | 400 | Vehicle | | n = 4/each group |
| | | IAP | 100 U/ml | (gut histology, gut permeability, |

*-continued*

| Mice (n) | Rad. dose | Treatment | Doses | Termination endpoints day 4 |
|---|---|---|---|---|
| | | | 300 U/ml | LPS levels, blood cytokines, |
| | | | 1000 U/ml | bone marrow cellularity, feces collection, blood and gut tissues) |

Intestinal permeability was then measured using Fluorescein Isothiocyanate-conjugated (FITC)-Dextran to determine the effect of IAP administration. When inflammation causes disruption of intestinal epithelial tight junctions due to radiation exposure, leakage of serum FITC-dextran (a 4-kDa molecule that under normal conditions is not able to cross the epithelial barrier) into circulation can occur. Accordingly, intestinal permeability is presented as the concentration of serum FITC-Dextran of the sample. On study day 4, prior to being sacrificed, the mice received FITC-dextran at a dose of 300 mg/kg body weight via oral gavage. Blood was collected 90 minutes later and serum was used for the analysis of the FITC-dextran concentration. Fluorescent intensity was measured with a fluorospectrophotometer (480 nm ex, 520 nm em). A standard curve generated by serial dilution of known amount of FITC-dextran was used to calculate absolute values.

FIG. 1 depicts the results of the study. Administration of intestinal alkaline phosphatase significantly diminished gut leakage due to radiation exposure in a dose-dependent manner. This result suggests that IAP has the ability to protect the gut from damage caused by radiation.

Example 6: In Vivo Disease Models to Assess Efficacy of AP-Based Agent in a Delayed Radiation Enteropathy Model In order to assess Intestinal Alkaline Phosphatase (IAP) efficacy in protecting the gut barrier from chronic radiation exposure, C57B16 mice are used as an in vivo disease model, where the mice receive a whole body radiation dose of 750 rads on day 1. Subsequent testing was performed to evaluate the symptoms of delayed radiation enteropathy.

One group of mice (n=30) receives a dose of IAP (SYN BIAPII), ranging in concentration from 10 U/ml and 1,000 U/ml, from day −4 until day 7 post radiation via the drinking water. After that, administration of IAP is discontinued. The study controls include one group of mice (n=30) that receives vehicle buffer in the drinking water, and another cohort (n=30) that is not irradiated and receives vehicle buffer in the drinking water.

Mice are monitored daily for any sign of discomfort. Body weight, stool consistency, food and water intake are measured weekly. Mice are sacrificed at the following time points: 2 weeks, 1 month, 3 months, 6 months and 9 months post radiation to evaluate for markers of chronic radiation enteropathy.

For example, at time of sacrifice, blood and tissues are collected. Specimens are fixed in 10% formalin as well as frozen in OCT. In addition, a piece of each specimen is collected and snap-frozen for RNA extraction to assess inflammatory markers. Prior to sacrifice, gut barrier function is assessed with FITC-dextran as previously described in Example 5.

Markers of chronic radiation include: blood urea nitrogen (BUN); renal, pulmonary, intestinal and cardiac histopathology by H&E staining; and special stains for fibrosis such as Sirius red.

Blood is drawn before radiation and at 3, 7, 10, 14 and 21 days post-radiation for complete blood count (CBC) analysis to monitor bone-marrow recovery.

Feces are collected prior to radiation and at 1 week, 2 weeks and monthly thereafter for microbiome analyses.

Mice that experience substantial weight loss or diminished activity or food and water intake are sacrificed.

In a parallel otherwise identical study, the IAP administration is discontinued on day 30 post radiation.

Finally, the studies are repeated with a radiation dose of 950 rads.

The data show that IAP, when administered for one week and/or for 30 days, provides long-term benefits including improving barrier function, diminishing inflammatory cytokines, diminishing intestinal fibrosis, and diminishing radiation-mediated mortality. The study also identifies the working IAP dose range between 10 U/ml and 1,000 U/ml in the drinking water. Thus, oral administration of IAP can be used to treat chronic radiation enteropathy by diminishing the late intestinal consequences of radiation exposure.

Example 7: IAP Effectively Maintained Gut Barrier Integrity and Reduced Inflammation Following 850 or 1400 Rad Total Body Irradiation Total body radiation causes significant changes in the GI track by increasing the gut permeability (gut leakage) and by inducing a pro-inflammatory response. In order to assess the effect of IAP on maintaining gut barrier integrity after irradiation with doses of 850 rads or 1400 rads, C57B16 mice (n=5/group) received a whole body radiation of 850 rads or 1400 rads on day 1 of the study. Intestinal alkaline phosphatase (IAP, SYN BIAPII) at doses of 100 U/ml were administered from study day −4 via the drinking water. As a control, a cohort of mice received vehicle in their drinking water. Another control included a cohort of mice (sham, n=5) that received no exposure to radiation. On study day 4, test article administration was discontinued and mice were sacrificed. The table below provides an overview of the study setup.

| Mice (n) | Rad. dose | Treatment | IAP dose | Endpoint (terminal at day 4) |
|---|---|---|---|---|
| 5 | sham | — | — | Histology, |
| 5 | 850 | Vehicle | — | Permeability, |
| 5 | 850 | SYN BIAPII | 100 U/ml | GI cytokines, |
| 5 | 1400 | Vehicle | | Bacteria in lymph nodes, |
| 5 | 1400 | SYN BIAPII | 100 U/ml | Feces for microbiome & calprotectin, Clinical observations, Diarrhea, Weight |

Radiation-induced gut hyperpermeability was then measured using Fluorescein Isothiocyanate-conjugated (FITC)-Dextran to determine the effect of IAP administration. When inflammation causes disruption of intestinal epithelial tight junctions due to radiation exposure, leakage of serum FITC-dextran (a 4-kDa molecule that under normal conditions is not able to cross the epithelial barrier) into circulation can occur. Accordingly, intestinal permeability is presented as the concentration of serum FITC-Dextran of the sample. On study day 4, prior to being sacrificed, the mice received FITC-dextran at a dose of 300 mg/kg body weight via oral gavage. Blood was collected 90 minutes later and serum was used for the analysis of the FITC-dextran concentration. Fluorescent intensity was measured with a fluorospectrophotometer (480 nm ex, 520 nm em). A standard curve generated by serial dilution of known amount of FITC-dextran was used to calculate absolute values.

Figure 2:
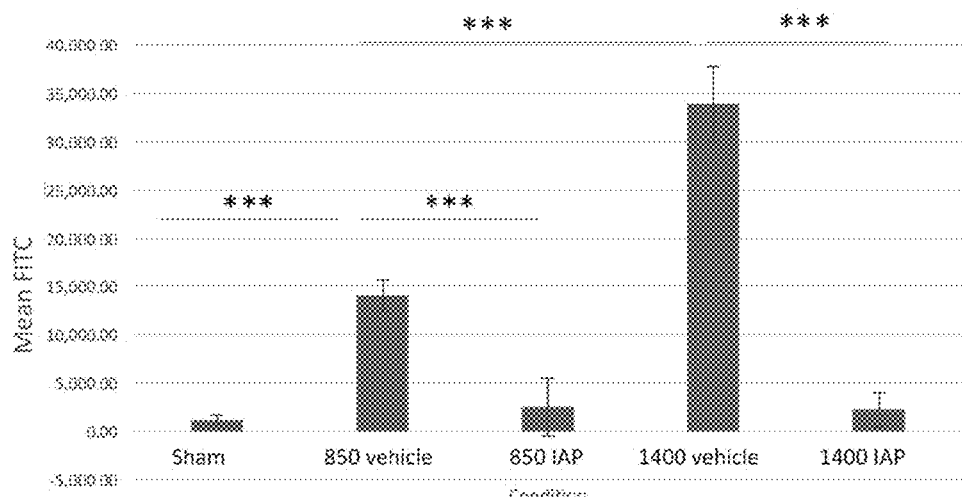
FIG. 2 depicts radiation-induced gut hypermeability as measured by serum FITC-Dextran in irradiated mice (both 850 and 1400 rads) that had either been given IAP treatment or vehicle.
Figure 4A:
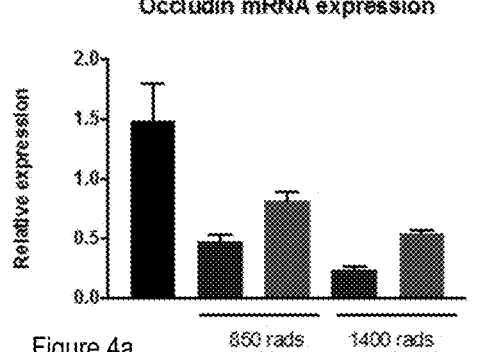
FIG. 4a-4d depicts gene expression of ZO-1 (FIG. 4b), ZO-2 (FIG. 4c), ZO-3 (FIG. 4d), and occludin (FIG. 4a) in the colons of irradiated mice (both 850 and 1400 rads) and irradiated mice that received vehicle. In all panels, the left-most bar represents the sham data; the left bar within the 850 rad cohort represents vehicle data, while the right bar represents IAP data; and the left bar within the 1400 rad cohort represents vehicle data, while the right bar represents IAP data.
Figure 4B:
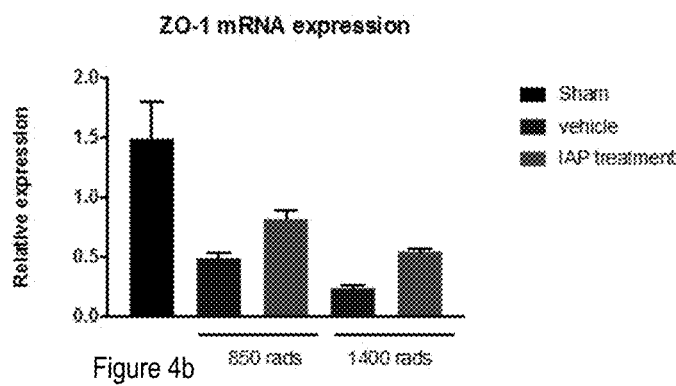
Figure 4C:
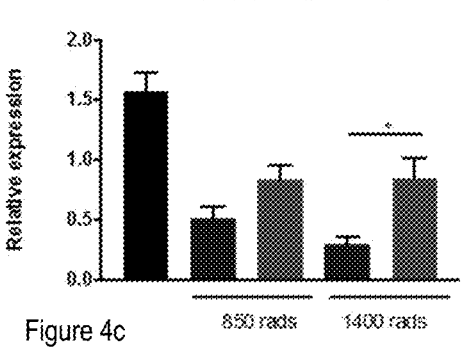
Figure 4D:
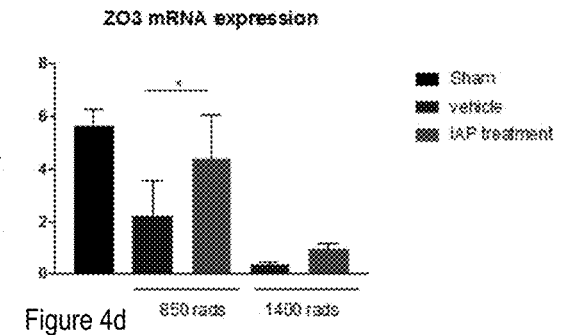

FIG. 2 depicts the results of the study. Administration of intestinal alkaline phosphatase significantly diminished gut leakage due to radiation exposure in both the 850 and 1400 rads cohort. This result suggests that IAP has the ability to protect the gut from damage caused by radiation at high doses such as 850 and 1400 rads.

Radiation-induced gut hyperpermeability was further assessed by measuring with qPCR tight junction gene expression in the ileum and colon of sacrificed mice. Gene expression of ZO-1, ZO-2, ZO-3, and occludin were measured by relative mRNA levels. FIG. 3 depicts the results in the ileum and FIG. 4 depicts the results in the colon, which suggest that IAP recovered expression of these tight junction genes in irradiated mice (both 850 and 1400 rads) as compared to irradiated mice that received vehicle. Indeed, the tight junction gene expression in mice having received treatment of IAP was more similar to the expression levels in mice that did not receive any radiation as compared to irradiated mice that received vehicle in both the ileum and colon.

Figures 5A, 5B:
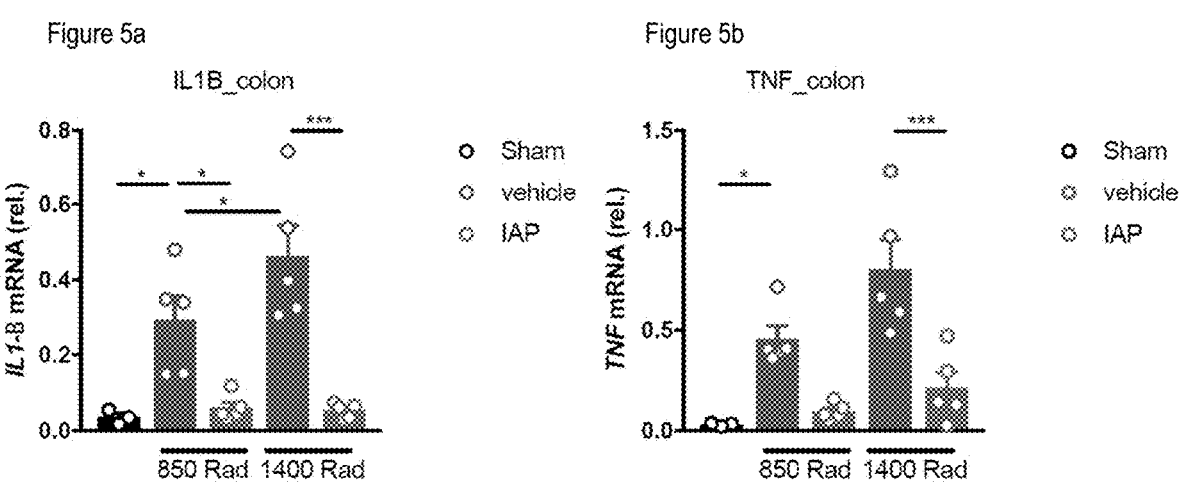
FIG. 5a-5b shows that IL1-6 (FIG. 5a) and TNF (FIG. 5b) levels were decreased in colons of irradiated mice (850 and 1400 rads) that received IAP treatment, as compared to irradiated mice that received vehicle. In all panels, the left-most bar represents the sham data; the left bar within the 850 rad cohort represents vehicle data, while the right bar represents IAP data; and the left bar within the 1400 rad cohort represents vehicle data, while the right bar represents IAP data.
Figures 6A, 6B:
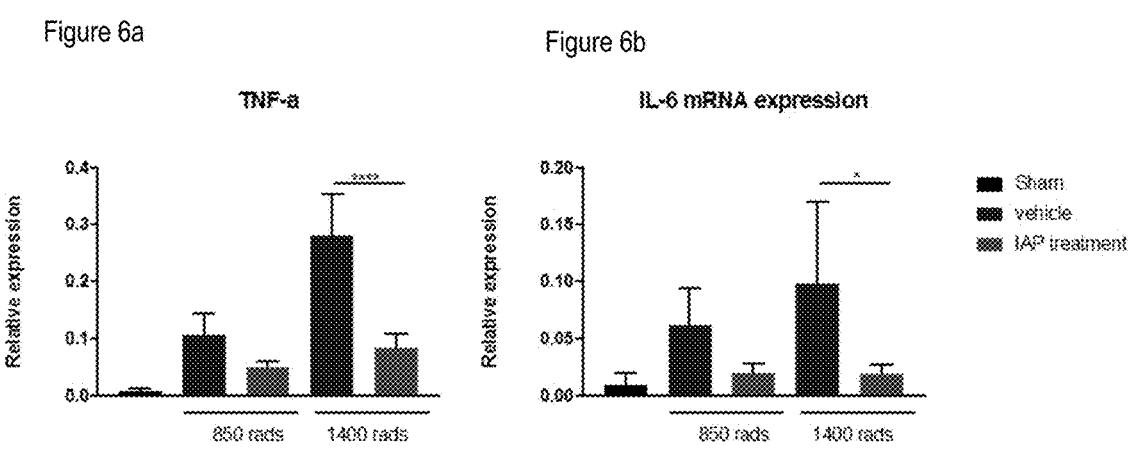
FIG. 6a-6b shows that IL-6 (FIG. 6b) and TNF-α (FIG. 6a) levels were decreased in ileums of irradiated mice (850 and 1400 rads) that received IAP treatment, as compared to irradiated mice that received vehicle. In all panels, the left-most bar represents the sham data; the left bar within the 850 rad cohort represents vehicle data, while the right bar represents IAP data; and the left bar within the 1400 rad cohort represents vehicle data, while the right bar represents IAP data.

Radiation-induced gut inflammation was assessed by measuring relative mRNA levels of IL1-6 and TNF in the colon and by measuring relative mRNA levels of IL-6 and TNF-a in the ileum of sacrificed mice. FIG. 5 shows that IL1-6 and TNF levels were decreased in colons of irradiated mice (850 and 1400 rads) that received IAP treatment, as compared to irradiated mice that received vehicle. FIG. 6 shows that IL-6 and TNF-a levels were decreased in ileums of irradiated mice (850 and 1400 rads) that received IAP treatment, as compared to irradiated mice that received vehicle.

Figure 7:
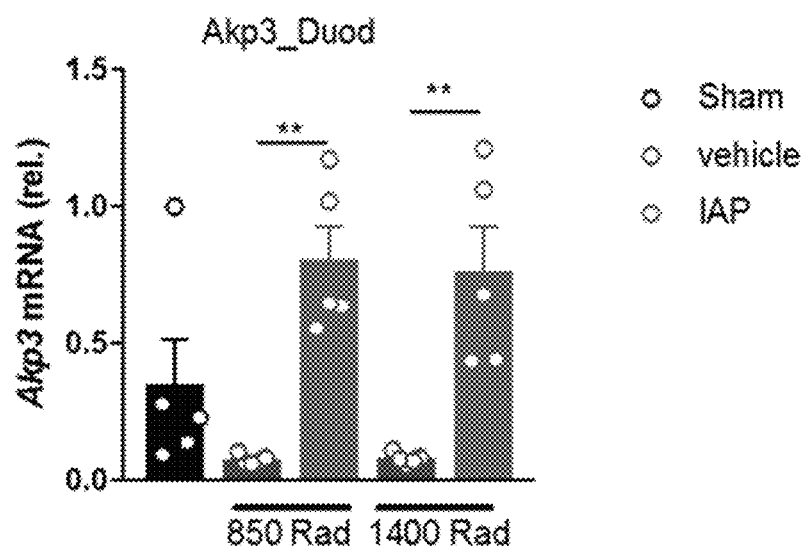
FIG. 7 shows IAP levels (Akp3 gene) were decreased in irradiated mice that received 850 or 1400 rads of total body irradiation and that received vehicle treatment, as compared to mice that did not receive radiation. In all panels, the left-most bar represents the sham data; the left bar within the 850 rad cohort represents vehicle data, while the right bar represents IAP data; and the left bar within the 1400 rad cohort represents vehicle data, while the right bar represents IAP data.

IAP expression in the duodenum was measured to determine the effects of radiation. Relative mRNA levels of IAP (Akp3 gene) were measured in the duodenum of sacrificed mice. FIG. 7 shows that Akp3 levels were decreased in irradiated mice (850 and 1400 rads) that received vehicle treatment, as compared to mice that did not receive radiation. However, as shown in FIG. 7, administration of exogenous IAP induced increased expression of Akp3 levels.

Example 8: IAP Prevents Gut Barrier Breakdown and Reduces Local and Systemic Inflammation in Murine Model of Radiation Enteritis This experiment was performed in order to assess the effect of IAP on maintaining gut barrier integrity after total body irradiation with a dose of 850 rads.

All C57BL/6 mice were administered a single dose of whole body irradiation of using a Cesium-137 irradiator (54 rads/minute) to a total dose of 850 rads. In the treatment group (n=5), IAP (SYN BIAPII) was given by supplementation in the drinking water at a concentration of 100 U/mL. IAP-treated mice had their drinking water supplemented for 4 days prior to irradiation and for 4 days after irradiation, at which point they were euthanized for tissue harvesting. Control mice (n=5) received radiation with no IAP (vehicle only) in their drinking water. An additional control group of sham irradiated mice (n=5) underwent all procedures except for irradiation.

In Vivo Intestinal Permeability Assay

For the assessment of the intestinal barrier function, mice were analyzed 4 days after irradiation. Approximately 4 hours prior to euthanasia, mice were gavaged with 0.2 mL of Fluorescein Isothiocyanate-Dextran (FITC-Dextran) (Sigma; St. Louis, MO, USA; 3-5 kDa, product number: FD4) in PBS, so that a dose of 440 mg/kg body weight was achieved. Aseptic cardiac puncture was performed to obtain blood samples. The collected blood was kept on ice and then centrifuged at 2,500×g for 10 minutes. The serum was removed and was then used to determine serum FITC levels with fluorescent spectrophotometry (excitation: 485 nm and emission: 528 nm).

Tissue Harvesting

Immediately after euthanasia, the mesenteric lymph nodes (MLNs), duodenum, ileum and colon were aseptically harvested through midline laparotomy. The intestine samples were flushed three times with sterile PBS. The The samples were then snap frozen in liquid nitrogen or stored in RNA-Later™ (QIAGEN; Manchester, UK) and were then frozen at −80° C. for future analysis.

Stool Samples

Stool pellets were collected at the time of euthanasia. The samples were homogenized in sterile PBS, centrifuged at 10,000g and the supernatant was used for phosphatase activity assay. This was done by adding 25 µL of supernatant to 175 µL of 5 mM p-nitrophenyl phosphate and using a spectrophotometer to measure changes in OD405 over time. Phosphatase activity was standardized to protein concentration and calculated as ng PNPP metabolized/minute/pg protein. Additionally, stool supernatant was assayed for fecal lipocalin-2 using the Duoset ELISA kit (R&D Systems; Minneapolis, MN, USA).

CFU Assessment

The mesenteric lymph node (MLN) tissue was used to assess bacterial translocation from the intestinal lumen. MLNs were homogenized in sterile PBS using metallic beads and were serially diluted 1/10-1/1000 and plated on LB agar plates. Systemic blood obtained via cardiac puncture, as described above, was used to assess bacteremia and was serially diluted 1/10-1/1000 in sterile PBS and plated on LB agar plates. Following inoculation, all plates were incubated at 37° C. and CFUs were quantified after 24 hours.

Real Time-Quantitative Polymerase Chain Reaction (RT-qPCR)

The duodenum, distal ileum and distal colon tissues were harvested and stored in RNA-Later™ at −80° C. as described above. RNA was isolated using Trizol™ (Thermo Fisher, Carlsbad, CA) according to the manufacturer's protocol. cDNA was generated using the iScript™ Reverse Transcription Supermix for RT-qPCR (BIO-RAD; Hercules, CA, USA), according to the manufacturer's instructions. RT-qPCR was performed using the Brilliant II SYBR® Green qPCR Master Mix with Low ROX (Agilent 600830; Agilent Technologies; Santa Clara, CA, USA). The total volume per reaction was 10 µL, consisting of 5 L SYBR® Green qPCR Master Mix with Low ROX, 0.1 µL forward primer (5 uM), 0.1 µL reverse primer (5 uM), 2.8 µL distilled water and 2 µL cDNA sample (pre-diluted to 1/5). The cycling conditions were as follows: 95° C. for 10 minutes (1 cycle); 95° C. for 30 minutes (40 cycles); 58° C. for 1 minute (40 cycles); 72° C. for 1 minute (40 cycles). Expression of specific genes were compared to the housekeeping gene Glyceraldehyde Dehydrogenase (GAPDH) using the $\Delta\Delta$Ct method. The average copy number of mRNA expression in control samples was set to 1.0.

The following forward ("F") and reverse ("R") primers were utilized during RT-qPCR experiments:

| Gene | Sequence |
|------|----------|
| Akp3 | F: CATGGACCGCTTCCCATA (SEQ ID NO: 19); R: CTTGCACTGTCTGGAACCTG (SEQ ID NO: 20) |
| Lactase | F: CAGCGATGCCCACAGGAAAG (SEQ ID NO: 21); R: ACGGAGCCCTTGACGAGAG (SEQ ID NO: 22) |
| Sucrase | F: CGTTTCCGGTTCAAGCTCAC (SEQ ID NO: 23); R: CCTGATGACTTTGATGCTGAACG (SEQ ID NO: 24) |
| TNF-α | F: ACTCCTTCTGTGACTCCAGC (SEQ ID NO: 25); R: ATAACTGCACCCACTTCCCA (SEQ ID NO: 26) |
| IL-1 | F: GCACTACAGGCTCCGAGATGAAC (SEQ ID NO: 27); R: TTGTCGTTGCTTGGTTCTCCTTGT (SEQ ID NO: 28) |
| IL-6 | F: CCTCTGGTCTTCTGGAGTACC (SEQ ID NO: 29); R: ACTCCTTCTGTGACTCCAGC (SEQ ID NO: 30) |
| IL-17 | F: TCTCCACCGCAATGAAGACC (SEQ ID NO: 31); R: CACACCCACCAGCATCTTCT (SEQ ID NO: 32) |
| ZO1 | F: GCTAAGAGCACAGCAATGGA (SEQ ID NO: 33); R: GCATGTTCAACGTTATCCAT (SEQ ID NO: 34) |
| ZO3 | F: CACGCAATCCTGGATGTCA (SEQ ID NO: 35); R: GTCGCGCCTGCTGTTGCT (SEQ ID NO: 36) |
| Occludin | F: CCCCATCTGACTATGTGGAAAGA (SEQ ID NO: 37); R: AAAACCGCTTGTCATTCACTTTG (SEQ ID NO: 38) |
| GAPDH | F: CAGGAGCGAGACCCCACTAACAT (SEQ ID NO: 39); R: GTCAGATCCACGACGGACACATT (SEQ ID NO: 40) |

Systemic Cytokine Assessment

Serum TNF-α and IL-6 were quantified using the mouse TNF alpha ELISA Ready-SET-Go kit (eBioscience; San Diego, CA, USA) and the Mouse IL-6 DuoSet ELISA (R&D Systems; Minneapolis, MN, USA) respectively, as per the manufacturer's instructions.

Endotoxin Quantification

Serum lipopolysaccharide (LPS) levels were determined using a commercially available Limulus Amebocyte Lysate (LAL) assay kit (Pierce Chromogen Endotoxin Quant kit, Thermo Scientific, Carlsbad, CA), following the manufacturer's instructions.

Assessment of Histologic Injury

The degree of injury was assessed in mice 4 days after radiation at the time of procurement. A radiation injury scoring system described by others was utilized to blindly score 2 sections per intestinal segment from each animal. Histologic abnormalities were graded as follows. grade 0, normal; grade 1, infiltration of inflammatory cells or mucosal hemorrhage; grade 2, vacuolization of the villi, abnormally oriented crypts, or mucosal hypertrophy; grade 3, submucosal cysts or irregular crypt regeneration with atypical epithelial cells; and grade 4, ulcerated mucosa or necrosis.

Statistical Analysis

Triplicate samples were used for all assays and all experiments were repeated at least three times, using 5 mice in each group. The statistical significance among groups was determined using one-way analysis of variance (ANOVA), with multiple post-hoc comparisons using Tukey's test, or two-way ANOVA analysis, using Bonferroni post-hoc test, as indicated (Graphpad Prism software, La Jolla, CA, USA). A $P<0.05$ was considered statistically significant. One star (*) denotes $P<0.05$; two stars () denote $P<0.01$; three stars (*) denote $P<0.001$.

Results

Irradiation Insult

After total-body irradiation, all mice in both the IAP and control treatment groups lost 20% of their starting body weight by post-irradiation day 4 ($p=0.3$). Mice in both IAP and control-treated irradiation groups ate similar amounts of food as compared to the sham-irradiated mice (4.9 vs 4.8 vs 4.75 g/day/mouse).

Administration of IAP Maintains the Gut Barrier after Irradiation

The gut barrier was first analyzed by measuring the flux of 4 kDa FITC-Dextran across the epithelium into the bloodstream, which is a standard measure of paracellular permeability. Compared to controls, irradiated mice had a 10-fold increase in serum FITC ($p<0.001$, FIG. 8a). Enteral supplementation with IAP reduced serum FITC by approximately 80% in irradiated mice, indicating that IAP had maintained the gut barrier and attenuated paracellular permeability.

The role of expression of tight junction proteins was then determined using real-time qPCR. Gene expression of ZO1, ZO3, and occludin in a segment of ileum were significantly decreased as a result of radiation. FIG. 8b and FIG. 8c show that IAP supplementation restored ZO1 expression to 90% of control ($p<0.001$) and partially restored ZO3. Similarly, ZO1, ZO3, and occludin measured in a segment of colon tissue were also significantly decreased after radiation therapy. This observed decrease in TJP protein expression in the colon was again attenuated by IAP. Specifically, as shown in FIG. 8d and FIG. 8e, ZO3 and occludin expression were increased from 28% to 47% of control ($P<0.05$) and 39% to 78% of control ($p<0.05$) respectively.

Histologic Injury

Figure 9A:
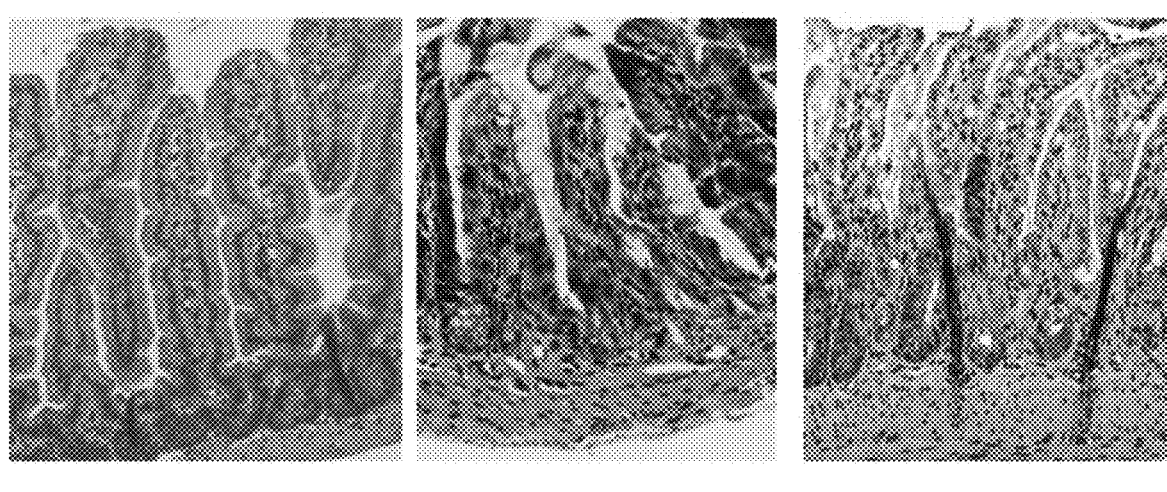
FIG. 9a-9b depicts H&E-stained unirradiated control ileal tissue was compared with irradiated ileal tissue with and without supplemental, enteral IAP (FIG. 9a) and compared with irradiated ileal tissue with vehicle (FIG. 9b) four days after irradiation.
Figure 9B:
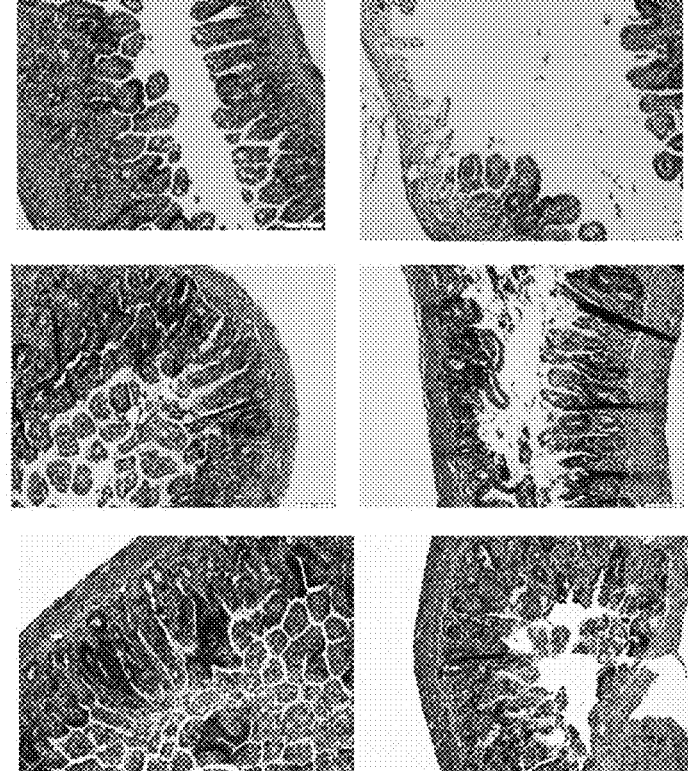

Four days after irradiation, H&E-stained unirradiated control ileal tissue was compared with irradiated ileal tissue with and without supplemental, enteral IAP (FIG. 9a) and compared with irradiated ileal tissue with vehicle (FIG. 9b). Irradiation resulted in obvious intestinal injury with all intestinal segments from this cohort of mice scoring >3 on histologic scoring, compared to a score of 0 for all controls. The degree of injury decreased after enteral IAP administration, with an average severity score of 2.3.

Administration of IAP Reduces Local and Systemic Inflammatory Cytokines

Figure 10A:
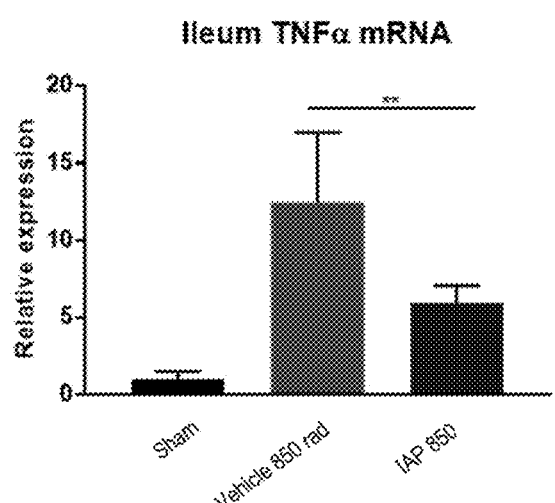
FIG. 10a-10c shows gene expression of pro-inflammatory cytokines in the ileum and colon using real time PCR. Compared to sham irradiated mice.
Figure 10B:
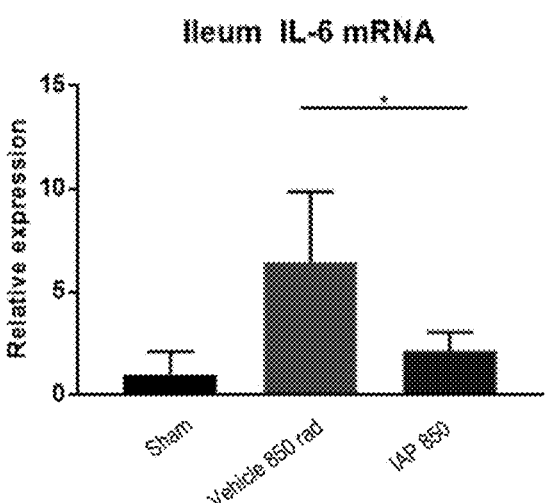
Figure 10C:
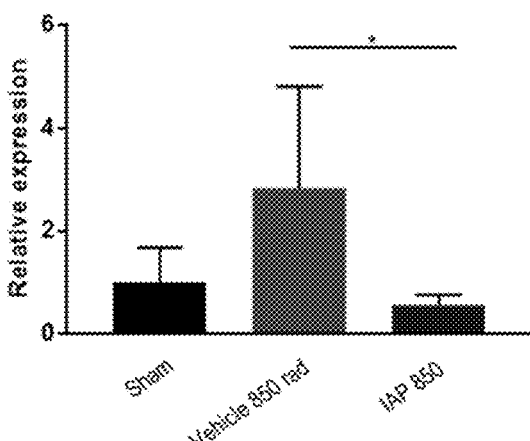

Gene expression of pro-inflammatory cytokines in the ileum and colon were analyzed using real time PCR. Compared to sham irradiated mice, FIG. 10a shows that irradiated mice had a 13-fold increase in TNF-α which was reduced 50% by IAP supplementation ($p<0.001$). Similarly, irradiated mice had a 6-fold increase in IL-6 levels (FIG. 10b), a 4.5-fold increase in IL-1β, and a 2.8-fold increase in IL-17 (FIG. 10c). IAP supplementation attenuated expression of these pro-inflammatory cytokines by 67%, 67%, and 33% respectively ($p<0.05$). More distally in the colon, FIG. 11a-b shows that irradiation treatment increased TNF-α expression 15-fold (FIG. 11a) and IL-1p 8-fold (FIG. 11b), enteral IAP similarly reduced expression of these cytokines by 80% and 75%, respectively ($p<0.05$).

Given the reduction in pro-inflammatory cytokine expression at the local intestinal tissue level, it was then determined if there was a difference in circulating cytokine levels. Irradiated mice had significantly higher systemic levels of both TNF-α and IL-6 in the serum ($p<0.05$), as shown in FIG. 12a-b. IAP treatment significantly decreased TNF-α when compared to irradiated mice that did not receive IAP (17.5 vs 13.3 μg/mL, $p<0.05$). It was additionally observed that IAP decreased systemic serum IL-6 levels; however, this did not reach statistical significance (32.2 vs 23.9 μg/mL, $p=0.08$).

Irradiation Decreases Endogenous Brush Border Enzyme Expression

Figure 13:
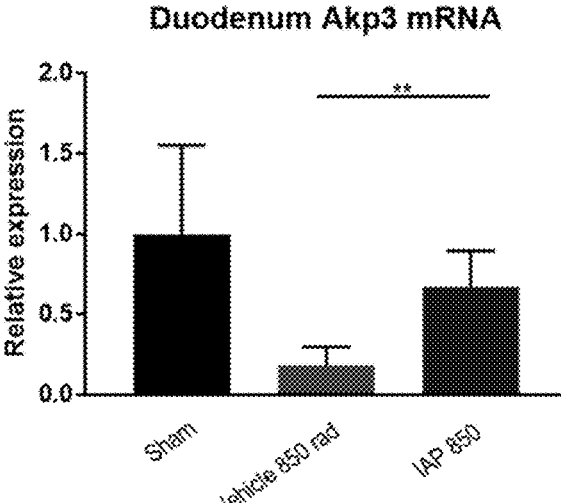
FIG. 13 depicts the effect of irradiation on gene expression of endogenous IAP (Akp3). Supplemental enteral IAP restored endogenous IAP expression back to 67% of control mice (p=0.002).
Figure 14A:
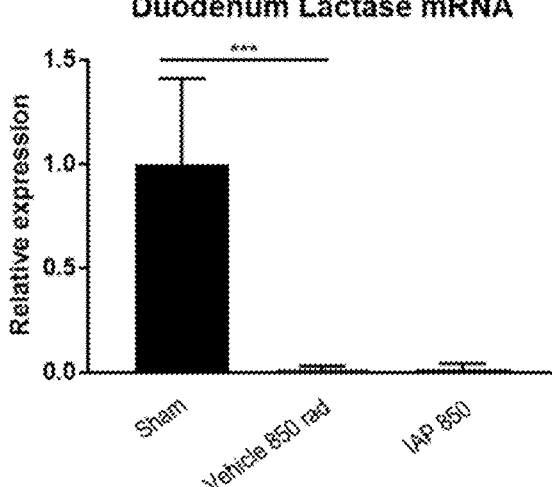
FIG. 14a-14b depicts duodenal expression of other common brush border enzymes in order to determine if IAP would also have an effect. It was found that irradiation nearly eliminated expression of lactase (p<0.001), as shown in FIG. 14a, and decreased expression of sucrase by 80% (p=0.06), as shown in FIG. 14b.
Figure 14B:
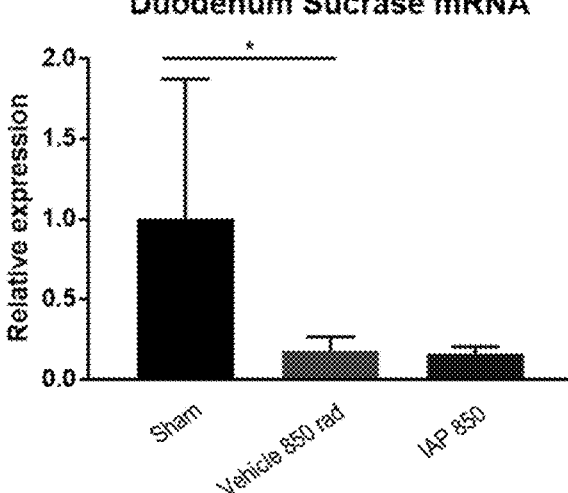
Figure 15:
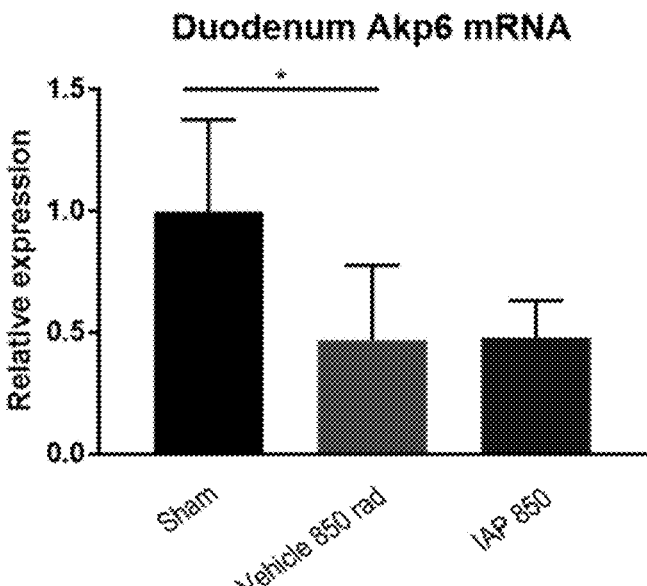
FIG. 15 shows that irradiation decreased Akp6 expression in the duodenum by 50% (p<0.05).

Given the ability of IAP to maintain the gut barrier and reduce local and systemic inflammation after irradiation treatment, it was next determined if there was an effect of irradiation therapy on endogenous IAP expression. IAP is primarily produced in the proximal gastrointestinal tract; therefore, duodenal tissue was analyzed for gene expression of IAP and other brush border enzymes. Irradiation treatment decreased endogenous IAP expression by approximately 80%. Interestingly, supplemental enteral IAP restored endogenous IAP expression back to 67% of control mice ($p=0.002$), as shown in FIG. 13. To determine if this effect was specific to IAP, duodenal expression of other common brush border enzymes was analyzed and found that irradiation nearly eliminated expression of lactase ($p<0.001$), as shown in FIG. 14a, and decreased expression of sucrase by 80% ($p=0.06$), as shown in FIG. 14b. In contrast to the endogenous IAP levels, neither of these enzymes were restored with IAP supplementation. Lastly, expression of another alkaline phosphatase, Akp6, which, unlike IAP, is expressed throughout the intestinal tract, was analyzed but has significantly less phosphatase activity. Irradiation decreased Akp6 expression in the duodenum by 50% ($p<0.05$), as shown in FIG. 15; however, IAP supplementation did not attenuate this decrease. Despite the decrease in Akp3 and Akp6 gene transcription, no differences were observed in stool phosphatase activity between groups (137 vs 196 vs 156 ng PNPP/min/ug protein, $p=0.3$).

Irradiation Did not Increase Systemic LPS or Bacteremia

Breakdown of the gut barrier allows for potential translocation of pathogens and their byproducts. Despite the observed barrier dysfunction with translocation of FITC-dextran into systemic circulation, there was no difference in serum LPS when comparing irradiated mice to control mice, and no bacteria were able to be cultured from either the mesenteric lymph nodes or serum from any of the groups.

CONCLUSIONS

IAP appears to be potentially beneficial in preventing the gut barrier breakdown as well as both local and systemic inflammation in a murine model of radiation enteritis. Taken together with data from other studies, there is evidence to support future clinical trials of the efficacy of IAP in preventing radiation enteritis in human patients.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g., additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays or measurements or methane production in stool samples. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

The following references are incorporated by reference herein in their entireties:

Alam, S N, Yammine, H, Moaven, O, Ahmed, R., Moss, A K, Biswas, B, Muhammad, N, Biswas, R, Raychowdhury, A, Kaliannan, K, Ghosh, S, Ray, M, Hamarneh, S, Barua, S, Malo, N S, Bhan, A K, Malo, MS<Hodin, R A. (2014). Intestinal alkaline phosphatase prevents antibiotic-induced susceptibility to enteric pathogens. Ann Surg. 259: 715-722.

Aldag, I, Bockau, U, Rossdorf, J, Laarmann, S, Raaben, W, Hermann, L, Weide, T, Hartman M W W. (2011). Expression, secretion and surface display of a human alkaline phosphatase by the ciliate Tetrahymena thermophilia. BMC Biotechnology 11:11.

Barreera, D J, Rosenberg, J N, Chiu, J G, Chang, Y-N, Debatis, M, Ngoi, S-M, Chang, J T, Shoemaker, C B, Oyler, G A, Mayfield, S P. (2014). Algal chloroplast produced camelid VhH antitoxins are capable of neutralizing botulinum neurotoxin. Plant Biotechnology J. doi: 10.1111/pbi.12244.

Becerra-Arteaga, A, Mason, HS<Shuler, M L. (2006). Production, secretion, and stability of human secreted alkaline phosphatase in tobacco NT1 cell suspension cultures. Biotechnol. Prog. 22:1643-1649.

Beck, R, Burtscher, H. (1994). Expression of human placental alkaline phosphatase in Escherichia coli. Protein Expr. Purif. 5:192-197.

Berger, J, Howard, A D, Gerger, L, Cullen, B R, Udenfriend, S. (1987). Expression of active, membrane-bound human placental alkaline phosphatase by transfected simian cells. Proc. Natl. Acad. Sci USA 84:4885-4889.

Bretthauer, R K, Castellino, F J. (1999). Glycosylation of Pichia pastoris-derived proteins. Biotechnol. Appl. Biochem. 30:193-200.

Broz, A, Huang, N, Unruh, G. (2013). Plant-based protein biomanufacturing. www.genengnews.com/gen-articles/ plant-based-protein-biomanufacturing/4734/

Chen, K T., Malo, M S., Moss, A K., Zeller, S., Johnson, P., Ebrahimi, F., Mostafa, G., Alam, S N., Ramasamy, S., Warren, H S., Hohmann, E L., Hodin, R A. (2010) Identification of specific targets for the gut mucosal defense factor intestinal alkaline phosphatase. Am J Physiol Gastrointest Liver Physiol 299, G467-G475.

Cui, M, Xiao, H, Li, Y, Zhou, L, Zhao, S, Luo, D, Zheng, Q, Dong, J, Zhao, Y, Zhang, X, Zhang, J, Lu, L, Wang, H, Fan, S (2017). Faecal microbiota transplantation protects against radiation-induced toxicity. EMBO Molecular Medicine 9(4):448-461.

Edwards-Ingram, L, Gitsham, P, Burton, N, Warhurst, g, Clarke, I, Hoyle, D, Oliver, S G, Stateva, L. (2007). Genotypic and physiological characterization of Saccha-romyces boulardii, the probiotic strain of Saccharomyces cerevisiae. Appl. Environ. Microbiol. 73:2458.

Flagfeldt, D B, Siewers, V, Huang, L, Nielsen, J. (2009). Characterization of chromosomal integration sites for heterologous gene expression in Saccharomyces cerevisiae. Yeast 26:545.

Gomord, V Faye, L. (2004). Posttranslational modification of therapeutic proteins in plants. Curr. Opin. Plant Biol. 7:171-181

Graff, S, Chaumeil, J-C, Boy, P, Lai-Kuen, R, Charrueau, C. (2008). Influence of pH conditions on the viability of Saccharomyces boulardii yeast. J. Gen. Appl. Microbiol. 54:221-227.

Gregory, J A, Topol, A B, Doerner, D Z, Mayfield, S. (2013). Alga-produced cholera toxin-Pfs25 fusion proteins as oral vaccines. Appl. Environ. Microbiol. 79:3917-3925.

Hatoum R, Labrie, St, Fliss, I. (2012). Antimicrobial and probiotic properties of yeasts: from fundamental to novel applications. Frontiers in Microbiology 3: 421-421.

Hauer-Jensen, M, Denham, J, Andreyev, H. (2014). Radiation enteropathy—pathogenesis, treatment, and prevention. Nat Rev Gastroenterol Hepatol. 11(8): 470-479.

Heimo, H K, Palmu, K, Suominen, I. (1998). Human placental alkaline phosphatase: expression in Pichia pastoris, purification and characterization of the enzyme. Protein Expr. Purif. 12:85-92.

Kaliannana, K., Hamarneha, S R., Economopoulosa, K P., Alama, S N., Moavena, O., Patela, P., Maloa, N S., Raya, M., Abtahia, S M., Muhammada, N., Raychowdhurya, A., Teshagera, A., Mohameda, MMR., Mossa, A K., Ahmeda, R., Hakimiana, S., Narisawab, S., Millàn, J L., Hohmannc, E., Warrenc, H S., Bhand, A K., Maloa, M S., Hodina, R A. (2013) Intestinal alkaline phosphatase prevents metabolic syndrome in mice. PNAS 7003-7008.

Klein, S M, Elmer, G W, McFarland, L V, Surawicz, C M, Levy, R H. (1993). Recovery and elimination of the biotehrapeutic agent, Saccharomyces boulardii, in healthy human volunteers. Pharm Res. 10:1615-1619.

Komarnytsky, S., Borisjuk, N V, Borisjuk, L G., Alam, M Z, Raskin, I. (2000). Production of recombinant proteins in tobacco guttation fluid. Plant Physiol. 124:927-933.

Le Du, M-H., Lamoure, C., Muller, B-H., Bulgakov, O V., Lajeunesse, E., Menez, A., Boulain, J-C. Artificial evolution of an enzyme active site: structural studies of three highly active mutants of Escherichia coli alkaline phosphatase (2002). J. Mol. Biol. 316, 941-953.

Leung, D., Chen, E., Goeddel, D., A method for random mutagenesis of a defined DNA segment using a modified polymerase chain reaction (1989). Technique 1, 11-15.

Lorimer, I A, Pastan, I. (1995). Random recombination of antibody single change Fv sequences after fragmentation with DNaseI in the presence of Mn2+. Nucleic Acids. Res. 23:3067-3068.

Lin-Cereghino, J, Wong, W W, Xiong, S, Giang, W, Luong, L T, Vu, J, Johnson, S D, Lin-Cereghino, G P. (2005). Condensed protocol for competent cell preparation and transformation of the methylotrophic yeast Pichia pastoris. Biotechniques, 38, 44, 46, 48.

Malo, M S, Alam, S N, Mostafa, G, Zeller, S J, Johnson, P V, Mohammad, N, Chen, K T, Moss, A K, Ramasamy, S, Faruqui, A, Hodin, S, Malo, P S, Ebrahimi, F, Biswas, B, Narisawa, S, Millan, J L, Warren, H S, Kaplan, J B, Kitts, C L, Hohmann, El, Hodin, R A. (2010). Intestinal alkaline phosphatase preserves the normal homeostasis of gut microbiota. Gut, 59:1476-1484.

Manes, T, Hoylaerts, M F, Muller, R, Lottspeich, F, Hoke, Millan, J L. (1998). Genetic complexity, structure, and characterization of highly active bovine intestinal alkaline phosphatases. J. Biol. Chem., 273:23353-23360.

Manuell, A L, Beligni, MV<Elder, J H, Siefker, D T, Tran, M, Weber, A, McDonald, T L, Mayfield, S P (2007). Robust expression of a bioactive mammalian protein in Chlamydomonas chloroplast. Plant Biotechnol. J. 5:402-412.

McCoullough, M J, Clemons, K V, McCusker, J H, Stevens, D A. (1998). Species indentification and virulence attributes of Saccharomyces boulardii. J. Clin. Microbiol. 36:2613.

Mellitzer, A, Ruth, C, Gustaffson, C, Welch, M, Girner-Brunberger, R, Weis, R, Purkarthofer, T, Glieder, A. (2014). Synergistic modular promoter and gene optimization to push cellulose secretion by Pichia pastoris beyond existing benchmarks. J. Biotechnology 191:187-95.

Millan, J L. Mammalian alkaline Phosphatases. Wiley-VCH Verlag GmbH & Co. 2006.

Moore, J C, Arnold, F H. (1996). Directed evolution of a para-nitrobenzyl esterase for aqueous-organic solvents. Nat. Biotechnol. 14:458-467

Muller, B H., Lamoure, C., Le Du, M-H., Cattolico, L., Lajeunesse, E., Lemaitre, F., Pearson, A., Ducancel, F., Menez, A., Boulain, J-C. Improving Escherichia coli alkaline phosphatase efficacy by additional mutations inside and outside the catalytic pocket (2001). Chembiochem. 2, 517-523.

Murphy, J E., Kantrowitz, E R. Why are mammalian alkaline phosphatases much more active than bacterial alkaline phosphatases? (1994) Molecular Microbiology. 12, 351-357.

Musiychuk, K, Stephenson, N, Bi, H, Farrance, C E, Orozovic, G, Brodelius, M, Brodelius, P, Horsey, A, Ugulava, N, Shamloul, A-M, Mett, V, Rabindran, S., Streatfield, S J, Yusibov, V. (2007). A launch vector for the production of vaccine antigens in plants. Influenza and Other Respiratory Viruses, 1:19-25.

Oda, K, Amaya, Y, Fukushi-Irie, M, Kinameri, Y, Ohsuye, K, Kubota, I, Fujimura, S, Kobayashi, J. (1999). A general method for rapid purification of soluble versions of glycosylphosphatidylinositol-anchored proteins expressed in insect cells: an application for human tissue-nonspecific alkaline phosphatase. J. Biochem. 126:694-699.

Orlean, P, Menon, A K. (2007). GPI anchoring of protein in yeast and mammalian cells, or: how we learned to stop worrying and love glycophospholipids. J. Lipid Res. 48:993-1011.

Pfitzner, U M, Goodman, H M. (1987). Isolation and characterization of cDNA clones encoding pathogenesis-related proteins from tobacco mosaic virus infected tobacco plants. Nucleic Acids Res. 15:4449-4465.

Rasals, B S, Muto, M, Lee, P A, Jager, M, Cardoso, R M F, Behnke, C A, Kirk, P, Hokanson, C A, Crea, R, Mendez, M, Mayfield, S P (2010). Production of therapeutic proteins in algae, analysis of expression of seven human proteins in the chloroplast of Chlamydomonas reinhardtii. Plant Biotechnol. J. 8:719-733.

Rieder, F, Kessler, S, Sans, M, Fiocchi, C (2012). Animal models of intestinal fibrosis: new tools for the understanding of pathogenesis and therapy of human disease. Am J Physiol Gastrointest Liver Physiol 303:G768-G801.

Shaaltiel, Y, Bartfeld, D, Hasmueli, S, Baum, G, Brill-Almon, E, Galili, G, Dym, O, Boldin-Ada, sky. S A. Silman, I, Sussman, J L, Futerman, A H, Aviezer, D. (2007). Production of glucocerebrosidase with terminal mannos glycans for enzyme replacement therapy of Gaucher's disease using a plant cell system. Plant Biotechnol. J., 5:579-590.

Shamloul, M, Trusa, J, Mett, V, Yusibov, V. (2014). Optimization and utilization of Agrobacterium-mediated transient protein production in Nicotiana. J. of Visualized Experiments, doi.10.3791/51204.

Specht, E, Miyake-Stoner, S, Mayfield, S. (2010). Microalgae come of age as a platform for recombinant protein production. Biotechnol. Lett. 32:1373-1383.

Stemmer, W. P. C. (1994a) "DNA Shuffling by random fragmentation and reassembly: In vitro recombination for molecular evolution", Proc. Natl. Acad. Sci. USA 91, 10747/10751.

Tran, M, Van, C, Barrera, D J, Pettersson, P L, Peinado, C D, Bui, J. Mayfield, S P. (2013). Production of unique immunotoxin cancer therapeutics in algal chloroplasts. Proc. Natl. Acad. Sci. USA 110:E15-E22.

Wandelt, C I, Khan, M R, Craig, S, Schroeder, H E, Spencer, D, Higgins, T J. (1992). Vicilin with carboxy-termina KDEL is retained in the endoplasmic reticulum and accumulates to high levels in the leaves of transgenic plants. Plant J. 2:181-192.

Xu, H F., Zhang, X E., Zhang, Z P., Zhang, Y M., Cass, AEG (2003). Directed Evolution of E. coli Alkaline Phosphatase Towards Higher Catalytic Activity. Biocatalysis and Biotransformation. 21, 41-47.

Zhang, D, Nandi, S, Bryan, P, Pettit, S, Nguyen, D, Santos, M A, Huang, N. (2010). Expression, purification, and characterization of recombinant human transferrin from rice (Oryza sativa L.). Protein Expr. Purif. 74:69-79.

Zhang, F., Murhammer, D S, Linhardt, R J. (2002). Enzyme kinetics and glycan structural characterization of secreted alkaline phosphatase prepared using the baculovirus expression vector system. Appl. Biochem. Biotechnol. 101:197-210.

Zhang, Y X, Zhu, Y, Xi, H W, Liu, Y L, Zhou, H M. (2002). Refolding and reactivation of calf intestinal alkaline phosphatase with excess magnesium ions. Int. J. Biochem. Cell. Biol. 34:1241-1247.

The invention claimed is:

1. A method of treating or preventing acute radiation enteropathy in a subject in need thereof, the method comprising administering to the subject an intestinal alkaline phosphatase (IAP), wherein the IAP comprises the amino acid sequence of SEQ ID NO: 2 or SEQ ID NO: 3, and wherein the acute radiation enteropathy comprises one of more of gastrointestinal syndrome, hematopoietic syndrome, neurovascular syndrome, and ionizing radiation induced apoptosis tissue damage.

2. The method of claim 1, wherein the acute radiation enteropathy occurs within the first 3 months after radiation exposure.

3. The method of claim 1, wherein the acute radiation enteropathy occurs within the first 2 months after radiation exposure.

4. The method of claim 1, wherein the acute radiation enteropathy occurs within the first month after radiation exposure.

5. The method of claim 1, wherein the acute radiation enteropathy comprises one or more of nausea, vomiting, stomach cramping, frequent urges to use the bathroom, watery diarrhea, mucous discharge from the rectum, rectal pain, rectal bleeding, weight loss, wave-like stomach pains, damage to the epithelial surfaces, moist desquamation, pel-vic radiation disease, radiation proctitis, urgency, radiation cystitis, intestinal discomfort, soreness, and mouth, throat and stomach sores.

6. The method of claim 1, wherein the radiation comprises one or more of ionizing radiation, X-rays, gamma rays, and charged particles.

7. The method of claim 1, wherein the subject is a cancer patient.

8. The method of claim 1, wherein the acute radiation enteropathy is a side effect of radiotherapy.

9. The method of claim 8, wherein the radiotherapy is delivered as an external-beam radiation therapy selected from 3-dimensional conformal radiation therapy (3D-CRT), intensity-modulated radiation therapy (IMRT), image-guided radiation therapy (IGRT), electromagnetic-guided radiation therapy tomotherapy, stereotactic radiosurgery (SRS), stereotactic body radiation therapy (SBRT), intraoperative radiation therapy (IORT), and proton therapy.

10. The method of claim 8, wherein the radiotherapy is delivered as a brachytherapy selected from interstitial brachytherapy, intracavitary brachytherapy, and episcleral brachytherapy.

11. The method of claim 8, wherein the radiotherapy is delivered as a systemic radiation therapy selected from a radioactive iodine and a radioactive biologic.

12. The method of claim 1, wherein the acute radiation enteropathy is a result of a high dose of radiation.

13. The method of claim 12, wherein the high dose of radiation is about 5 Gy to about 30 Gy.

14. The method of claim 1, wherein prior to the administration of the IAP, the subject's lymphocyte count is less than about 1000 cells/μL.

15. The method of claim 1, wherein the IAP is formulated for oral administration.

\* \* \* \* \*

SEQUENCE LISTING

Sequence total quantity: 60
SEQ ID NO: 1              moltype = AA   length = 528
FEATURE                  Location/Qualifiers
REGION                   1..528
                         note = Synthetic polymer
source                   1..528
                         mol_type = protein
                         organism = synthetic construct
SEQUENCE: 1
MQGPWVLLLL GLRLQLSLGV IPAEEENPAF WNRQAAEALD AAKKLQPIQK VAKNLILFLG   60
DGLGVPTVTA TRILKGQKNG KLGPETPLAM DRFPYLALSK TYNVDRQVPD SAATATAYLC  120

```
GVKANFQTIG LSAAARFNQC NTTRGNEVIS VMNRAKQAGK SVGVVTTTRV QHASPAGTYA   180
HTVNRNWYSD ADMPASARQE GCQDIATQLI SNMDIDVILG GGRKYMFPMG TPDPEYPADA   240
SQNGIRLDGK NLVQEWLAKH QGAWYVWNRT ELMQASLDQS VTHLMGLFEP GDTKYEIHRD   300
PTLDPSLMEM TEAALRLLSR NPRGFYLFVE GGRIDHGHHE GVAYQALTEA VMFDDAIERA   360
GQLTSEEDTL TLVTADHSHV FSFGGYTLRG SSIFGLAPSK AQDSKAYTSI LYGNGPGYVF   420
NSGVRPDVNE SESGSPDYQQ QAAVPLSSET HGGEDVAVFA RGPQAHLVHG VQEQSFVAHV   480
MAFAACLEPY TACDLAPPAC TTDAAHPVAA SLPLLAGTLL LLGASAAP              528

SEQ ID NO: 2            moltype = AA   length = 533
FEATURE                 Location/Qualifiers
REGION                  1..533
                        note = Synthetic polymer
source                  1..533
                        mol_type = protein
                        organism = synthetic construct
SEQUENCE: 2
MQGACVLLLL GLHLQLSLGL IPAEEENPAF WNRQAAQALD VAKKLQPIQT AAKNVILFLG   60
DGMGVPTVTA TRILKGQMNG KLGPETPLAM DQFPYVALSK TYNVDRQVPD SAGTATAYLC   120
GVKGNYRTIG VSAAARYNQC NTTRGNEVTS VINRAKKAGK AVGVVTTTRV QHASPAGAYA   180
HTVNRNWYSD ADLPADAQKN GCQDIAAQLV YNMDIDVILG GGRMYMFPEG TPDPEYPDDA   240
SVNGVRKDKQ NLVQEWQAKH QGAQYVWNRT ALLQAADDSS VTHLMGLFEP ADMKYNVQQD   300
HTKDPTLAEM TEAALQVLSR NPRGFYLFVE GGRIDHGHHD GKAYMALTEA IMFDNAIAKA   360
NELTSELDTL ILVTADHSHV FSFGGYTLRG TSIFGLAPGK ALDSKSYTSI LYGNGPGYAL   420
GGGSRPDVNG STSEEPSYRQ QAAVPLASET HGGEDVAVFA RGPQAHLVHG VQEETFVAHI   480
MAFAGCVEPY TDCNLPAPAT ATSIPDAAHL AASPPPLALL AGAMLLLLAP TLY          533

SEQ ID NO: 3            moltype = AA   length = 530
FEATURE                 Location/Qualifiers
REGION                  1..530
                        note = Synthetic polymer
source                  1..530
                        mol_type = protein
                        organism = synthetic construct
SEQUENCE: 3
MQWACVLLLL GLWLQLSLTF IPAEEEDPAF WNRQAAQALD VAKKLQPIQT AAKNVILFLG   60
DGMGVPTVTA TRILKGQMNG KLGPETPLAM DQFPYVALSK TYNVDRQVPD SAGTATAYLC   120
GVKGNYKTIG VSAAARYNQC NTTSGNEVTS VMNRAKKAGK SVGVVTTSRV QHASPAGAYA   180
HTVNRNWYSD ADLPADAQTY GCQDIATQLV NNMDIDVILG GGRMYMFPEG TPDPEYPYDV   240
NQTGVRKDKR NLVQEWQAKH QGAQYVWNRT ELLQAANDPS VTHLMGLFEP ADMKYNVQQD   300
PTKDPTLEEM TEAALQVLSR NPQGFYLFVE GGRIDHGHHE GKAYMALTDT VMFDNAIAKA   360
NELTSELDTL ILATADHSHV FSFGGYTLRG TSIFGLAPSK ASDNKSYTSI LYGNGPGYVL   420
GGGLRPDVND SISEDPSYRQ QAAVPLSSES HGGEDVAVFA RGPQAHLVHG VQEETFVAHV   480
MAFAGCVEPY TDCNLPAPSG LSDAAHLAAS PPSLALLAGA MLLLLAPALY            530

SEQ ID NO: 4            moltype = AA   length = 503
FEATURE                 Location/Qualifiers
REGION                  1..503
                        note = Synthetic polymer
source                  1..503
                        mol_type = protein
                        organism = synthetic construct
SEQUENCE: 4
MQGPWVLLLL GLRLQLSLGV IPAEEENPAF WNRQAAEALD AAKKLQPIQK VAKNLILFLG   60
DGLGVPTVTA TRILKGQKNG KLGPETPLAM DRFPYLALSK TYNVDRQVPD SAATATAYLC   120
GVKANFQTIG LSAAARFNQC NTTRGNEVIS VMNRAKQAGK SVGVVTTTRV QHASPAGTYA   180
HTVNRNWYSD ADMPASARQE GCQDIATQLI SNMDIDVILG GGRKYMFPMG TPDPEYPADA   240
SQNGIRLDGK NLVQEWLAKH QGAWYVWNRT ELMQASLDQS VTHLMGLFEP GDTKYEIHRD   300
PTLDPSLMEM TEAALRLLSR NPRGFYLFVE GGRIDHGHHE GVAYQALTEA VMFDDAIERA   360
GQLTSEEDTL TLVTADHSHV FSFGGYTLRG SSIFGLAPSK AQDSKAYTSI LYGNGPGYVF   420
NSGVRPDVNE SESGSPDYQQ QAAVPLSSET HGGEDVAVFA RGPQAHLVHG VQEQSFVAHV   480
MAFAACLEPY TACDLAPPAG TTD                                         503

SEQ ID NO: 5            moltype = AA   length = 506
FEATURE                 Location/Qualifiers
REGION                  1..506
                        note = Synthetic polymer
source                  1..506
                        mol_type = protein
                        organism = synthetic construct
SEQUENCE: 5
MQGACVLLLL GLHLQLSLGL IPAEEENPAF WNRQAAQALD VAKKLQPIQT AAKNVILFLG   60
DGMGVPTVTA TRILKGQMNG KLGPETPLAM DQFPYVALSK TYNVDRQVPD SAGTATAYLC   120
GVKGNYRTIG VSAAARYNQC NTTRGNEVTS VINRAKKAGK AVGVVTTTRV QHASPAGAYA   180
HTVNRNWYSD ADLPADAQKN GCQDIAAQLV YNMDIDVILG GGRMYMFPEG TPDPEYPDDA   240
SVNGVRKDKQ NLVQEWQAKH QGAQYVWNRT ALLQAADDSS VTHLMGLFEP ADMKYNVQQD   300
HTKDPTLAEM TEAALQVLSR NPRGFYLFVE GGRIDHGHHD GKAYMALTEA IMFDNAIAKA   360
NELTSELDTL ILVTADHSHV FSFGGYTLRG TSIFGLAPGK ALDSKSYTSI LYGNGPGYAL   420
GGGSRPDVNG STSEEPSYRQ QAAVPLASET HGGEDVAVFA RGPQAHLVHG VQEETFVAHI   480
MAFAGCVEPY TDCNLPAPAT ATSIPD                                      506
```

-continued

```
SEQ ID NO: 6           moltype = AA  length = 503
FEATURE                Location/Qualifiers
REGION                 1..503
                       note = Synthetic polymer
source                 1..503
                       mol_type = protein
                       organism = synthetic construct
SEQUENCE: 6
MQWACVLLLL GLWLQLSLTF IPAEEEDPAF WNRQAAQALD VAKKLQPIQT AAKNVILFLG    60
DGMGVPTVTA TRILKGQMNG KLGPETPLAM DQFPYVALSK TYNVDRQVPD SAGTATAYLC   120
GVKGNYKTIG VSAAARYNQC NTTSGNEVTS VMNRAKKAGK SVGVVTTSRV QHASPAGAYA   180
HTVNRNWYSD ADLPADAQTY GCQDIATQLV NNMDIDVILG GGRMYMFPEG TPDPEYPYDV   240
NQTGVRKDKR NLVQEWQAKH QGAQYVWNRT ELLQAANDPS VTHLMGLFEP ADMKYNVQQD   300
PTKDPTLEEM TEAALQVLSR NPQGFYLFVE GGRIDHGHHE GKAYMALTDT VMFDNAIAKA   360
NELTSELDTL ILATADHSHV FSFGGYTLRG TSIFGLAPSK ASDNKSYTSI LYGNGPGYVL   420
GGGLRPDVND SISEDPSYRQ QAAVPLSSES HGGEDVAVFA RGPQAHLVHG VQEETFVAHV   480
MAFAGCVEPY TDCNLPAPSG LSD                                           503

SEQ ID NO: 7           moltype = AA  length = 508
FEATURE                Location/Qualifiers
REGION                 1..508
                       note = Synthetic polymer
source                 1..508
                       mol_type = protein
                       organism = synthetic construct
SEQUENCE: 7
MQWACVLLLL GLWLQLSLTF IPAEEEDPAF WNRQAAQALD VAKKLQPIQT AAKNVILFLG    60
DGMGVPTVTA TRILKGQMNG KLGPETPLAM DQFPYVALSK TYNVDRQVPD SAGTATAYLC   120
GVKGNYKTIG VSAAARYNQC NTTSGNEVTS VMNRAKKAGK SVGVVTTSRV QHASPAGAYA   180
HTVNRNWYSD ADLPADAQTY GCQDIATQLV NNMDIDVILG GGRMYMFPEG TPDPEYPYDV   240
NQTGVRKDKR NLVQEWQAKH QGAQYVWNRT ELLQAANDPS VTHLMGLFEP ADMKYNVQQD   300
PTKDPTLEEM TEAALQVLSR NPQGFYLFVE GGRIDHGHHE GKAYMALTDT VMFDNAIAKA   360
NELTSELDTL ILATADHSHV FSFGGYTLRG TSIFGLAPSK ASDNKSYTSI LYGNGPGYVL   420
GGGLRPDVND SISEDPSYRQ QAAVPLSSES HGGEDVAVFA RGPQAHLVHG VQEETFVAHV   480
MAFAGCVEPY TDCNLPAPSG LSDAAHLA                                      508

SEQ ID NO: 8           moltype = AA  length = 754
FEATURE                Location/Qualifiers
REGION                 1..754
                       note = Synthetic polymer
source                 1..754
                       mol_type = protein
                       organism = synthetic construct
SEQUENCE: 8
MQGACVLLLL GLHLQLSLGL IPAEEENPAF WNRQAAQALD VAKKLQPIQT AAKNVILFLG    60
DGMGVPTVTA TRILKGQMNG KLGPETPLAM DQFPYVALSK TYNVDRQVPD SAGTATAYLC   120
GVKGNYRTIG VSAAARYNQC NTTRGNEVTS VINRAKKAGK AVGVVTTRV QHASPAGAYA    180
HTVNRNWYSD ADLPADAQKN GCQDIAAQLV YNMDIDVILG GGRMYMFPEG TPDPEYPDDA   240
SVNGVRKDKQ NLVQEWQAKH QGAQYVWNRT ALLQAADDSS VTHLMGLFEP ADMKYNVQQD   300
HTKDPTLAEM TEAALQVLSR NPRGFYLFVE GGRIDHGHHD GKAYMALTEA IMFDNAIAKA   360
NELTSELDTL ILVTADHSHV FSFGGYTLRG TSIFGLAPGK ALDSKSYTSI LYGNGPGYAL   420
GGGSRPDVNG STSEEPSYRQ QAAVPLASET HGGEDVAVFA RGPQAHLVHG VQEETFVAHI   480
MAFAGCVEPY TDCNLPAPAT ATSIPDGGSG GSGGGGSGGG GSEPKSCDKT HTCPPCPAPE   540
LLGGPSVFLF PPKPKDTLMI SRTPEVTCVV VDVSHEDPQV KFNWYVDGVQ VHNAKTKPRE   600
QQYNSTYRVV SVLTVLHQNW LDGKEYKCKV SNKALPAPIE KTISKAKGQP REPQVYTLPP   660
SREEMTKNQV SLTCLVKGFY PSDIAVEWES NGQPENNYKT TPPVLDSDGS FFLYSKLTVD   720
KSRWQQGNVF SCSVMHEALH NHYTQKSLSL SPGK                              754

SEQ ID NO: 9           moltype = AA  length = 751
FEATURE                Location/Qualifiers
REGION                 1..751
                       note = Synthetic polymer
source                 1..751
                       mol_type = protein
                       organism = synthetic construct
SEQUENCE: 9
MQWACVLLLL GLWLQLSLTF IPAEEEDPAF WNRQAAQALD VAKKLQPIQT AAKNVILFLG    60
DGMGVPTVTA TRILKGQMNG KLGPETPLAM DQFPYVALSK TYNVDRQVPD SAGTATAYLC   120
GVKGNYKTIG VSAAARYNQC NTTSGNEVTS VMNRAKKAGK SVGVVTTSRV QHASPAGAYA   180
HTVNRNWYSD ADLPADAQTY GCQDIATQLV NNMDIDVILG GGRMYMFPEG TPDPEYPYDV   240
NQTGVRKDKR NLVQEWQAKH QGAQYVWNRT ELLQAANDPS VTHLMGLFEP ADMKYNVQQD   300
PTKDPTLEEM TEAALQVLSR NPQGFYLFVE GGRIDHGHHE GKAYMALTDT VMFDNAIAKA   360
NELTSELDTL ILATADHSHV FSFGGYTLRG TSIFGLAPSK ASDNKSYTSI LYGNGPGYVL   420
GGGLRPDVND SISEDPSYRQ QAAVPLSSES HGGEDVAVFA RGPQAHLVHG VQEETFVAHV   480
MAFAGCVEPY TDCNLPAPSG LSDGGSGGSG GGSGGGGSE PKSCDKTHTC PPCPAPELLG   540
GPSVFLFPPK PKDTLMISRT PEVTCVVVDV SHEDPQVKFN WYVDGVQVHN AKTKPREQQY   600
NSTYRVVSVL TVLHQNWLDG KEYKCKVSNK ALPAPIEKTI SKAKGQPREP QVYTLPPSRE   660
EMTKNQVSLT CLVKGFYPSD IAVEWESNGQ PENNYKTTPP VLDSDGSFFL YSKLTVDKSR   720
```

```
WQQGNVFSCS VMHEALHNHY TQKSLSLSPG K                               751

SEQ ID NO: 10            moltype = AA   length = 539
FEATURE                  Location/Qualifiers
REGION                   1..539
                         note = Synthetic polymer
source                   1..539
                         mol_type = protein
                         organism = synthetic construct
SEQUENCE: 10
MQWACVLLLL GLWLQLSLTF IPAEEEDPAF WNRQAAQALD VAKKLQPIQT AAKNVILFLG  60
DGMGVPTVTA TRILKGQMNG KLGPETPLAM DQFPYVALSK TYNVDRQVPD SAGTATAYLC  120
GVKGNYKTIG VSAAARYNQC NTTSGNEVTS VMNRAKKAGK SVGVVTTSRV QHASPAGAYA  180
HTVNRNWYSD ADLPADAQTY GCQDIATQLV NNMDIDVILG GGRMYMFPEG TPDPEYPYDV  240
NQTGVRKDKR NLVQEWQAKH QGAQYVWNRT ELLQAANDPS VTHLMGLFEP ADMKYNVQQD  300
PTKDPTLEEM TEAALQVLSR NPQGFYLFVE GGRIDHGHHE GKAYMALTDT VMFDNAIAKA  360
NELTSELDTL ILATADHSHV FSFGGYTLRG TSIFGLAPSK ASDNKSYTSI LYGNGPGYVL  420
GGGLRPDVND SISEDPSYRQ QAAVPLSSES HGGEDVAVFA RGPQAHLVHG VQEETFVAHV  480
MAFAGCVEPY TDCNLEVLFQ GPAPPAGTTD AAHPGRSVVP ALLPLRAGTL LLLETATAP  539

SEQ ID NO: 11            moltype = AA   length = 534
FEATURE                  Location/Qualifiers
REGION                   1..534
                         note = Synthetic polymer
source                   1..534
                         mol_type = protein
                         organism = synthetic construct
SEQUENCE: 11
MQWACVLLLL GLWLQLSLTF IPAEEEDPAF WNRQAAQALD VAKKLQPIQT AAKNVILFLG  60
DGMGVPTVTA TRILKGQMNG KLGPETPLAM DQFPYVALSK TYNVDRQVPD SAGTATAYLC  120
GVKGNYKTIG VSAAARYNQC NTTSGNEVTS VMNRAKKAGK SVGVVTTSRV QHASPAGAYA  180
HTVNRNWYSD ADLPADAQTY GCQDIATQLV NNMDIDVILG GGRMYMFPEG TPDPEYPYDV  240
NQTGVRKDKR NLVQEWQAKH QGAQYVWNRT ELLQAANDPS VTHLMGLFEP ADMKYNVQQD  300
PTKDPTLEEM TEAALQVLSR NPQGFYLFVE GGRIDHGHHE GKAYMALTDT VMFDNAIAKA  360
NELTSELDTL ILATADHSHV FSFGGYTLRG TSIFGLAPSK ASDNKSYTSI LYGNGPGYVL  420
GGGLRPDVND SISEDPSYRQ QAAVPLSSES HGGEDVAVFA RGPQAHLVHG VQEETFVAHV  480
MAFAGCVEPY TDCNLAPPAG TTDAAHPIEG RSVVPALLPL RAGTLLLLET ATAP        534

SEQ ID NO: 12            moltype = DNA   length = 1669
FEATURE                  Location/Qualifiers
misc_feature             1..1669
                         note = Synthetic polymer
source                   1..1669
                         mol_type = other DNA
                         organism = synthetic construct
SEQUENCE: 12
atgcaggggc cctgggtgct gctgctgctg ggcctgaggc tacagctctc cctgggcgtc  60
atcccaggta atgaggctcc ccaagctgtt ccacacacag ggcaccccct cagccaggct  120
gacctgatct ctactctccc cctggccagc tgaggaggag aacccggcct tctggaaccg  180
ccaggcagct gaggccctgg atgctgccaa gaagctgcag cccatccaga aggtcgccaa  240
gaacctcatc ctcttcctgg gcgatgggt гgggggtgtca acggtgacag ccaccaggat  300
cctaaagggg cagaagaatg gcaaactggg gcctgagacg cccctggcca tggaccgctt  360
cccatacctg gctctgtcca agacatacaa tgtggacaga caggtgccag acagcgcagc  420
cacagccacg gcctacctgt gcggggtcaa ggccaacttc cagaccatcg gcttgagtgc  480
agccgcccgc tttaaccagt gcaacacgac acgcggcaat gaggtcatct ccgtgatgaa  540
ccgggccaag caagcaggaa agtcagtagg agtggtgacc accacacggg tgcagcacgc  600
ctcgccagcc ggcacctacg cacacacagt gaaccgcaac tggtactcag atgctgacat  660
gcctgcctca gcccgccagg aggggtgcca ggacatcgcc actcagctca tctccaacat  720
ggacattgac gtgatccttg gcggaggccg caagtacatg tttcccatgg ggaccccaga  780
ccctgagtac ccagctgatg ccagccagaa tggaatcagg ctggacggga agaacctggt  840
gcaggaatgg ctggcaaagc accagggtgc ctggtatgtg tggaaccgca ctgagctcat  900
gcaggcgtcc ctgaccagt ctgtgaccca tctcatgggc ctctttgagc ccggagacac  960
gaaatatgag atccaccgag accccacact ggacccctcc ctgatggaga tgacagaggc  1020
tgccctgcgc ctgctgagca ggaacccccg cggcttctac ctctttgtgg agggcgggcg  1080
catcgaccat ggtcatcatg aggggtgtggc ttaccaggca ctcactgagg cggtcatgtt  1140
cgacgacgcc attgagaggg cgggccagct caccagcgag gaggacacgc tgaccctcgt  1200
caccgctgac cactcccatg tcttctcctt tggtggctac accttgcgag ggagctccat  1260
cttcgggttg gcccccagca aggctcagga cagcaaagcc tacacgtcca tcctgtacgg  1320
caatggcccg ggctacgtgt tcaactcagg cgtgcgacca gacgtgaatg agagcgagag  1380
cgggagcccc gattaccagc agcaggcggc ggtgcccctg tcgtccgaga cccacggagg  1440
cgaagacgtg gcggtgtttg cgcgcggccc gcaggcgcac ctggtgcatg gtgtgcagga  1500
gcagagcttc gtagcgcatg tcatggcctt cgctgcctgt ctggagccct acacggcctg  1560
cgacctggcc cctcccgcct gcaccaccga cgccgcgcac ccagttgccg cgtcgctgcc  1620
actgctggcc gggaccctgc tgctgctggg ggcgtccgct gctccctga               1669

SEQ ID NO: 13            moltype = DNA   length = 1671
FEATURE                  Location/Qualifiers
misc_feature             1..1671
                         note = Synthetic polymer
```

-continued

```
source              1..1671
                    mol_type = other DNA
                    organism = synthetic construct
SEQUENCE: 13
atgcaggggc cctgggtgct gctgctgctg ggcctgaggc tacagctctc cctgggcgtc  60
atcccagctg aggaggagaa cccgccttc tggaaccgcc aggcagctga ggccctggat  120
gctgccaaga agctgcagcc catccagaag gtcgccaaga acctcatcct cttcctgggc  180
gatgggttgg gggtgcccac ggtgacagcc accaggatcc taaaggggca gaagaatggc  240
aaactggggc ctgagacgcc cctggccatg gaccgcttcc catacctggc tctgtccaag  300
acatacaatg tggacagaca ggtgacagac agcgcagcca cagccacggc ctacctgtgc  360
ggggtcaagg ccaacttcca gaccatcggc ttgagtgcag ccgccgctt taaccagtgc  420
aacacgacac gcggcaatga ggtcatctcc gtgatgaacc gggccaagca agcaggaaag  480
tcagtaggag tggtgaccac cacacgggtg cagcacgcct cgccagccgg cacctacgca  540
cacacagtga accgcaactg gtactcagat gctgacatgc ctgcctcagc ccgccaggag  600
gggtgccagg acatcgccac tcagctcatc tccaacatgg acattgacgt gatccttggc  660
ggaggccgca agtacatgtt tcccatgggg accccagacc ctgagtaccc agctgatgcc  720
agccagaatg gaatcaggct ggacgggaag aacctggtgc aggaatggct ggcaaagcac  780
cagggtgcct ggtatgtgtg gaaccgcact gagctcatgc aggcgtccct ggaccagtct  840
gtgacccatc tcatgggcct ctttgagccc ggagacacga aatatgagat ccaccgagac  900
cccacactgg acccctccct gatggagatg acagaggctg ccctgcgcct gctgagcagg  960
aaccccgcg gcttctacct ctttgtggag ggcggccgca tcgaccatgg tcatcatgag  1020
ggtgtggctt accaggcact cactgaggcg gtcatgttcg acgacgccat tgagagggcg  1080
ggccagctca ccagcgagga ggacacgctg accctcgtca ccgctgacca ctcccatgtc  1140
ttctcctttg gtggctacac cttgcgaggg agctccatct tcgggttggc ccccagcaag  1200
gctcaggaca gcaaagccta cacgtccatc ctgtacggca atggcccggg ctacgtgttc  1260
aactcaggcg tgcgaccaga cgtgaatgag agcgagacgg ggagccccga ttaccagcat  1320
caggcggcgg tgcccctgtc gtccgagacc cacggaggcg aagacgtggc ggtgtttgcg  1380
cgcggccgc aggcgcacct ggtgcatggt gtgcaggagc agagcttcgt agcgcatgtc  1440
atggccttcg ctgcctgtct ggagccctac acggcctgcg acctggcgcc tcccgcctgc  1500
accaccgacg ccgcgcaccc agttgccgcg tcgctgccac tgctggccgg gaccctgctg  1560
ctgctggggg cgtccgctgc tccctgattt actaaaacct tgaaataaaa ttgtaaaaca  1620
tcagtttgaa ggcctgactc tcagggtagt tcttttttaa ttctgggttt t  1671

SEQ ID NO: 14          moltype = DNA   length = 1672
FEATURE                Location/Qualifiers
misc_feature           1..1672
                       note = Synthetic polymer
source                 1..1672
                       mol_type = other DNA
                       organism = synthetic construct
SEQUENCE: 14
atgcagtggg cctgtgtgct gctgctgctg ggcctgtggc tacagctctc cctcaccttc  60
atcccaggta atcaggcggc tcccagcagc ccctactcac aggggcggct ctaggctgac  120
ctgaccaaca ctctccccctt gggcagctga ggaggaagac cccgccttct ggaaccgcca  180
ggcagcccag gcccttgatg tagccaagaa gttcagccg atccagacag ctgccaagaa  240
tgtcatcctc ttcttggggg atgggatggg ggtgcctacg gtgacagcca ctcggatcct  300
aaaggggcag atgaatggta agctgggacc tgagacacc ctggccatgg accagttccc  360
atacgtggct ctgtccaaga catacaacgt ggacagacag gtgccagaca gcgcaggcac  420
tgccactgcc tacctgtgtg gggtcaaggg caactacaaa accattggtg taagtgcagc  480
cgcccgctac aaccagtgca acacaacaag tggcaatgag gtcacgtctg tgatgaaccg  540
ggccaagaaa gcaggaaagt cagtgggat ggtgaccacc tccagggtgc agcatgcctc  600
cccagccggt gcttatgcac acacggtgaa ccgaaactgg tactcagatg ccgacctgcc  660
tgccgatgca cagacgtatg gctgccagga catcgccaca caactggtca acaacatgga  720
tattgacgtg atcctgggtg gaggccgaat gtacatgttt cctgagggga ccccggatcc  780
tgaatacoca tacgatgtca atcagactgg agtccggaag gacaagcgga atctggtcac  840
ggagtggcag gccaagcacc agggagccca gtatgtgtgg aaccgcacg agctccttca  900
ggcagccaat gaccccagtg taacacacct catgggcctc tttgagccgg cagacatgaa  960
gtataatgtt cagcaagacc ccaccaagga cccgaccctg gaggagatga cggaggcggc  1020
cctgcaagtg ctgagcagga accccagg cttctacctc ttcgtggagg gaggccgcat  1080
tgaccacggt caccatgaag gcaaagctta tatggcactg actgatacag tcatgtttga  1140
caatgccatc gccaaggcta acgagctcac tagcgaactg gacacgctga tccttgccac  1200
tgcagaccac tcccatgtct tctctttttgg tggctacaca ctgcgtggga cctccatttt  1260
cggtctggcc cccagcaagg cctcagacaa caagtcctac acctccatcc tctatggcaa  1320
tggccctggc tacgtgcttg gtgggggctt aaggcccgat gttaatgaca gcatagcgga  1380
ggaccctcg taccggcagc aggcggccgt gcccctgtct agtgagtccc acggggcga  1440
ggacgtggcg gtgttcgcgc gaggcccgca ggcgcacctg gtgcacggcg tgcaggagga  1500
gaccttcgtg gcgcacgtca tggccttgc gggctgcgtg gagccctaca ccgactgcaa  1560
tctgccggcc ccctctggcc tctccgacgc gcgcaccctg gcggcagcc cgccttgct  1620
ggcgctgctg gccggggcga tgctgctgct gctggcgcct gccttgtact ga  1672

SEQ ID NO: 15          moltype = DNA   length = 1869
FEATURE                Location/Qualifiers
misc_feature           1..1869
                       note = Synthetic polymer
source                 1..1869
                       mol_type = other DNA
                       organism = synthetic construct
SEQUENCE: 15
atgcagtggg cctgtgtgct gctgctgctg ggcctgtggc tacagctctc cctcaccttc  60
```

```
atcccagctg aggaggaaga ccccgccttc tggaaccgcc aggcagccca ggccccttgat    120
gtagccaaga agttgcagcc gatccagaca gctgccaaga atgtcatcct cttcttgggg    180
gatgggatgg gggtgcctac ggtgacagcc actcggatcc taaagggca gatgaatggt     240
aagctgggac ctgagacacc cctggccatg gaccagttcc catacgtggc tctgtccaag    300
acatacaacg tggacagaca ggtgccagac agcgcaggca ctgccactgc ctacctgtgt    360
ggggtcaagg gcaactacaa aaccattggt gtaagtgcag ccgcccgcta caaccagtgc    420
aacacaacaa gtggcaatga ggtcacgtct gtgatgaacc gggccaagaa agcaggaaag    480
tcagtgggag tggtgaccac ctccaggggtg cagcatgcct ccccagccgg tgcttatgca    540
cacacggtga accgaaactg gtactcagat gccgacctgc ctgccgatgc acagacgtat    600
ggctgccagg acatcgccac acaactggtc aacaacatgg atattgacgt gatcctgggt    660
ggaggccgaa tgtacatgtt tcctgagggg accccggatc ctgaataccc atacgatgtc    720
aatcagactg gagtccggaa ggacaagcgg aatctggtgc aggagtggca ggccaagcac    780
cagggagccc agtatgtgtg gaaccgcacg gagctccttc aggcagccaa tgaccccagt    840
gtaacacacc tcatgggcct ctttgagccg gcagacatga agtataatgt tcagcaagac    900
cccaccaagg acccgaccct ggaggagatg acggaggcgg ccctgcaagt gctgagcagg    960
aaccccagg gcttctacct cttcgtggag ggaggccgca ttgaccacgg tcaccatgaa     1020
ggcaaagctt atatggcact gactgataca gtcatgtttg acaatgccat cgccaaggct    1080
aacgagctca ctagcgaact ggacacgctg atccttgcca gtcagacca ctcccatgtc     1140
ttctctttg gtggctacac actgcgtggg acctccattt tcggtctggc ccccagcaag    1200
gcctcagaca caagtccta cacctccatc ctctatggca atggccctgg ctacgtgctt     1260
ggtgggggct taaggcccga tgttaatgac agcataagcg aggacccctc gtaccggcag    1320
caggcggccg tgcccctgtc tagtgagtcc cacggggccg aggacgtggc ggtgttcgcg   1380
cgaggcccgc aggcgcacct ggtgcacggc gtgcaggagg agaccttcgt ggcgcacgtc    1440
atggcctttg cgggctgcgt ggagccctac accgactgca atctgccggc ccctctggc     1500
ctctccgacg ccgcgcacct ggcggccagc ccgccttcgc tggcgctgct ggccggggcg    1560
atgctgctgc tgctggcgcc tgccttgtac tgagggggacc cggggggtggc ggcacaggcc   1620
ccgccctccc tgggaggcag gaagcagctc tcaaataaac tgttctaagt atgatacagg    1680
agtgatacat gtgtgaagag aagcccttag gtggggggcac agagtgtctg ggtgagggg     1740
gtcagggtca catcaggagg ttaggaggg gttgatgaag ggctgacgtt gagcaaagac     1800
caaaggcaac tcagaaggac agtggtgcag gactgggtgt ggtcagcagg gggactggtt    1860
ggggggatcc                                                            1869
```

SEQ ID NO: 16         moltype = DNA   length = 1260
FEATURE               Location/Qualifiers
misc_feature          1..1260
                      note = Synthetic polymer
source                1..1260
                      mol_type = other DNA
                      organism = synthetic construct
SEQUENCE: 16
```
aaaaaacaag acaaagctga gatcagaaat gtcattgtga tgataggcga cggcatgggg    60
acgcccttaca taagagccta ccgttccatg aaaaataacg gtgacacacc gaataacccg    120
aagttaacag aatttgaccg gaacctgaca ggcatgatgg cgcatccatcc ggatgaccct    180
gactataata ttacagattc agcagcagcc ggaacagcat tagcgacagg cgttaagaca     240
tataacaatg caattggcgt cgataaaaac ggaaaaaaag tgaaatctgt acttgaagag    300
gccaaacagc aaggcaagtc aacagggctt gtcgccacgt ctgaaattaa ccacgccact    360
ccagccgcat atggcgccca caatgaatca cggaaaaaca cgccaacagc cagccaaat     420
tatatggatg acaagataaa aggcaaacat aaaatagacg tgctgctcgg cggcggaaaa    480
tcttatttta accgcaagaa cagaaacttg acaaaggaat tcaaacaagc cggctacagc    540
tatgtgacaa ctaaacaagc attgaaaaaa aataaagatc agcaggtgct cgggcttttc    600
gcagatggag ggcttgctaa agcgctcgac cgtgacagta aaacaccgtc tctcaaagac   660
atgacggttt cagcaattga tcgcctgaac caaaataaaa aaggattttt cttgatggtc    720
gaagggagcc agattgactg ggcggcccat gacaatgata cagtaggagc catgagcgag    780
gttaaagatt ttgaacaggc ctataaagcc gcgattgaat ttgcgaaaaa agacaaacat    840
acacttgtga ttgcaactgc tgaccataca accggcggtt ttaccattgg cgcaaacggg    900
gaaaagaatt ggcacgcaga accgattctc tccgctaaga aaacacctga attcatggcc   960
aaaaaaatca gtgaaggcaa gccggttaaa gatgtgctcg cccgctatgc caatctgaaa    1020
gtcacatctg aagaaatcaa aagcgttgaa gcagctgcac aggctgacaa aagcaaaggg    1080
gcctccaaag ccatcatcaa gatttttaat acccgctcca acagcggatg gacgagtacc    1140
gatcataccg gcgaagaagt accggtatac gcgtacggcc cggaaaaaga aaaattccgc    1200
ggattgatta acaatacgga caatacgcaa atcatcattta cgattttaaa aactggaaaa    1260
```

SEQ ID NO: 17         moltype = AA    length = 420
FEATURE               Location/Qualifiers
REGION                1..420
                      note = Synthetic polymer
source                1..420
                      mol_type = protein
                      organism = synthetic construct
SEQUENCE: 17
```
KKQDKAEIRN VIVMIGDGMG TPYIRAYRSM KNNGDTPNNP KLTEFDRNLT GMMMTHPDDP    60
DYNITDSAAA GTALATGVKT YNNAIGVDKN GKKVKSVLEE AKQQGKSTGL VATSEINHAT    120
PAAYGAHNES RKNMDQIANS YMDDKIKGKH KIDVLLGGGK SYFNRKNRNL TKEFKQAGYS    180
YVTTKQALKK NKDQQVLGLF ADGGLAKALD RDSKTPSLKD MTVSAIDRLN QNKKGFFLMV    240
EGSQIDWAAH DNDTVGAMSE VKDFEQAYKA AIEFAKKDKH TLVIATADHT TGGFTIGANG    300
EKNWHAEPIL SAKKTPEFMA KKISEGKPVK DVLARYANLK VTSEEIKSVE AAAQADKSKG    360
ASKAIIKIFN TRSNSGWTST DHTGEEVPVY AYGPGKEKFR GLINNTDQAN IIFKILKTGK    420
```

SEQ ID NO: 18         moltype = AA    length = 776

-continued

```
FEATURE          Location/Qualifiers
REGION           1..776
                 note = Synthetic polymer
source           1..776
                 mol_type = protein
                 organism = synthetic construct
SEQUENCE: 18
MQGPWVLLLL GLRLQLSLGV IPAEEENPAF WNRQAAEALD AAKKLQPIQK VAKNLILFLG  60
DGLGVPTVTA TRILKGQKNG KLGPETPLAM DRFPYLALSK TYNVDRQVPD SAATATAYLC  120
GVKANFQTIG LSAAARFNQC NTTRGNEVIS VMNRAKQAGK SVGVVTTTRV QHASPAGTYA  180
HTVNRNWYSD ADMPASARQE GCQDIATQLI SNMDIDVILG GGRKYMFPMG TPDPEYPADA  240
SQNGIRLDGK NLVQEWLAKH QGAWYVWNRT ELMQASLDQS VTHLMGLFEP GDTKYEIHRD  300
PTLDPSLMEM TEAALRLLSR NPRGFYLFVE GGRIDHGHHE GVAYQALTEA VMFDDAIERA  360
GQLTSEEDTL TLVTADHSHV FSFGGYTLRG SSIFGLAPSK AQDSKAYTSI LYGNGPGYVF  420
NSGVRPDVNE SESGSPDYQQ QAAVPLSSET HGGEDVAVFA RGPQAHLVHG VQEQSFVAHV  480
MAFAACLEPY TACDLAPPAC TTDAAHPVAA SLPLLAGTLL LLGASAAPGG SGGSGGGGSG  540
GGGSEPKSCD KTHTCPPCPA PELLGGPSVF LFPPKPKDTL MISRTPEVTC VVVDVSHEDP  600
QVKFNWYVDG VQVHNAKTKP REQQYNSTYR VVSVLTVLHQ NWLDGKEYKC KVSNKALPAP  660
IEKTISKAKG QPREPQVYTL PPSREEMTKN QVSLTCLVKG FYPSDIAVEW ESNGQPENNY  720
KTTPPVLDSD GSFFLYSKLT VDKSRWQQGN VFSCSVMHEA LHNHYTQKSL SLSPGK      776

SEQ ID NO: 19    moltype = DNA  length = 18
FEATURE          Location/Qualifiers
misc_feature     1..18
                 note = Synthetic polymer
source           1..18
                 mol_type = other DNA
                 organism = synthetic construct
SEQUENCE: 19
catggaccgc ttcccata                                                 18

SEQ ID NO: 20    moltype = DNA  length = 20
FEATURE          Location/Qualifiers
misc_feature     1..20
                 note = Synthetic polymer
source           1..20
                 mol_type = other DNA
                 organism = synthetic construct
SEQUENCE: 20
cttgcactgt ctggaacctg                                               20

SEQ ID NO: 21    moltype = DNA  length = 20
FEATURE          Location/Qualifiers
misc_feature     1..20
                 note = Synthetic polymer
source           1..20
                 mol_type = other DNA
                 organism = synthetic construct
SEQUENCE: 21
cagcgatgcc cacaggaaag                                               20

SEQ ID NO: 22    moltype = DNA  length = 19
FEATURE          Location/Qualifiers
misc_feature     1..19
                 note = Synthetic polymer
source           1..19
                 mol_type = other DNA
                 organism = synthetic construct
SEQUENCE: 22
acggagccct tgacgagag                                                19

SEQ ID NO: 23    moltype = DNA  length = 20
FEATURE          Location/Qualifiers
misc_feature     1..20
                 note = Synthetic polymer
source           1..20
                 mol_type = other DNA
                 organism = synthetic construct
SEQUENCE: 23
cgtttccggt tcaagctcac                                               20

SEQ ID NO: 24    moltype = DNA  length = 23
FEATURE          Location/Qualifiers
misc_feature     1..23
                 note = Synthetic polymer
source           1..23
                 mol_type = other DNA
                 organism = synthetic construct
SEQUENCE: 24
```

-continued

```
cctgatgact ttgatgctga acg                                          23

SEQ ID NO: 25          moltype = DNA   length = 20
FEATURE                Location/Qualifiers
misc_feature           1..20
                       note = Synthetic polymer
source                 1..20
                       mol_type = other DNA
                       organism = synthetic construct
SEQUENCE: 25
actccttctg tgactccagc                                              20

SEQ ID NO: 26          moltype = DNA   length = 20
FEATURE                Location/Qualifiers
misc_feature           1..20
                       note = Synthetic polymer
source                 1..20
                       mol_type = other DNA
                       organism = synthetic construct
SEQUENCE: 26
ataactgcac ccacttccca                                              20

SEQ ID NO: 27          moltype = DNA   length = 23
FEATURE                Location/Qualifiers
misc_feature           1..23
                       note = Synthetic polymer
source                 1..23
                       mol_type = other DNA
                       organism = synthetic construct
SEQUENCE: 27
gcactacagg ctccgagatg aac                                          23

SEQ ID NO: 28          moltype = DNA   length = 24
FEATURE                Location/Qualifiers
misc_feature           1..24
                       note = Synthetic polymer
source                 1..24
                       mol_type = other DNA
                       organism = synthetic construct
SEQUENCE: 28
ttgtcgttgc ttggttctcc ttgt                                         24

SEQ ID NO: 29          moltype = DNA   length = 21
FEATURE                Location/Qualifiers
misc_feature           1..21
                       note = Synthetic polymer
source                 1..21
                       mol_type = other DNA
                       organism = synthetic construct
SEQUENCE: 29
cctctggtct tctggagtac c                                            21

SEQ ID NO: 30          moltype = DNA   length = 20
FEATURE                Location/Qualifiers
misc_feature           1..20
                       note = Synthetic polymer
source                 1..20
                       mol_type = other DNA
                       organism = synthetic construct
SEQUENCE: 30
actccttctg tgactccagc                                              20

SEQ ID NO: 31          moltype = DNA   length = 20
FEATURE                Location/Qualifiers
misc_feature           1..20
                       note = Synthetic polymer
source                 1..20
                       mol_type = other DNA
                       organism = synthetic construct
SEQUENCE: 31
tctccaccgc aatgaagacc                                              20

SEQ ID NO: 32          moltype = DNA   length = 20
FEATURE                Location/Qualifiers
misc_feature           1..20
                       note = Synthetic polymer
source                 1..20
                       mol_type = other DNA
                       organism = synthetic construct
```

```
SEQUENCE: 32
cacacccacc agcatcttct                                                    20

SEQ ID NO: 33          moltype = DNA   length = 20
FEATURE                Location/Qualifiers
misc_feature           1..20
                       note = Synthetic polymer
source                 1..20
                       mol_type = other DNA
                       organism = synthetic construct
SEQUENCE: 33
gctaagagca cagcaatgga                                                    20

SEQ ID NO: 34          moltype = DNA   length = 20
FEATURE                Location/Qualifiers
misc_feature           1..20
                       note = Synthetic polymer
source                 1..20
                       mol_type = other DNA
                       organism = synthetic construct
SEQUENCE: 34
gcatgttcaa cgttatccat                                                    20

SEQ ID NO: 35          moltype = DNA   length = 19
FEATURE                Location/Qualifiers
misc_feature           1..19
                       note = Synthetic polymer
source                 1..19
                       mol_type = other DNA
                       organism = synthetic construct
SEQUENCE: 35
cacgcaatcc tggatgtca                                                     19

SEQ ID NO: 36          moltype = DNA   length = 18
FEATURE                Location/Qualifiers
misc_feature           1..18
                       note = Synthetic polymer
source                 1..18
                       mol_type = other DNA
                       organism = synthetic construct
SEQUENCE: 36
gtcgcgcctg ctgttgct                                                      18

SEQ ID NO: 37          moltype = DNA   length = 23
FEATURE                Location/Qualifiers
misc_feature           1..23
                       note = Synthetic polymer
source                 1..23
                       mol_type = other DNA
                       organism = synthetic construct
SEQUENCE: 37
ccccatctga ctatgtggaa aga                                                23

SEQ ID NO: 38          moltype = DNA   length = 23
FEATURE                Location/Qualifiers
misc_feature           1..23
                       note = Synthetic polymer
source                 1..23
                       mol_type = other DNA
                       organism = synthetic construct
SEQUENCE: 38
aaaaccgctt gtcattcact ttg                                                23

SEQ ID NO: 39          moltype = DNA   length = 23
FEATURE                Location/Qualifiers
misc_feature           1..23
                       note = Synthetic polymer
source                 1..23
                       mol_type = other DNA
                       organism = synthetic construct
SEQUENCE: 39
caggagcgag accccactaa cat                                                23

SEQ ID NO: 40          moltype = DNA   length = 23
FEATURE                Location/Qualifiers
misc_feature           1..23
                       note = Synthetic polymer
source                 1..23
                       mol_type = other DNA
```

-continued

```
                         organism = synthetic construct
SEQUENCE: 40
gtcagatcca cgacggacac att                                          23

SEQ ID NO: 41           moltype = AA  length = 16
FEATURE                 Location/Qualifiers
REGION                  1..16
                        note = Synthetic polymer
source                  1..16
                        mol_type = protein
                        organism = synthetic construct
SEQUENCE: 41
GGSGGSGGGG SGGGGS                                                  16

SEQ ID NO: 42           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 42
GGGGS                                                               5

SEQ ID NO: 43           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 43
GGGGSGGGGS                                                         10

SEQ ID NO: 44           moltype = AA  length = 15
FEATURE                 Location/Qualifiers
REGION                  1..15
                        note = Synthetic polymer
source                  1..15
                        mol_type = protein
                        organism = synthetic construct
SEQUENCE: 44
GGGGSGGGGS GGGGS                                                   15

SEQ ID NO: 45           moltype = AA  length = 20
FEATURE                 Location/Qualifiers
REGION                  1..20
                        note = Synthetic polymer
source                  1..20
                        mol_type = protein
                        organism = synthetic construct
SEQUENCE: 45
GGGGSGGGGS GGGGSGGGGS                                              20

SEQ ID NO: 46           moltype = AA  length = 8
FEATURE                 Location/Qualifiers
REGION                  1..8
                        note = Synthetic polymer
source                  1..8
                        mol_type = protein
                        organism = synthetic construct
SEQUENCE: 46
GGGGGGGG                                                            8

SEQ ID NO: 47           moltype = AA  length = 6
FEATURE                 Location/Qualifiers
REGION                  1..6
                        note = Synthetic polymer
source                  1..6
                        mol_type = protein
                        organism = synthetic construct
SEQUENCE: 47
GGGGGG                                                              6

SEQ ID NO: 48           moltype = AA  length = 5
FEATURE                 Location/Qualifiers
REGION                  1..5
                        note = Synthetic polymer
source                  1..5
```

```
                              mol_type = protein
                              organism = synthetic construct
SEQUENCE: 48
EAAAK                                                                    5

SEQ ID NO: 49          moltype = AA   length = 10
FEATURE                Location/Qualifiers
REGION                 1..10
                       note = Synthetic polymer
source                 1..10
                       mol_type = protein
                       organism = synthetic construct
SEQUENCE: 49
EAAAKEAAAK                                                               10

SEQ ID NO: 50          moltype = AA   length = 15
FEATURE                Location/Qualifiers
REGION                 1..15
                       note = Synthetic polymer
source                 1..15
                       mol_type = protein
                       organism = synthetic construct
SEQUENCE: 50
EAAAKEAAAK EAAAK                                                         15

SEQ ID NO: 51          moltype = AA   length = 12
FEATURE                Location/Qualifiers
REGION                 1..12
                       note = Synthetic polymer
source                 1..12
                       mol_type = protein
                       organism = synthetic construct
SEQUENCE: 51
AEAAAKEAAA KA                                                            12

SEQ ID NO: 52          moltype = AA   length = 17
FEATURE                Location/Qualifiers
REGION                 1..17
                       note = Synthetic polymer
source                 1..17
                       mol_type = protein
                       organism = synthetic construct
SEQUENCE: 52
AEAAAKEAAA KEAAAKA                                                       17

SEQ ID NO: 53          moltype = AA   length = 21
FEATURE                Location/Qualifiers
REGION                 1..21
                       note = Synthetic polymer
source                 1..21
                       mol_type = protein
                       organism = synthetic construct
SEQUENCE: 53
AEAAAKEAAA KEAAAKEAAA K                                                  21

SEQ ID NO: 54          moltype = AA   length = 27
FEATURE                Location/Qualifiers
REGION                 1..27
                       note = Synthetic polymer
source                 1..27
                       mol_type = protein
                       organism = synthetic construct
SEQUENCE: 54
AEAAAKEAAA KEAAAKEAAA KEAAAKA                                            27

SEQ ID NO: 55          moltype = AA   length = 12
FEATURE                Location/Qualifiers
REGION                 1..12
                       note = Synthetic polymer
source                 1..12
                       mol_type = protein
                       organism = synthetic construct
SEQUENCE: 55
AEAAAKEAAA KA                                                            12

SEQ ID NO: 56          moltype = AA   length = 46
FEATURE                Location/Qualifiers
REGION                 1..46
                       note = Synthetic polymer
```

```
source                  1..46
                        mol_type = protein
                        organism = synthetic construct
SEQUENCE: 56
AEAAAKEAAA KEAAAKEAAA KALEAEAAAK EAAAKEAAAK EAAAKA                    46

SEQ ID NO: 57           moltype = AA  length = 5
FEATURE                 Location/Qualifiers
REGION                  1..5
                        note = Synthetic polymer
source                  1..5
                        mol_type = protein
                        organism = synthetic construct
SEQUENCE: 57
PAPAP                                                                  5

SEQ ID NO: 58           moltype = AA  length = 18
FEATURE                 Location/Qualifiers
REGION                  1..18
                        note = Synthetic polymer
source                  1..18
                        mol_type = protein
                        organism = synthetic construct
SEQUENCE: 58
KESGSVSSEQ LAQFRSLD                                                   18

SEQ ID NO: 59           moltype = AA  length = 14
FEATURE                 Location/Qualifiers
REGION                  1..14
                        note = Synthetic polymer
source                  1..14
                        mol_type = protein
                        organism = synthetic construct
SEQUENCE: 59
EGKSSGSGSE SKST                                                       14

SEQ ID NO: 60           moltype = AA  length = 12
FEATURE                 Location/Qualifiers
REGION                  1..12
                        note = Synthetic polymer
source                  1..12
                        mol_type = protein
                        organism = synthetic construct
SEQUENCE: 60
GSAGSAAGSG EF                                                         12
```